(12) United States Patent
Andersen et al.

(10) Patent No.: US 10,961,593 B2
(45) Date of Patent: *Mar. 30, 2021

(54) METHODS AND COMPOSITIONS FOR IDENTIFICATION OF SOURCE OF MICROBIAL CONTAMINATION IN A SAMPLE

(71) Applicant: The Regents of the University of California, Oakland, CA (US)

(72) Inventors: Gary L. Andersen, Berkeley, CA (US); Eric A. Dubinsky, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/642,682

(22) Filed: Jul. 6, 2017

(65) Prior Publication Data
US 2017/0335374 A1    Nov. 23, 2017

Related U.S. Application Data

(63) Continuation of application No. 13/787,500, filed on Mar. 6, 2013, now Pat. No. 9,725,770.

(60) Provisional application No. 61/607,340, filed on Mar. 6, 2012.

(51) Int. Cl.
| | | |
|---|---|---|
| C12Q 1/68 | (2018.01) | |
| C07H 21/00 | (2006.01) | |
| C12Q 1/689 | (2018.01) | |

(52) U.S. Cl.
CPC ............. *C12Q 1/689* (2013.01); *C07H 21/00* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 8,771,940 | B2 * | 7/2014 | Andersen ............... | G16B 25/00 435/6.1 |
| 9,725,770 | B2 * | 8/2017 | Andersen ............... | C12Q 1/689 |
| 2001/0053519 | A1 * | 12/2001 | Fodor .................. | B01J 19/0046 435/6.11 |
| 2002/0001546 | A1 * | 1/2002 | Hunter ................ | B01F 13/0071 422/82.05 |
| 2003/0162210 | A1 * | 8/2003 | Chetverin ............ | B01J 19/0046 435/6.14 |
| 2004/0033547 | A1 | 2/2004 | Field | |
| 2005/0053942 | A1 * | 3/2005 | Kauppinen ......... | C12N 15/1006 435/6.12 |
| 2005/0079517 | A1 * | 4/2005 | Goncharko ............. | B01B 1/005 435/6.11 |
| 2007/0122831 | A1 | 5/2007 | Bachoon | |
| 2007/0172854 | A1 * | 7/2007 | Matsumura .......... | C12Q 1/6837 435/6.16 |
| 2009/0203032 | A1 | 8/2009 | Shanks | |
| 2009/0291858 | A1 | 11/2009 | Andersen | |
| 2011/0143334 | A1 | 6/2011 | Roscoe | |
| 2012/0165215 | A1 | 6/2012 | Andersen | |
| 2012/0190025 | A1 | 7/2012 | Blackwood | |
| 2012/0264637 | A1 | 10/2012 | Wiener-Kronish | |

FOREIGN PATENT DOCUMENTS

| | | |
|---|---|---|
| WO | WO 1999/22023 | 5/1999 |
| WO | WO 2007/018563 | 2/2007 |
| WO | WO 2007/039319 | 4/2007 |

OTHER PUBLICATIONS

Brenan et al., High throughput nanoliter quantitative PCR. Drug Discovery Today : Technologies 2(3) :247 (Year: 2005).*
Fan et al., Illumina Universal Bead Arrays. Methods in E#nzymology 410 : 57 (Year: 2006).*
Susi et al., Typing of Enteroviruses by Use of Microwell Oligonucleotide Arrays. J. of Clinical Microbiology 47(6) : 1863 (Year: 2009).*
Wei et al., Using a microfluidic device for 1 microliter DNAmicroarray hybridization in 500 s. Nucleic Acids Research 33(8) : e78 (Year: 2005).*
Dubinsky et al., "Application of Phylogenetic Microarray Analysis to Discriminate Sources of Fecal Pollution", *Environmental Science & Technology*, 2012, vol. 46, pp. 4340-4347.
Bavykin et al., "Portable System for Microbial Sample Preparation and Oligonucleotide Microarray Analysis" Appl. Environ. Microbiol. Feb. 2001 vol. 67 No. 2, pp. 922-928.
Bernhard et al., "A PCR Assay To Discriminate Human and Ruminant Feces on the Basis of Host Differences in *Bacteroides-Prevotella* Genes Encoding 16S rRNA" Appl. Environ. Microbiol. Oct. 2000 vol. 66 No. 10, pp. 4571-4574.
Bernhard et al., "Identification of Nonpoint Sources of Fecal Pollution in Coastal Waters by Using Host-Specific 16S Ribosomal DNA Genetic Markers from Fecal Anaerobes" Appl. Environ. Microbiol. Apr. 2000 vol. 66 No. 4, pp. 1587-1594.
Brodie et al., "Urban aerosols harbor diverse and dynamic bacterial populations" Appl. Environ. Microbiol. 2006 vol. 104 No. 1, pp. 299-304.
Brodie et al., "Application of a High-Density Oligonucleotide Microarray Approach to Study Bacterial Population Dynamics during Uranium Reduction and Reoxidation" Appl. Environ. Microbiol. 2006 vol. 72 No. 9, 6288-6298.
Cho et al, "Bacterial Species Determination from DNA-DNA Hybridization by Using Genome Fragments and DNA Microarrays" Appl. Environ. Microbiol. Aug. 2001 vol. 67 No. 8, pp. 3677-3682.
Desantis et al., "Rapid quantification and taxonomic classification of environmental DNA from both prokaryotic and eukaryotic origins using a microarray" *FEMS Microbiol Lett* 2005; 245 (2): 271-278.

(Continued)

*Primary Examiner* — Ethan C Whisenant
(74) *Attorney, Agent, or Firm* — Sheppard, Mullin, Richter & Hampton LLP

(57) ABSTRACT

Herein are described 1058 different bacterial taxa that were unique to either human, grazing mammal, or bird fecal wastes. These identified taxa can serve as specific identifier taxa for these sources in environmental waters. Two field tests in marine waters demonstrate the capacity of phylogenetic microarray analysis to track multiple sources with one test.

19 Claims, 7 Drawing Sheets

Specification includes a Sequence Listing.

(56) References Cited

OTHER PUBLICATIONS

Guschin et al. "Oligonucleotide microchips as genosensors for determinative and environmental studies in microbiology" Appl. Environ. Microbiol. Jun. 1997 vol. 63 No. 6, pp. 2397-2402.

Kildare et al., "16S rRNA-based assays for quantitative detection of universal, human-, cow-, and dog-specific fecal *Bacteroidales*: A Bayesian approach" Water Research vol. 41, Issue 16, Aug. 2007, pp. 3701-3715.

Palmer et al., "Rapid quantitative profiling of complex microbial populations" *Nucleic Acids Res* 2006; 34 (1): e5. doi: 10.1093/nar/gnj007.

Peplies et al., "A DNA Microarray Platform Based on Direct Detection of rRNA for Characterization of Freshwater Sediment-Related Prokaryotic Communities" Appl. Environ. Microbiol. Jul. 2006 vol. 72 No. 7, pp. 4829-4838.

Peplies et al., Optimization Strategies for DNA Microarray-Based Detection of Bacteria with 16S rRNA-Targeting Oligonucleotide Probes Appl. Environ. Microbiol. Mar. 2003 vol. 69 No. 3, pp. 1397-1407.

Rompre et al., "Detection and enumeration of coliforms in drinking water: current methods and emerging approaches" Journal of Microbiological Methods, vol. 49, Issue 1, Mar. 2002, pp. 31-54.

Sagaram et al., "Bacterial Diversity Analysis of Huanglongbing Pathogen-Infected Citrus, Using PhyloChip Arrays and 16S rRNA Gene Clone Library Sequencing" Appl. Environ. Microbiol. Mar. 2009 vol. 75 No. 6, pp. 1566-1574.

Small et al., "Direct Detection of 16S rRNA in Soil Extracts by Using Oligonucleotide Microarrays" Appl. Environ. Microbiol. Oct. 2001 vol. 67 No. 10, pp. 4708-4716.

Wilson et al., "High-Density Microarray of Small-Subunit Ribosomal DNA Probes" Appl. Environ. Microbiol. May 2002 vol. 68 No. 5, pp. 2535-2541.

Yi-Bo et all, "Design Of 16 S rRNA-Based Oligonucleotide Array Using Group-Specific Non-Unique Probes In Large Scale Bacteria Detection" Progress in Biochemistry and Biophysics 2009, 36(8): 1025-1034.

File History of U.S. Appl. No. 12/474,204, filed May 28, 2009.
File History of U.S. Appl. No. 13/379,839, filed Mar. 12, 2012.
File History of U.S. Appl. No. 13/502,108, filed Jun. 27, 2012.
Svensen, N. et al. (2011) Microarray generation of thousand-member oligonucleotide libraries. PLoS One. 6(9):1-8: e24906. doi:10.1371/journal.pone.0024906. Epub Sep. 23, 2011.

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
ggttaccttg ttacgactt                                               19
```

METHODS AND COMPOSITIONS FOR IDENTIFICATION OF SOURCE OF MICROBIAL CONTAMINATION IN A SAMPLE

CROSS-REFERENCE TO RELATED APPLICATIONS

This application is a continuation application of U.S. patent application Ser. No. 13/787,500, filed on Mar. 6, 2013, which is a non-provisional application of and claims priority to U.S. Provisional Patent Application No. 61/607,340, filed on Mar. 6, 2012, hereby incorporated by reference in its entirety. This application is also related to U.S. patent application Ser. No. 13/379,839, filed on Dec. 21, 2011, which is also incorporated by reference in its entirety.

STATEMENT OF GOVERNMENTAL SUPPORT

This invention was made with government support under Contract No. DE-AC02-05CH11231 awarded by the U.S. Department of Energy, and under Grant No. ES013515 awarded by the National Institute of Health. Further funding and support provided by the California State Water Resources Control Board Clean Beaches initiative (07-576-550-0), and the County of Marin under Work for Others Agreement LB08004214, the US Environmental Protection Agency and the City of Dana Point. The government has certain rights in the invention.

REFERENCE TO TABLE APPENDIX

Table 1 is a list of the unique bird feces taxa identified.
Table 2 is a list of the unique grazer feces taxa identified.
Table 3 is a list of the unique sewage and human feces taxa identified.

The Tables 1, 2, and 3 are hereby incorporated by reference in their entirety.

BACKGROUND OF THE INVENTION

Field of the Invention

The present invention relates to identification of unique identifying sequences and taxa which can identify specific organism sources of contamination in samples, especially environmental samples, and methods and compositions that find use thereof.

Related Art

Beach closures and public health advisories have a major economic impact on coastal communities whose economies are based largely on tourism from beach recreation. Most closings and advisories are triggered by water samples that exceed microbial water quality standards for fecal indicator bacteria (FIB), usually culturable coliforms, *E. coli* or enterococci that are considered a proxy for human health risk in recreational waters. Because the direct measurement of all human pathogens is often impractical and unreliable under field conditions, water monitoring relies on the detection of bacterial indicators that have some demonstrated correlation with human illness in areas mostly impacted by Truman sewage (Field, K. G.; Samadpour, M., Fecal source tracking, the indicator paradigm, and managing water quality. *Water Research* 2007, 41, (16), 3517-3538; Wade, T. J.; Pai, N.; Eisenberg, J. N. S.; Colford, J. M., Do US Environmental Protection Agency water quality guidelines for recreational waters prevent gastrointestinal illness? A systematic review and meta-analysis. *Environmental Health Perspectives* 2003, 111, (8), 1102-1109). Sewage, however, is one of many potential sources of FIB, and monitoring results are often confounded by inputs from a variety of wildlife and non-fecal sources (Field, K. et al., *Water Research* 2007, 41, (16), 3517-3538; Boehm, A. B., Enterococci concentrations in diverse coastal environments exhibit extreme variability. *Environmental Science & Technology* 2007, 41, (24), 8227-8232; Boehm, A. B., Covariation and Photoinactivation of Traditional and Novel Indicator Organisms and Human Viruses at a Sewage-Impacted Marine Beach. *Environmental Science & Technology* 2009, 43, (21), 8046-8052; Yamahara, K. M.; Layton, B. A.; Santoro, A. E.; Boehm, A. B., Beach sands along the California coast are diffuse sources of fecal bacteria to coastal waters. *Environmental Science & Technology* 2007, 41, (13), 4515-4521). FIB are common in most warm-blooded animals, and many studies demonstrate that FIB occur in several environmental sources aside from feces, including soils and sediments, algal wrack and beach sands. Ibid. Thus water bodies often contain measurable amounts of FIB even where anthropogenic inputs are absent, and the presence of FIB provides an insufficient indication of health risk without additional source tracking data.

Shortcomings of the current FIB monitoring approach combined with widespread development and implementation of Total Maximum Daily Load (TMDL) requirements for microbiological pollution are fueling interest in microbial source tracking (MST) methods (Santo Domingo, J. W.; Bambic, D. G.; Edge, T. A.; Wuertz, S., Quo vadis source tracking? Towards a strategic framework for environmental monitoring of fecal pollution. *Water Research* 2007, 41, (16), 3539-52; USEPA, Microbial Source Tracking Guide Document. In Washington, D.C., 2005; p 131). Many approaches to source tracking are under development, most of which rely on single phenotypic or genotypic biomarkers to measure sources (Field, K., et al., *Water Research* 2007, 41, (16), 3517-3538; Santo Domingo, J. W. et al., Quo vadis source tracking? Towards a strategic framework for environmental monitoring of fecal pollution. *Water Research* 2007, 41, (16), 3539-52). A limitation of single targets is that no single assay is known to be 100% specific for any one type of waste (Field, K., et al., *Water Research* 2007, 41, (16), 3517-3538; Santo Domingo, J. W. et al., Quo vadis source tracking? Towards a strategic framework for environmental monitoring of fecal pollution. *Water Research* 2007, 41, (16), 3539-52), and MST based on single targets is entirely dependent on the fate of one biomarker once it enters receiving waters (Bae, S.; Wuertz, S., Rapid decay of host-specific fecal Bacteroidales cells in seawater as measured by quantitative PCR with propidium monoazide. *Water Research* 2009, 43, (19), 4850-4859; Balleste, E.; Blanch, A. R., Persistence of Bacteroides Species Populations in a River as Measured by Molecular and Culture Techniques. *Applied and Environmental Microbiology* 2010, 76, (22), 7608-7616; Walters, S. P.; Field, K. G., Survival and persistence of human and ruminant-specific faecal Bacteroidales in freshwater microcosms. *Environmental Microbiology* 2009, 11, (6), 1410-1421).

A huge diversity of microorganisms is resident in human and animal guts. Approximately 1000 different microbial taxa are now known to reside in the human gut alone, but the potential for this diversity to be used as a means for identifying sources remains largely unexplored and there have been few comparative surveys of microbial community composition among important sources of fecal contamination (Cao, Y.; Wu, C. H.; Andersen, G. L.; Holden, P. A., Community analysis-based methods. In *Microbial Source Tracking: Methods, Applications, and Case Studies*, Hagedorn, C.; Blanch, A. R.; Harwood, V. J., Eds. Springer: New York, N.Y., 2011; pp 251-282; Lee, J. E.; Lee, S.; Sung, J.; Ko, G., Analysis of human and animal fecal microbiota for microbial source tracking. *The ISME journal* 2011, 5, (2), 362-5; Unno, T.; Jang, J.; Han, D.; Kim, J. H.; Sadowsky, M. J.; Kim, O. S.; Chun, J.; Hur, H. G., Use of Barcoded Pyrosequencing and Shared OTUs To Determine Sources of Fecal Bacteria in Watersheds. *Environmental Science & Technology* 2010, 44, (20), 7777-7782). New techniques for high-throughput DNA sequence analysis such as high-density microarrays and next-generation sequencing (NGS) technologies like pyrosequencing are enabling comprehensive surveys of diverse microbial communities that occur in a sample. Targeting the whole microbial community for source identification is a fundamentally different approach than traditional molecular methods that are dependent on the detection on one gene sequence under complex environmental conditions (Cao, Y.; Wu, C. H.; Andersen, G. L.; Holden, P. A., Community analysis-based methods. In *Microbial Source Tracking: Methods, Applications, and Case Studies*, Hagedorn, C.; Blanch, A. R.; Harwood, V. J., Eds. Springer: New York, N.Y., 2011; pp 251-282; Wu, C. H.; Sercu, B.; Van de Werthorst, L. C.; Wong, J.; DeSantis, T. Z.; Brodie, E. L.; Hazen, T. C.; Holden, P. A.; Andersen, G. L., Characterization of Coastal Urban Watershed Bacterial Communities Leads to Alternative Community-Based Indicators. *PLoS One* 2010, 5, (6), e11285; Cao, Y. P.; Van De Werfhorst, L. C.; Sercu, B.; Murray, J. L. S.; Holden, P. A., Application of an Integrated Community Analysis Approach for Microbial Source Tracking in a Coastal Creek. *Environmental Science & Technology* 2011, 4.5, (17), 7195-7201; Jeong, J. Y.; Park, H. D.; Lee, K. H.; Weon, H. Y.; Ka, J. O., Microbial Community Analysis and Identification of Alternative Host-Specific Fecal Indicators in Fecal and River Water Samples Using Pyrosequencing. *Journal of Microbiology* 2011, 49, (4), 585-594). Sequence analysis of entire microbial communities creates an opportunity to discover a multitude to different bacterial species that are unique to fecal and environmental sources of FIB in recreational waters.

BRIEF SUMMARY OF THE INVENTION

The present invention provides methods and compositions for the identification of unique identifying sequences and taxa which can identify specific organism sources of contamination in environmental samples.

A method for detecting the source of fecal bacteria contamination in an environmental sample comprising the steps of (a) obtaining an environmental sample to be tested (b) determining the taxa of the fecal indicator bacteria present in said sample, if any, (c) determining if the taxa of the fecal indicator bacteria corresponds to the unique taxa set forth in Table 1 (bird), Table 2 (grazer) or Table 3 (sewage), wherein if a majority of the taxa are identified as present in said environmental sample, indicate that the sample has fecal contamination, and the source of said contamination is bird feces, grazer feces and/or sewage. The method, wherein if at least 51%, 50%, 45%, 40%, 35%, 30%, 25%, 20%, 15%, or 10% of the unique taxa in at least one of Table, 2 and/or 3 are determined to be present. Further, the method, wherein the step (b) determination of the taxa of the fecal indicator bacteria present in said sample is carried out by detection of taxa by microarray probe hybridization.

A set of taxa found in Table 1, wherein if at least 20% of the taxa are present, indicate the presence of bird feces. A set of taxa found in Table 2, wherein if at least 20% of the taxa are present, indicate the presence of grazer feces. A set of taxa found in Table 3, wherein if at least 20% of the taxa are present, indicate the presence of human feces and/or sewage.

BRIEF DESCRIPTION OF THE DRAWINGS

FIG. 2. Composition of OTUs detected in each fecal source. OTUs are shown that were detected in at least half of the samples for each source animal. Total number of OTUs is shown in parentheses and lists with taxonomic descriptions found in.

DETAILED DESCRIPTION OF THE PREFERRED EMBODIMENT

Introduction

Figure 1:
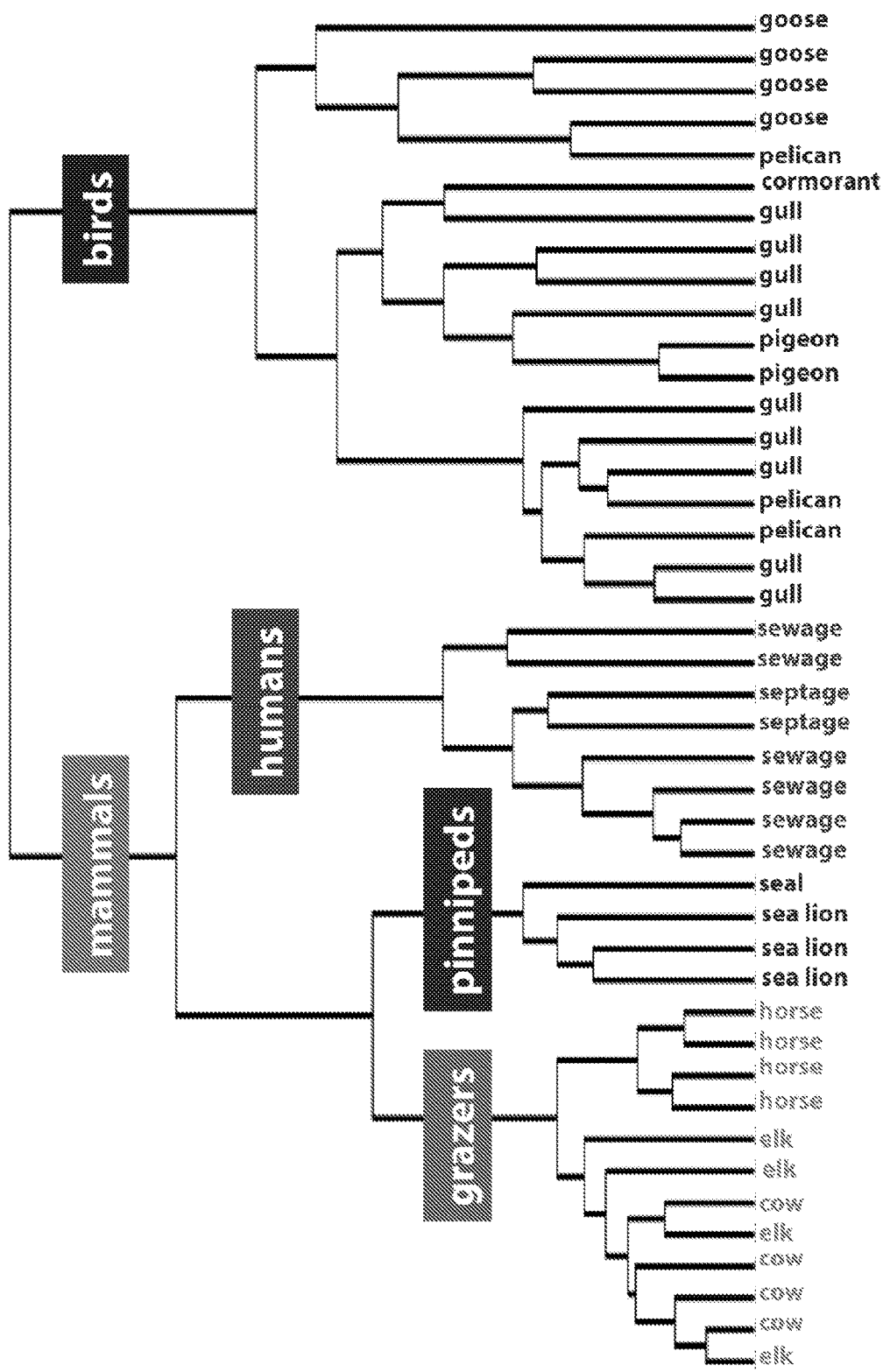
FIG. 1. Cluster analysis dendrogram of 16S rRNA gene composition showing similarity among microbial communities in fecal sources. Each sample represents a distinct animal population or sewage source and is a composite of individual fecal samples from the population.

Conventional methods for fecal source tracking typically use single biomarkers to systematically identify or exclude sources. High-throughput DNA sequence analysis can potentially identify all sources of microbial contaminants in a single test by measuring the total diversity of fecal microbial communities. In this study we used phylogenetic microarray analysis to determine the comprehensive suite of bacteria that define major sources of fecal contamination in coastal California. Fecal wastes were collected from 42 different populations of humans, birds, cows, horses, elk and pinnipeds. The bacterial community composition was characterized using a DNA microarray that probes for 16S rRNA genes of 59,316 different bacterial taxa. Cluster analysis revealed strong differences in community composition among fecal wastes from human, birds, pinnipeds and grazers. Actinobacteria, Bacilli and many Gammaproteobacteria taxa discriminated birds from mammalian sources. Diverse families within the Clostridia and Bacteroidetes taxa discriminated human wastes, grazers and pinnipeds from each other. We found 1058 different bacterial taxa that were unique to either human, grazing mammal, or bird fecal wastes. These OTUs can serve as specific identifier taxa for these sources in environmental waters. Two field tests in marine waters demonstrate the capacity of phylogenetic microarray analysis to track multiple sources with one test.

In this study we used a high-density oligonucleotide microarray to census the 16S rRNA gene diversity in different sources of fecal contamination. The microarray targets 59,316 different 16S rRNA gene polymorphisms that represent most known phyla of bacteria. We test the assumption that different avian and mammalian fecal sources can be distinguished on the basis of their bacterial community composition. We screened a variety of fecal sources of concern in coastal California to identify the microbial groups that are source-specific, and then used these unique taxa to detect influence from these sources in marine samples that exceeded water quality limits for fecal indicator bacteria.

DESCRIPTIONS OF THE EMBODIMENTS

Herein is described three sets of unique organism taxa. The taxa are identified and set forth in Tables 1, 2 and 3. In one embodiment, if a majority of the taxa are identified as present in an environmental sample, indicate that the sample or source of the sample is contaminated. In other embodiments, if at least 51%, 50%, 45%, 40%, 35%, 30%, 25%, 20%, 15%, or 10% of the unique taxa are detected as present in a sample, the present methods can establish that there is fecal contamination in the sample and the source of such fecal contamination can be identified. In other embodiments, combinations of the sequences in each set of taxa act like a fingerprint to identify and track particular types of fecal contamination from organisms such as bird, grazer, pinnipeds and humans.

Table 1 identifies unique taxa which indicate presence of bird feces contamination. Table 2 identifies unique taxa which indicate presence of grazer feces contamination. Table 3 identifies unique taxa which indicate presence of human feces and/or sewage contamination.

In one embodiment, method for use of specific probes and probe sets that we have determined to be an indicator of a particular fecal source. We have identified hundreds of probe sets and thousands of probes that can be used in combination to identify the source of the fecal input. Previous technology used a single region of DNA that is hypothesized to be specific to a specific source for identification. If bacteria with DNA sequences matching the single indicator test were not present at a detectable level the sample would erroneously be classified as free from that fecal source. Conversely, if a fecal microbial community contaminated a water system from a non-target source and contained an organism that would match the single indicator test it would be erroneously considered as a positive indication of the source from the single indicator. Using hundreds of indicator test greatly increases the confidence of a correct identification.

In another embodiment, the method comprises using an array to determine or detect presence of fecal indicator bacteria. An array approach using an array such as the PhyloChip microarray to source identification relies on the presence of dozens or hundreds of taxa, rather than one or a few taxa, to determine the occurrence of various fecal sources. In the sewage spill example presented in this study below, almost all human source identifier taxa were detected in water samples with high fecal indicator bacteria (FIB). These fecal bacteria were input from a large release of sewage directly into the tested waters, and subject to little aging and decay. This situation is in contrast to the non-point source situation at Campbell Cove where high FIB samples contained around 20% of the identifier taxa from a known fecal source (gull feces). Inputs of fecal bacteria at Campbell Cove were not necessarily direct into receiving waters but also from shoreline runoff and leaching through beach sands and sediments (Sonoma, Co., Final interim report for Bodega Bay-Campbell Cove tidal circulation study, water quality testing and source abatement measures project. In Services, H., Ed. Santa Rosa, Calif., 2004; p 14). As a result, fecal microbial communities were likely subject to more decay and modification before entering receiving waters compared to the sewage spill example.

Thus in some embodiments, if at least 20% to 50%, 60%, 70%, 75%, 80%, 85%, 90%, 95%, 96%, 97%, 98%, to 99% of the taxa in Tables 1, 2 and/or 3 are identified as present in an environmental sample, the sample or source of the sample is contaminated.

Application of the community identifier approach to source tracking will benefit from adjusting the analysis based on the expected persistence of different taxa. 16S rRNA gene composition is strongly source-specific and can be used to differentiate sources of fecal contamination in recreational waters. The use of an oligonucleotide microarray that targets the 16S rRNA gene pool of the bacterial community can serve as a rapid method for identifying the presence or absence of multiple sources of FIB with a single test. The measurement of all community 16S rRNA genes should not be necessary, however. The present examples show that several hundred targets per source type can be sufficient for source identification from the universal 16S rRNA gene pool.

The detection of the FIB taxa present can be carried out by any number of array hybridization systems, bead multiplex systems, PCR, or any other known detection system.

Other embodiments provide a method for selecting and/or utilizing a set of oligonucleotide probes for use in an analysis system or bead multiplex system for simultaneously detecting a plurality of organisms and taxa in a sample and determining a fecal indicator bacteria profile of the sample.

The oligonucleotide probes can each be from about 5 bp to about 100 bp, preferably from about 10 by to about 50 bp, more preferably from about 15 by to about 35 bp, even more preferably from about 20 bp to about 30 bp. In some embodiments, the probes may be 5-mers, 6-mers, 7-mers, 8-mers, 9-mers, 10-mers, 11-mers, 12-mers, 13-mers, 14-mers, 15-mers, 16-mers, 17-mers, 18-mers, 19-mers, 20-mers, 21-mers, 22-mers, 23-mers, 24-mers, 25-mers, 26-mers, 27-mers, 28-mers, 29-mers, 30-mers, 31-mers, 32-mers, 33-mers, 34-mers, 35-mers, 36-mers, 37-mers, 38-mers, 39-mers, 40-mers, 41-mers, 42-mers, 43-mers, 44-mers, 45-mers, 46-mers, 47-mers, 48-mers, 49-mers, 50-mers, 51-mers, 52-mers, 53-mers, 54-mers, 55-mers, 56-mers, 57-mers, 58-mers, 59-mers, 60-mers, 61-mers, 62-mers, 63-mers, 64-mers, 65-mers, 66-mers, 67-mers, 68-mers, 69-mers, 70-mers, 71-mers, 72-mers, 73-mers, 74-mers, 75-mers, 76-mers, 77-mers, 78-mers, 79-mers, 80-mers, 81-mers, 82-mers, 83-mers, 84-mers, 85-mers, 86-mers, 87-mers, 88-mers, 89-mers, 90-mers, 91-mers, 92-mers, 93-mers, 94-mers, 95-mers, 96-mers, 97-mers, 98-mers, 99-mers, 100-mers or combinations thereof.

In some embodiments, the chosen oligonucleotide probes can then be synthesized by any available method in the art. Some examples of suitable methods include printing with fine-pointed pins onto glass slides, photolithography using pre-made masks, photolithography using dynamic micro-mirror devices, ink-jet printing or electrochemistry. In one example, a photolithographic method can be used to directly synthesize the chosen oligonucleotide probes onto a surface. Suitable examples for the surface include glass, plastic, silicon and any other surface available in the art. In certain examples, the oligonucleotide probes can be synthesized on a glass surface at an approximate density of from about 1,000 probes per $\mu m^2$ to about 100,000 probes per $\mu m^2$, preferably from about 2000 probes per $\mu m^2$ to about 50,000 probes per $\mu m^2$, more preferably from about 5000 probes per $\mu m^2$ to about 20,000 probes per $\mu m^2$. In one example, the density of the probes is about 10,000 probes per $\mu m^2$. The array can then be arranged in any configuration, such as, for example, a square grid of rows and columns. Some areas of the array can be pathogen or organism identification or classification, and others can be used for image orientation, normalization controls or other analyses. In some embodiments, materials for fabricating the array can be obtained from Affymetrix, GE Healthcare (Little Chalfont, Buckinghamshire, United Kingdom), Agilent Technologies (Palo Alto, Calif.), or TessArae (Potomac Falls, Va.).

Methods for design of detector tiles, selection of primers, and configuration of multiplex amplification protocols for the assay are known in the art and also described in U.S. Pat. Nos. 7,979,446; 7,695,941; 7,668,664; and 7,623,997, all of which are hereby incorporated by reference in their entirety.

In one embodiment, the methods for designing suitable probes and methods of fabricating a system herein are as described in International application publication Nos. WO 2010/151842 and in WO 2011/046614, both hereby incorporated by reference in their entireties.

Some embodiments relate to a method of designing or fabricating an array system including identifying fecal indicator bacteria taxa sequences corresponding to a plurality of organisms of interest, selecting fragments of fecal bacterial taxa and other sequences unique to each organism and creating variant DNA fragments corresponding to the fragments of fecal indicator bacteria taxa and, optionally, the sequences unique to each organism and then fabricating the array system.

Non-limiting examples of arrays include microarrays, bead arrays, through-hole arrays, well arrays, and other arrays known in the art suitable for use in hybridizing probes to targets. Arrays can be arranged in any appropriate configuration, such as, for example, a grid of rows and columns. Some areas of an array comprise the detection probes whereas other areas can be used for image orientation, normalization controls, signal scaling, noise reduction processing, or other analyses. Control probes can be placed in any location in the array, including along the perimeter of the array, diagonally across the array, in alternating sections or randomly. In some embodiments, the control probes on the array comprise probe pairs of PM and MM probes. The number of control probes can vary, but typically the number of control probes on the array range from 1 to about 500,000. In some embodiments, at least 10, 100, 500, 1,000, 5,000, 10,000, 25,000, 50,000, 100,000, 250,000 or 500,000 control probes are present. When control probe pairs are used, the probe pairs will range from 1 to about 250,000 pairs. In some embodiments, at least 5, 50, 250, 500, 2,500, 5,000, 12,500, 25,000, 50,000, 125,000 or 250,000 control probe pairs are present. The arrays can have other components besides the probes, such as linkers attaching the probes to a support. In some embodiments, materials for fabricating the array can be obtained from Affymetrix (Santa Clara, Calif.), GE Healthcare (Little Chalfont, Buckinghamshire, United Kingdom) or Agilent Technologies (Palo Alto, Calif.).

In some embodiments, selected oligonucleotide probes are synthesized by any relevant method known in the art. Some examples of suitable methods include printing with fine-pointed pins onto glass slides, photolithography using pre-made masks, photolithography using dynamic micro-mirror devices, ink-jet printing, or electrochemistry. In one example, a photolithographic method can be used to directly synthesize the chosen oligonucleotide probes onto a surface. Suitable examples for the surface include glass, plastic, silicon and any other surface available in the art. In certain examples, the oligonucleotide probes can be synthesized on a glass surface at an approximate density from about 1,000 probes per $\mu m^2$ to about 100,000 probes per $\mu m^2$, preferably from about 2000 probes per $\mu m^2$ to about 50,000 probes per $\mu m^2$, more preferably from about 5000 probes per $\mu m^2$ to about 20,000 probes per $\mu m^2$. In one example, the density of the probes is about 10,000 probes per $\mu m^2$. The number of probes on the array can be quite large e.g., at least $10^5$, $10^6$, $10^7$, $10^8$ or $10^9$ probes per array.

Besides arrays where probes are attached to the array substrate, numerous other technologies may be employed in the disclosed system for the practice of the methods of the invention. In one embodiment, the probes are attached to beads that are then placed on an array as disclosed by Ng et al. (Ng et al. A spatially addressable bead-based biosensor for simple and rapid DNA detection. Biosensors & Bioelectronics, 23:803-810, 2008).

In another embodiment, probes are attached to beads or microspheres, the hybridization reactions are performed in solution, and then the beads are analyzed by flow cytometry, as exemplified by the Luminex multiplexed assay system, in this analysis system, homogeneous bead subsets, each with beads that are tagged or labeled with a plurality of identical probes, are combined to produce a pooled bead set that is hybridized with a sample and then analyzed in real time with flow cytometry, as disclosed in U.S. Pat. No. 6,524,793.

Bead subsets can be distinguished from each other by variations in the tags or labels, e.g., using variability in laser excitable dye content.

In a further embodiment, probes are attached to cylindrical glass microbeads as exemplified by the Illumina Veracode multiplexed assay system. Here, subsets of microbeads embedded with identical digital holographic elements are used to create unique subsets of probe-labeled microbeads. After hybridization, the microbeads are excited by laser light and the microbead code and probe label are read in real time multiplex assay.

In another embodiment, a solution based assay system is employed as exemplified by the NanoString nCounter Analysis System (Geiss G et al. Direct multiplexed measurement of gene expression with color-coded probe pairs. Nature Biotech. 26:317-325, 2008). With this methodology, a sample is mixed with a solution of reporter probes that recognize unique sequences and capture probes that allow the complexes formed between the nucleic acids in the sample and the reporter probes to be immobilized on a solid surface for data collection. Each reporter probe is color-coded and is detected through fluorescence.

In a further embodiment, branched DNA technology, as exemplified by Panomics QuantiGene Plex 2.0 assay system, is used. Branched DNA technology comprises a sandwich nucleic acid hybridization assay for RNA detection and quantification that amplifies the reporter signal rather than the sequence. By measuring the RNA at the sample source, the assay avoids variations or errors inherent to extraction and amplification of target polynucleotides. The QuantiGene Plex technology can be combined with multiplex bead based assay system such as the Luminex system described above to enable simultaneous quantification of multiple RNA targets directly from whole cells or purified RNA preparations.

In some embodiments, the array system uses multiple probes for increasing confidence of identification of a particular organism using a fecal indicator bacterial gene targeted high density microarray. The use of multiple probes can greatly increase the confidence level of a match to a particular fecal indicator bacteria. Also, in some embodiments, mismatch control probes corresponding to each perfect match probe can be used to further increase confidence of sequence-specific hybridization of a target to a probe. For example, probes with a mismatch at the $13^{th}$ nucleotide can be used to indicate non-specific binding and a likely non-match to the sequence of that probe at that nucleotide position.

Arrays and methods of making and using phylogenetic arrays, resequencing arrays and preparing samples are known in the art and are also described in U.S. Pat. Nos. 7,623,997; 7,668,664; 7,961,323; 7,979,446; U.S. Application Publication No. 20070212718 and 20110039710, and International Patent Pub. WO/2012/027302, all of which are hereby incorporated by reference in their entireties for all purposes, and also described in Wang, Z., Daum, L. T., Vora, G. J., Metzgar, D., Walter, E. A., Canas, L. C., Malanoski, A. P., Lin, B. and Stenger, D. A. (2006) Identifying Influenza Viruses with Resequencing Microarrays. Emerg Infect Dis, 12, 638-646; Lin, B., Wang, Z., Vora, G. J., Thornton, J. A., Schnur, J. M., Thach, D. C., Blaney, K. M., Ligler, A. G., Malanoski, A. P., Santiago, J. et al. (2006) Broad-spectrum respiratory tract pathogen identification using resequencing DNA microarrays. Genome Res. 16:527-535, and Davignon, L., Walter, E. A., Mueller, K. M., Barrozo, C. P., Stenger, D. A. and Lin, B. (2005) Use of resequencing oligonucleotide microarrays for identification of Streptococcus pyogenes and associated antibiotic resistance determinants. J Clin Microbiol, 43, 5690-5695; Wilson, W. J., Strout, C. L., DeSantis, T. Z., Stilwell, J. L., Carrano, A. V. and Andersen, G. L. (2002) Sequence-specific identification of 18 pathogenic microorganisms using microarray technology. Mol Cell Probes, 16, 119-127; Wilson, K. H., Wilson, W. J., Radosevich, J. L., DeSantis, T. Z., Viswanathan, V. S., Kuczmarski, T. A. and Andersen, G. L. (2002) High-density microarray of small-subunit ribosomal DNA probes. Appl Environ Microbiol, 68, 2535-2541; Zwick, M. E., McAfee, F., Cutler, D. J., Read, T. D., Ravel, J., Bowman, G. R., Galloway, D. R. and Mateczun, A. (2005) Microarray-based resequencing of multiple Bacillus anthracis isolates. Genome Biol, 6, R10; Wong, C. W., Albert, T. J., Vega, V, B., Norton, J. E., Cutler, D. J., Richmond, T. A., Stanton, L. W., Liu, E. T. and Miller, L. D. (2004) Tracking the evolution of the SARS coronavirus using high-throughput, high-density resequencing arrays. Genome Res, 14, 398-405; Sulaiman, I. M., Liu, X., Frace, M., Sulaiman, N., Olsen-Rasmussen, M., Neuhaus, E., Rota, P. A. and Wohlhueter, R. M. (2006) Evaluation of affymetrix severe acute respiratory syndrome resequencing GeneChips in characterization of the genomes of two strains of coronavirus infecting humans. Appl Environ Microbiol, 72, 207-211; and Hacia, J. G. (1999) Resequencing and mutational analysis using oligonucleotide microarrays. Nat Genet, 21, 42-47, all of which are hereby incorporated by reference for all purposes.

As used herein, a "sample" is from any source, including, but not limited to a biological sample, a gas sample, a fluid sample, a solid sample, or any mixture thereof.

In some embodiments, the samples used can be environmental samples from any environmental source, for example, naturally occurring or artificial atmosphere, water systems, soil or any other sample of interest. In some embodiments, the samples may be obtained from, for example, atmospheric pathogen collection systems, manufacturing plants involved in food preparation or handling, hospital or clinic exam rooms and surfaces, etc. In a preferred embodiment, the array system of the present embodiments can be used in any environment.

In other embodiments, the sample used with the array system can be any kind of clinical or medical sample. In one embodiment, the clinical sample comprises at least one of tissue, skin, stool, bodily fluid, or blood.

Further, the present invention is not limited to biological samples obtained from humans. The present invention may also be applied to biological samples obtained from any animal species including domestic and/or farm animals including, but not limited to: dogs, cats, horses, cows, pigs, goats, sheep, rabbits, mice, rats, etc. In addition, the present invention may also be applied to biological samples obtained from any animal species that may be found in the wild or traditionally thought of as zoological animals, for example: monkeys, giraffes, elephants, zebras, tigers, lions, lemurs, etc. Further, the present invention may also be applied to biological samples obtained from any avian species. In this embodiment it is understood that the gene targets embedded on the microarray chip to be detected would contain the genes for the respective species selected.

Further, the sample of the present invention is not limited to biological samples, the sample of the present invention may be environmental (air, water, soil, etc.), animal (see above), or plant (e.g., cells obtained from any portion of a plant where the species of plant is without limit). Again, in this embodiment it is understood that the gene targets embedded on the microarray chip to be detected would contain the genes for the respective species selected, when that species is known (i.e., animal or plant). Further, when the sample is environmental, the gene targets embedded on the microarray chip can be any predetermined collection that is used to detect and identify any pathogen or organism of interest, for example.

In some embodiments, the sample is a processed or unprocessed food product. In other aspects, the food sample comprises at least one of meat, turkey, chicken and other poultry, milk, eggs, eggs products, dairy products, fresh or dried fruits and vegetables and their juices, grains, fish, seafood, pet food, baby food and infant formula.

Other applications of the presently described system and array is the monitoring of organisms and fecal indicator bacteria in food and beverage production, animal husbandry, water supplies, or treated human waste that may be applied to agricultural land, etc.

Example 1

Fecal Sampling and Source of Contamination

In this study we used a high-density oligonucleotide microarray to census the 16S rRNA gene diversity in different sources of fecal contamination. The microarray targets 59,316 different 16S rRNA gene polymorphisms that represent most known phyla of bacteria. We test the assumption that different avian and mammalian fecal sources can be distinguished on the basis of their bacterial community composition. We screened a variety of fecal sources of concern in coastal California to identify the microbial groups that are source-specific, and then used these unique taxa to detect influence from these sources in marine samples that exceeded water quality limits for fecal indicator bacteria Feces sampling and DNA extraction. Human fecal wastes and freshly deposited droppings from animals were collected at numerous locations throughout California. Human fecal wastes included primary influent or effluent from eight different municipal wastewater treatment plants, leachate samples from two community septic tanks serving more than 30 households each, and one composite sample of 10 holding tanks from individual households. Sampled animal populations included cows (4), horses (4), tule elk (4), western and California gulls (9), Canada geese (4), pelican (3), pigeon (2), cormorant (1), sea lion (3), elephant seal (1). Each animal sample was a composite of droppings from at least five different individuals from one location and every replicate sample is from a unique population. Individual fecal samples were homogenized and immediately frozen upon collection. Samples were stored at −80° C. until DNA extraction.

Each fecal sample was extracted in triplicate to obtain genomic DNA from the microbial community. Two extraction methods were employed: a CTAB extraction method and a kit extraction. In the CTAB method, 0.5 g of homogenized fecal sample were added to a Lysing Matrix E tube (MP Biomedicals, Solon, Ohio), and 650 µL, TE buffer, 250 µL 10× phosphate buffered saline, and 100 µL 10% SDS were added. The tubes were bead-beat at 5.5 m/s for 25 s in a FastPrep-24 instrument (MP Biomedicals, Solon, Ohio), 5.5 m/s for 25 s, 10 µL of 20 mg/mL Proteinase K was added and tubes were incubated at 37° C. for 30 min. Following centrifugation at 10,000×g for 5 min, supernatant was transferred to 2 mL microcentrifuge tube and amended with 80 µL M NaCl and 80 µL 10% CTAB buffer solution. Tubes were heated at 65° C. for 10 min., 700 µL 24:1 chloroform: isopropanol added and then centrifuged at 6,000×g for 5 min. Supernatant was transferred to a clean microcentrifuge tube, amended with 0.8 volumes of isopropanol, gently mixed and incubated at −20° C. for 1 hr. Following centrifugation at 16,000×g 4° C. for 15 min the supernatant was discarded and the remaining extract washed with ice-cold 70% ethanol. Following centrifugation at 16,000×g at 4° C. for 5 min., the supernatant was discarded, the remaining DNA pellet was air dried and suspended in 30 µL elution buffer. The second DNA extraction method was conducted with the DNA EZ extraction kit (GeneRite, North Brunswick, N.J.) per manufacturer's instructions. We extracted a subset of samples with both methods and saw little difference in the measured community profiles, and we saw no similarity patterns in our final results that were explained by extraction method.

Water sampling and DNA extraction. Water monitoring samples were collected from the field at sites with known sources of contamination. One set of samples was collected during a 10-day period following a 720,000 gallon spill of primary effluent from the Sausalito-Marin City Sanitary District treatment plant in Sausalito, Calif. that occurred in February 2009. Samples were collected daily for three days following the onset of the spill, and then once more 10 days after the initial spill during an accidental rupture that occurred during the repair. Sample locations included eight onshore and offshore sites ranging from directly adjacent to the ruptured pipe at the plant to up to 1 km away from the spill origin. Water samples were collected in 1 L bottles and stored at 4° C. until laboratory processing (within 6 hours of collection). For FIB tests, 20 mL of water was subsampled for total coliforms and *E. coli* (Colilert, IDEXX Laboratories, Westbrook, Me.) and Enterococcus (Enterolert, IDEXX Laboratories). For DNA extraction, 250 mL×3 of each sample was vacuum filtered through Whatman Anodise membrane filters (47 mm dia., 0.2 µm pore size) and immediately frozen and stored at −80° C. until DNA extraction. DNA was extracted from filters using the DNA EZ kit per manufacturer's instructions.

Water samples were also collected in conjunction with the County of Sonoma as part of the State of California AB411 monitoring program at Campbell Cove, Bodega Bay. Samples were collected weekly throughout 2008-2009 in knee-deep water with IL sampling bottles and processed in the laboratory as described above. A subset of samples was analyzed based on FIB counts. The analysis focused on nine samples that exceeded 1-day concentration limits and an additional 10 samples scattered throughout the sampling period that fell below FIB limits.

Polymerase Chain Reaction The bacterial 16S rRNA gene was amplified from each sample using PCR with primers 27F (5'-AGAGTTTGATCCTGGCTCAG-3" (SEQ ID NO: 1)) and 1492R (5'-GGTTACCTTGTTACGACTT-3' (SEQ ID NO: 2)) for bacteria. Each PCR reaction contained 1×Ex Taq buffer (Takara Bio Inc., Japan), 0.025 units/µl Ex Tag polymerase, 0.8 mM dNTP mixture, 1.0 µg/µl BSA, and 200 pM each primer and 1 ng genomic DNA (gDNA) as template for fecal samples and 10 ng gDNA for water samples. Each sample was amplified in 8 replicate 25 µl reactions spanning a range of annealing temperatures. PCR conditions were 95° C. (3 min), followed by 30 cycles 95° C. (30 s), 48-58° C. (25 s), 72° C. (2 min), followed by a final extension 72° C. (10 min). Amplicons from each reaction were pooled for each sample, purified with the QIAquick PCR purification kit (Qiagen, Valencia, Calif.), and eluted in 50 µL elution buffer.

PhyloChip Assay Description and Analysis. A complete description of the PhyloChip design and analysis is available in the supplementary methods of Hazen et al., Deep-Sea Oil Plume Enriches indigenous Oil-Degrading Bacteria. *Science* 2010, 330, (6001), 204-208. The PhyloChip (Second Genome, San Bruno, Calif.) was designed to detect most 16S rRNA gene sequences that identify bacteria and archaea. The PhyloChip probes for 59,959 different bacterial and archaeal taxa that represent 147 phyla. 1,123 classes, 1, 219 orders and 1,464 families according to the placement of its member organisms in the taxonomic outline as maintained by Philip Hugenholtz. See Hugenholtz, P., Exploring prokaryotic diversity in the genomic era. *Genome Biology* 2002, 3, 1-8. The microarray includes 1,016,064 probe features, the majority of which target 16S rRNA gene sequences that are useful for differentiating taxa. Additional probes are for quality management, processing controls, image orientation, and normalization controls (Hazen, T. C., et al., Deep-Sea Oil Plume Enriches Indigenous Oil-Degrading Bacteria. *Science* 2010, 330, (6001), 204-208).

PhyloChip Assay Analysis. For PhyloChip hybridization, we used 500 ng of bacterial PCR product for each microarray. PCR products were fragmented with DNAse 1 to a range of 50-200 bp as verified by agarose gels. Commercial kits were utilized for DNA preparation: Affymetrix (Santa Clara, Calif.) WT Double Stranded DNA Terminal Labeling, and Affymetrix GeneChip Hybridization, Wash, and Stain kits were used for PhyloChip analysis. Briefly, fragmented 16S amplicons and non-16S quantitative amplicon reference controls were labeled with biotin in 40 µL reactions containing: 8 µL of 5×TDF buffer, 40 units of TDF, 3.32 nanomoles of GeneChip labeling reagent. After incubating at 37° C. for 60 min, 2 µL of 0.5M EDTA was added to terminate the reaction, Labeled DNA was combined with 65 µL of 2×MES hybridization buffer, 20.4 µL of DMSO, 2 µL of Affymetrix control oligo B2, and 0.4 µL nuclease free water. Each reaction mixture was injected into the hybridization chamber of an array cartridge and incubated for 16 h in an Affymetrix hybridization oven at 48° C. and 60 RPM. Hybridization solution was removed and the microarrays were stained and scanned according to the manufacturers instructions.

Analysis procedures for fluorescent image files are described in detail in the supplemental material of Hazen et al., Deep-Sea Oil Plume Enriches Indigenous Oil-Degrading Bacteria. *Science* 2010, 330, (6001), 204-208. Briefly, each individual array feature occupied approximately 8×8 pixels in the image file corresponding to a single probe 25mer on the surface. Probe intensities were background-subtracted and scaled to quantitative standards (non-16S rRNA gene spike-ins) as previously described in DeSantis, T. Z.; Brodie, E. L.; Moberg, J. P.; Zubieta, I. X.; Piceno, Y. M.; Andersen, G. L., High-density universal 16S rRNA microarray analysis reveals broader diversity than typical clone library when sampling the environment, *Microbial Ecology* 2007, 53, 371-383. Presence/absence calling of each microbial taxon (operational taxonomic unit—OTU) was based on positive hybridization of multiple probes that correspond to an OTU (average of 37 probes/(OTU). Differences in mean hybridization intensity (fluorescence) of an OTU probe set among different PhyloChips reflected differences in the relative abundance of the OTU (DeSantis, T. Z.; Brodie, E. L.; Moberg, J. P.; Zubieta, I. X.; Piceno, Y. M.; Andersen, G. L., High-density universal 16S rRNA microarray analysis reveals broader diversity than typical clone library when sampling the environment *Microbial Ecology* 2007, 53, 371-383). The PhyloChip data used in this study are available for download at the GREENGENES website (greengenes.lbl.gov/Download/Microarrray_Data/).

PhyloChip results are output as lists of detected OTUs and their hybridization scores, with associated taxonomic information and references to represented sequences in public 16S rRNA gene repositories (greengenes.lbl.gov). Hybridization results were reduced to a community profile from each PhyloChip assay to a format useful for multivariate statistics consisting of log transformed hybridization intensity values for all detected OTUs. Inter-profile dissimilarity was calculated with the Bray-Curtis metric, and the resulting distance matrix was analyzed with hierarchical cluster analysis and non-metric multidimensional scaling (NMDS) ordination using the Primer v.6.1.13 statistical package. Analysis of Similarity (ANOSIM) was used to test the significance of differences in community composition among sample groups.

Determination of source identifier taxa. Source identifier taxa were defined as individual OTUs that were detected in a single source type, but never detected in any samples from other sources. The criteria for identifier bacteria selection were as follows: Identifier bacteria for animal sources needed to be unique to a single animal type and present in at least three distinct populations. Identifier bacteria for human sources needed to be present in at least 7 of 8 samples. More stringent requirements were selected for human sources because a greater number of bacterial taxa were detected in human sources than animal sources, likely due to overrepresentation of human-specific bacteria in the 16S rRNA gene database from human micro sequencing projects.

Source identification in environmental water samples. Application of PhyloChip for source identification in marine waters was tested in two field scenarios with known sources of human and avian contamination. The first was a monitoring study of a 765,000-gallon spill that occurred in Richardson Bay, an arm of San Francisco Bay, off the coast of Sausalito, Calif. in February 2009. The PhyloChip was used to determine which bacterial taxa significantly increased in relative abundance in samples with high FIB counts, and whether these enriched bacteria included the expected human identifier bacteria described above. To determine which taxa were specifically associated with high FIB counts, water samples with FIB concentrations that exceeded any 30-day geometric mean concentration limit were compared to samples that fell below all FIB concentration limits. Baseline microbial communities were defined by mean abundance of taxa in low FIB samples. Taxa whose relative abundance significantly exceeded baseline (>mean+ 2Γ) were determined in high FIB samples. The presence of source identifier bacteria in this enriched subset was used to determine the association between fecal sources and FIB exceedances. Results are reported as the percent of expected identifier taxa that were detected in each sample. The expected number of identifier taxa for a given source was defined as the average number of source-specific identifier taxa detected in individual populations of that source. A positive signal for source detection was defined as >20% enrichment of expected identifier taxa in a sample. Significant association between the detection of each source type and high FIB exceedances (Enterococcus above regulatory limit) was tested with contingency analysis (IMP 7.0.1).

The second field test occurred at Campbell Cove in Bodega Bay, Calif., a recreational beach that frequently exceeds FIB water quality limits. Contamination at this beach is not from human sources and is likely due to gull feces (Sonoma, Co., Final interim report for Bodega Bay- Campbell Cove tidal circulation study, water quality testing and source abatement measures project. In Services, H., Ed. Santa Rosa, Calif., 2004; p 14). We collected weekly monitoring samples over a 1-year period at this beach in conjunction with the county as part of the California Clean Beaches Initiative, Samples were split for both routine FIB testing and filtration for subsequent PhyloChip analysis. The analysis approach was similar to the sewage spill monitoring described above in which low FIB samples were analyzed at each site to establish the mean abundance and variance of each OTU under baseline (non-exceedance) conditions, and association between the enrichment of source identifier taxa and high FIB counts was tested with contingency analysis.

Fecal source microbial communities. A total of 20,368 bacterial OTUs were detected across all fecal samples. Samples clustered by source type indicating fecal bacterial communities of the same type of source animal were more similar to each other than to those of other sources (FIG. 1). The deepest branching clusters separated all mammalian sources from avian sources, indicating that microbial community composition is a distinctive characteristic of these two classes of vertebrates. Within the mammals, samples clustered into three distinct groups comprised of grazing animals (cows, elk, horses), human wastes and pinnipeds (FIG. 1). Grazing mammals were further partitioned into two clusters comprising ruminants (cow, elk) and horses. Geese formed a distinct cluster within the birds. There was no obvious clustering among the other bird types (gulls, pelicans, pigeons, cormorants), and clustering patterns among these birds were not related to geography. All sources contained taxonomic groups that encompass *E. coli* and *Enterococcus* that are used as regulatory fecal indicators.

Figure 2:
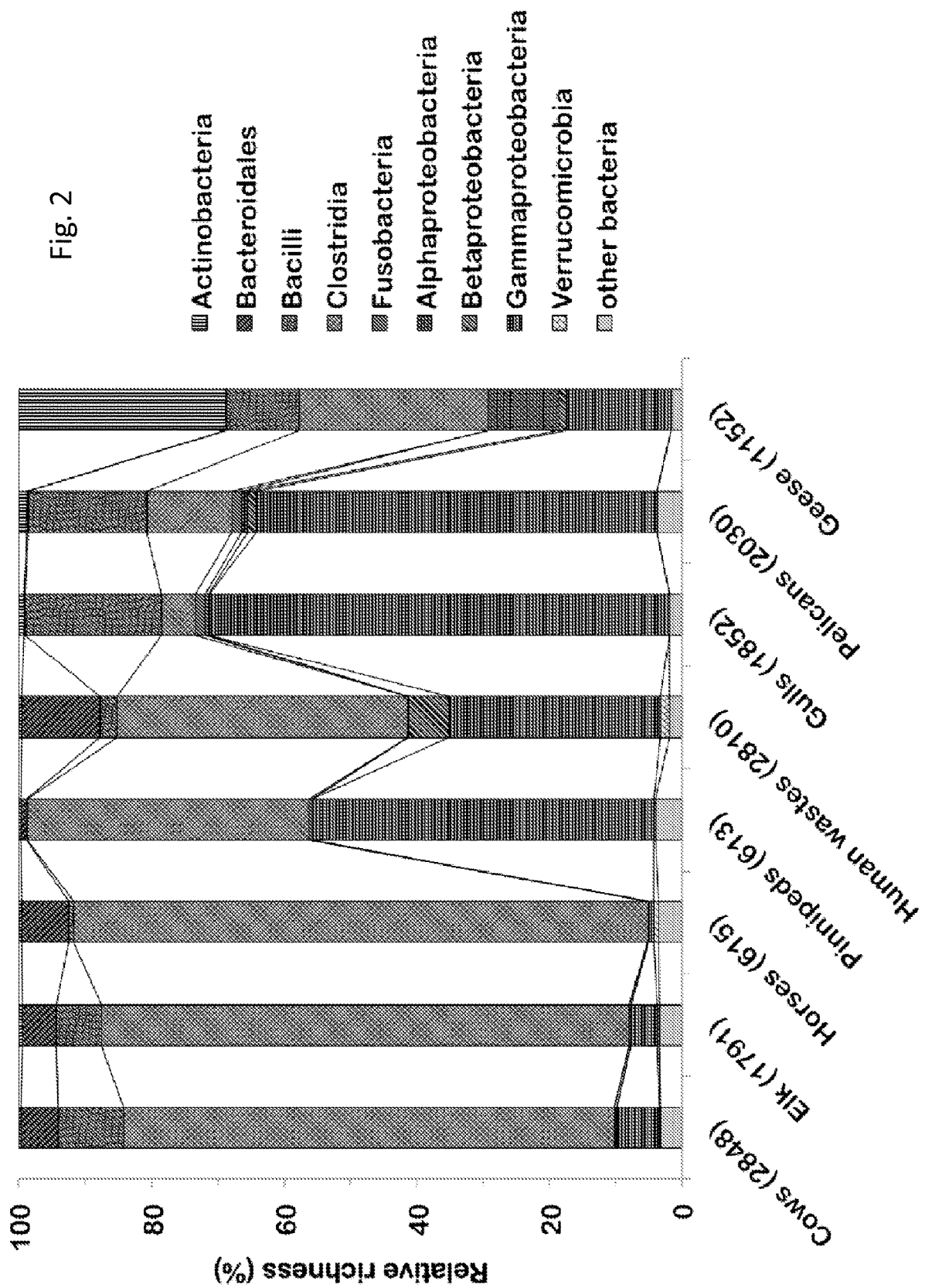

Clostridia dominated the taxonomic (OTU) richness of the fecal bacteria in mammalian fecal sources (FIG. 2). The remainder of taxonomic diversity in mammals was comprised of mainly Bacteroidales, Gammaproteobacteria and Bacilli. These results are consistent with previous surveys of other mammalian gut microbial communities (Lee, J. E.; Lee, S.; Sung, J; Ko, G., Analysis of human and animal fecal microbiota for microbial source tracking. *The ISME journal* 2011, 5, (2), 362-5, Unno, T.; Jang, J.; Han, D.; Kim, J. H.; Sadowsky, M. J.; Kim, O. S.; Chun, J.; Hur, H. G., Use of Barcoded Pyrosequencing and Shared OTUs To Determine Sources of Fecal Bacteria in Watersheds. *Environmental Science & Technology* 2010, 44, (20), 7777-7782; Ley, R. E.; Hamady, M.; Lozupone, C.; Turnbaugh, P. J.; Ramey, R. R.; Bircher, J. S.; Schlegel., M. L.; Tucker, T. A.; Schrenzel, M. D.; Knight, R.; Gordon, J. I., Evolution of mammals and their gut microbes. *Science* 2008, 320, (5883), 1647-1651). In contrast to mammals, avian feces contained far less taxa in the Clostridia and Bacteroidales and instead were dominated by Gammaproteobacteria and Bacilli (FIG. 2).

Analysis of avian fecal samples revealed that seabirds and pigeons had similar composition of bacteria and were dominated by Gammaproteobacteria (mostly Enterobacteria) and Bacilli (mostly Lactobacillales) (FIG. 2). Fecal communities in these birds were also characterized by the presence of Fusobacteriaceae OTUs that were generally absent from mammalian and geese communities. Taxonomic composition in geese was distinct from other types of birds and contained greater numbers of taxa in the Actinobacteria, Alphaprotecbacteria and Clostridia. Geese differ from other birds in this study because of their unique diet and digestive system. Geese consume high-fiber feed, such as grass, and contain a well-developed cecum that facilitates their breakdown in the large intestine (Clench, M. H.; Mathias, J. R., The avian cecum—a review. *Wilson Bulletin* 1995, 107, (1), 93-121). This more rumen-like digestive system facilitates the activity of fermentative Clostridia (Wang, Z. Y.; Shi, S. R.; Xu, M. J.; Yang, H. M., 16S rRNA-based analysis of bacterial diversity in the microbial flora of the goose intestinal tract. *Journal of Animal and Feed Sciences* 2009, 18, (3), 531-540). Canada geese often forage for plants and insects in the soil, and consequently ingest bacteria that are resident in soil or on plant surfaces, which may explain the prominence of Actinobacteria and Alphaproteobacteria in their feces. Despite these differences between geese and other birds, geese bacterial communities were more similar to other types of birds than they were to any mammalian fecal sources (FIG. 1).

Within the mammals, a variety of Clostridia, Bacilli and Bacteroidetes dominated taxonomic (OTU) richness of grazing mammals (FIG. 2). These bacteria are known to digest cellulose and other plant polysaccharides in the ruminant gut. Clostridia, Gammaproteobacteria (mostly coliforms) and Bacteroidetes dominated taxonomic richness of human wastes (FIG. 2). Human wastes were further distinguished by the presence of several Betaproteobacteria and Verrucomicrobia. Clostridia and Gammaproteobacteria dominated the taxonomic richness of pinnipeds.

Based on similarities in community composition (FIG. 1), the data were partitioned into four major groups for identifier bacteria analysis: human wastes, birds, grazers and pinnipeds. Source identifier taxa were defined as individual OTUs that were detected in a single source type, but never detected in any samples from other sources. The number of OTUs that met criteria for selection as source identifier taxa was 304 for birds, 213 for grazers, 0 for pinnipeds, and 541 for human wastes (FIG. 3).

Figure 3A:
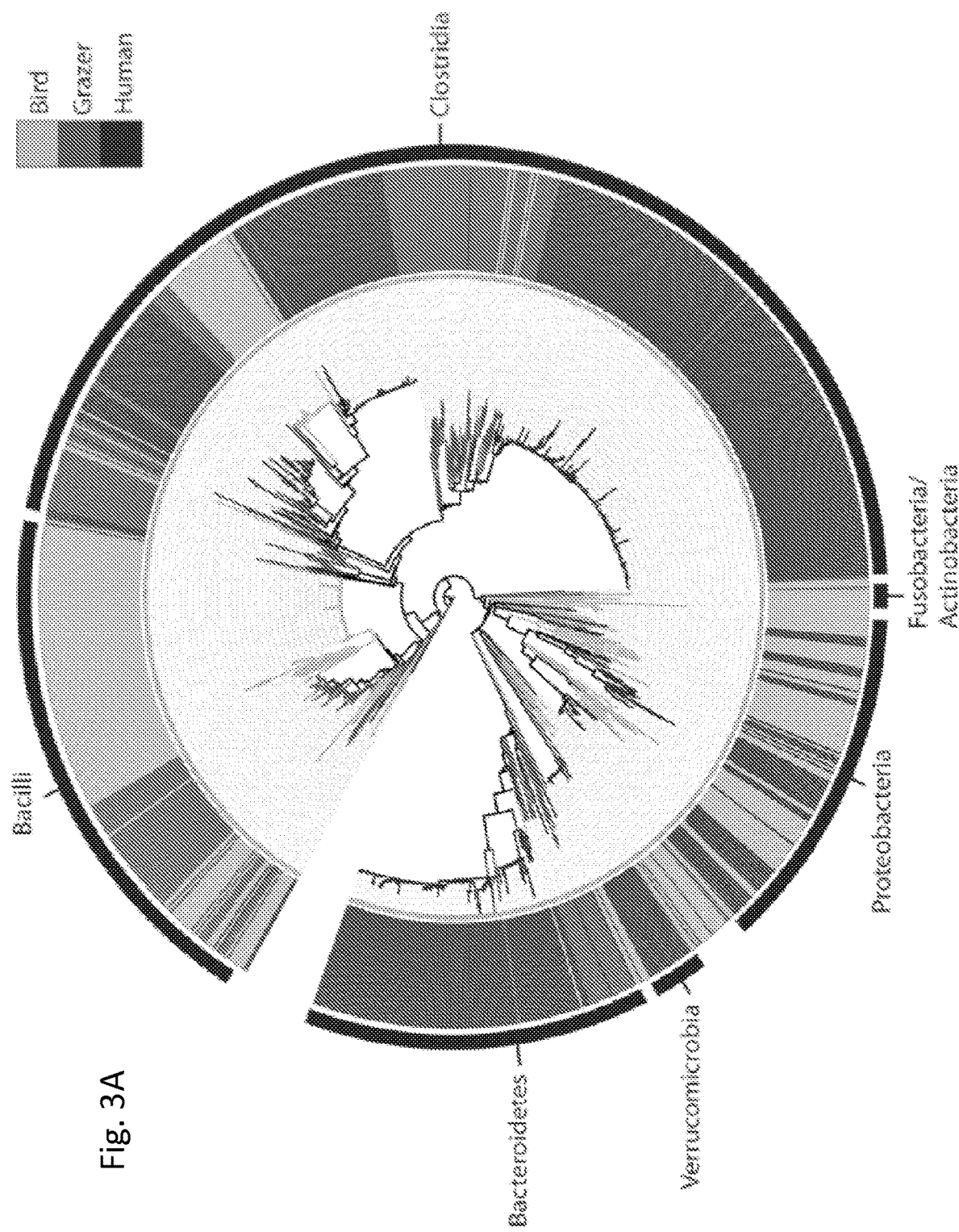
FIGS. 3A-B. Phylogenetic tree (FIG. 3A) and taxonomic composition (FIG. 3B) of source identifier OTUs for human wastes, birds and grazers. The phylogenetic tree was constructed from using full-length 16S rRNA gene sequences of representative taxa in each OTU using the approximately maximum likelihood algorithm implemented in FastTree (Price, M. N.; Dehal, P. S.; Arkin, A. P., FastTree 2-Approximately Maximum-Likelihood Trees for Large Alignments, *PLoS One* 2010, 5, (3), Article No.: e9490), and the tree was displayed using the Interactive Tree of Life tool (Letunic, I.; Bork, P., Interactive Tree Of Life (iTOL): an online tool for phylogenetic tree display and annotation. *Bioinformatics* 2007, 23, (1), 127-128). The outer bar of the phylogenetic tree (a) represents major bacterial phyla, the next bar is proportional to the number of OTUs for each of the 1053 source identifier OTUs, and the inner circle represents the phylogenetic placement for each OTU with branch lengths proportional to change in 16S rRNA gene sequence. Detailed taxonomic description and reference sequence information for each source identifier OTU is provided in Supplemental Tables 1-3.
Figure 3B:
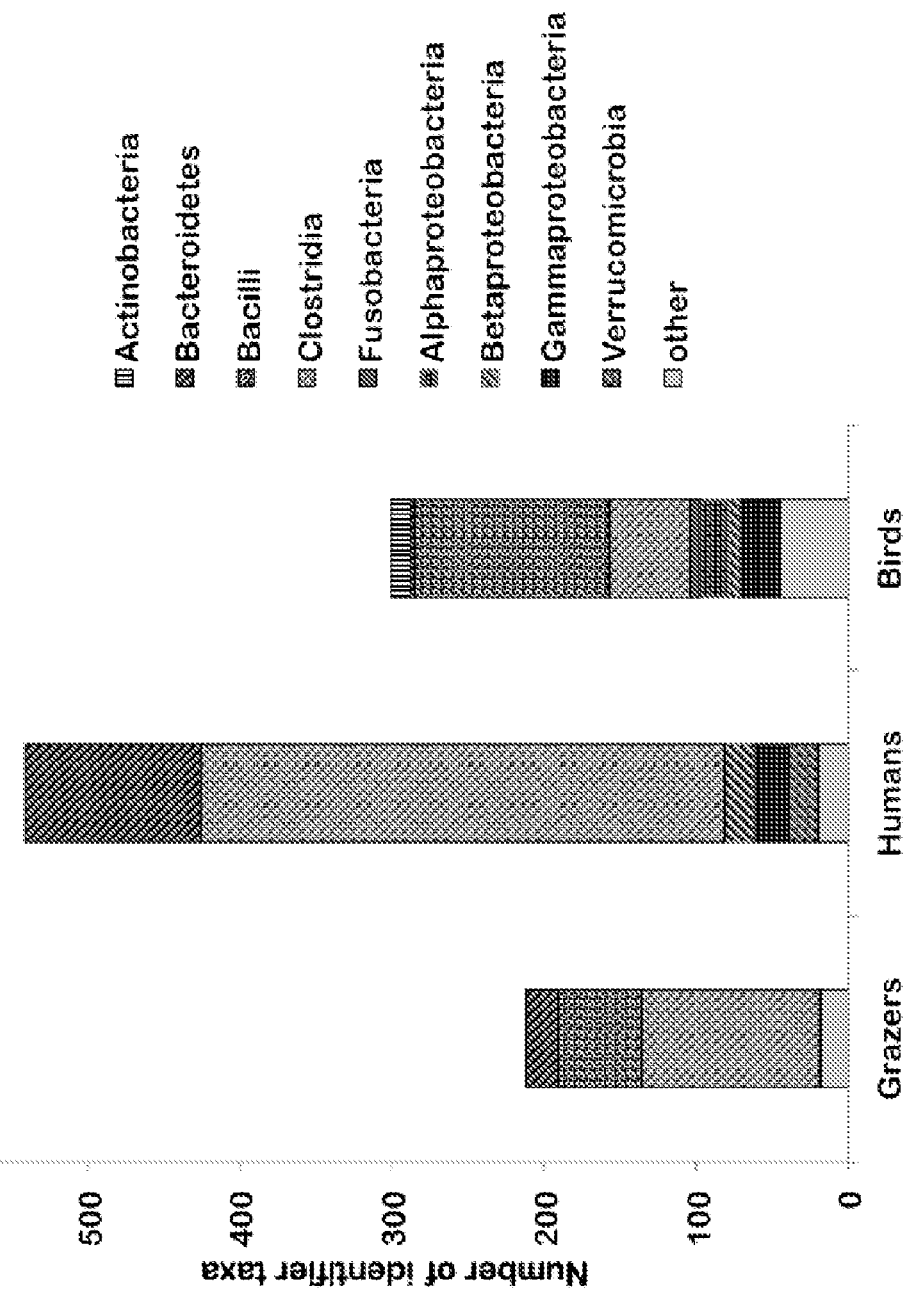

Human identifier bacteria were primarily Bacteroidaceae and Clostridiales OTUs that matched known human fecal bacteria 16S rRNA gene sequences (FIG. 3). Human Clostridiales OTUs were mainly found in the families Eubacterium, Faecalibacterium and Ruminococcus. Verrucomicrobia in the family Akkermansia were also indicative of human wastes, and are known to be mucin degraders in the human GI tract.

Bird identifier taxa included several different groups of Bacilli, mainly Lactobacillales and Staphylococcaceae FIG. 3). In addition, bird identifier bacteria included one unclassified family in the Clostridiales, as well as Enterobacteriaceae and Fusobacteriaceae. Bacteroidetes are a minor component in avian microbial communities (Lu, J. R.; Santo Domingo, J. W.; Lamendella, R.; Edge, T.; Hill, S., Phylogenetic diversity and molecular detection of bacteria in gull feces. *Applied and Environmental Microbiology* 2008, 74, (13), 3969-3976). We found several Lactobacilli OTUs that are included in the same subfamily as *Catellicoccus marimammalium* and that are closely related to *Enterococcaceae*. Lu et al., in Phylogenetic diversity and molecular detection of bacteria in gull feces. *Applied and Environmental Microbiology* 2008, 74, (13), 3969-3976, found gull feces were dominated by Bacilli (37% sequences), most of which were closely related to *Catellicoccus marimammalium*.

Grazer identifier taxa included a variety of Clostridia, many of which are known from cattle rumen, consisting of Clostridium, Ruminococcus, unclassified Clostridiales, RF6, RF30, RF39 and SHA-32 (FIG. 3). In addition, grazer identifiers included several Bacilli taxa found in the Planococcaceae, and Bacteroidales taxa that were distinct from those found in human wastes (FIG. 3).

Pinniped microbial communities were distinct from other fecal sources, but all OTUs found in at least three pinniped samples were also found in at least one other human or animal sample. For this reason, this study did not generate identifier taxa for pinnipeds due to the potential for cross-reactivity.

Figure 4:
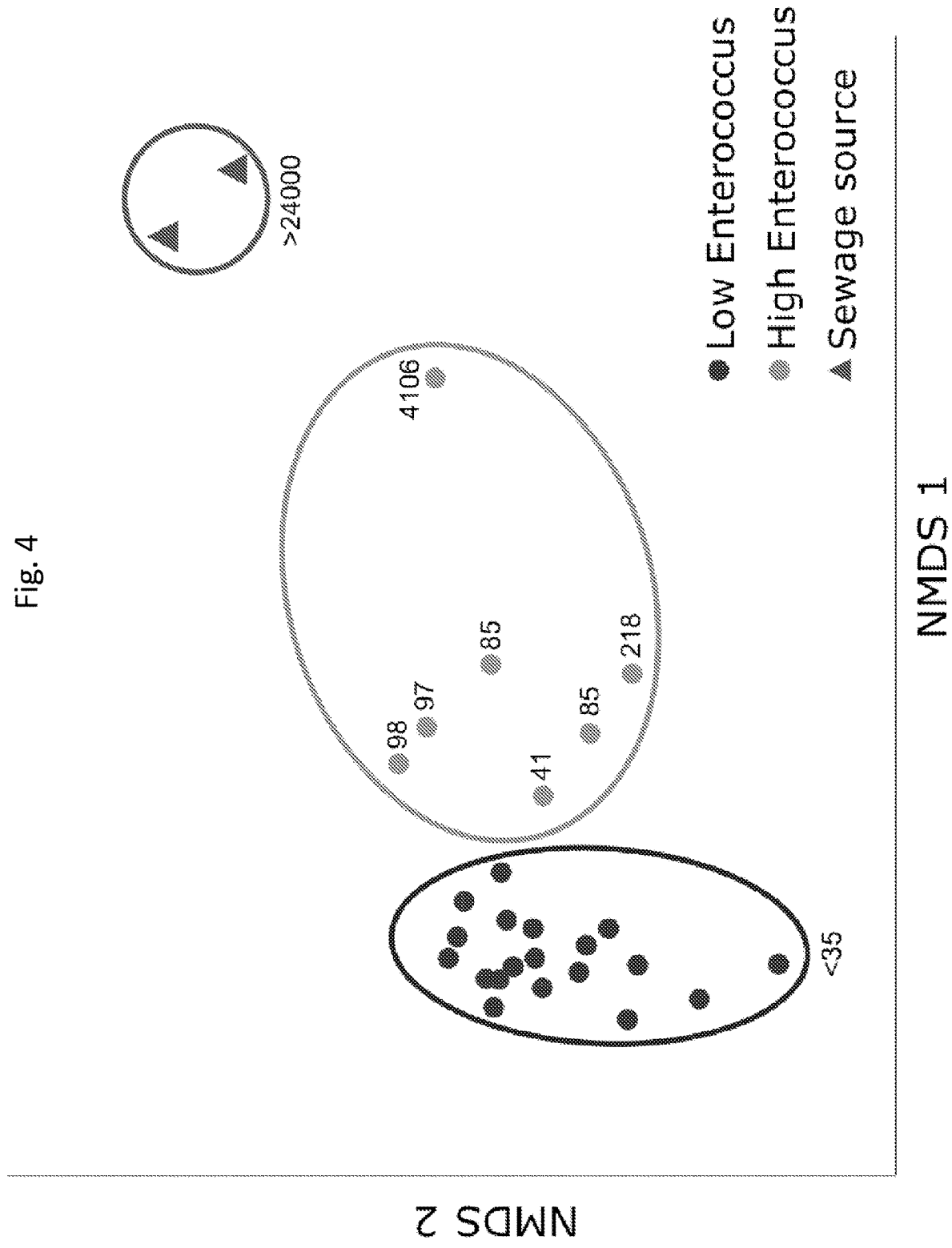
FIG. 4. Microbial community analysis of 28 water and two sewage samples collected during the 2009 sewage spill from the Sausalito Marin-City Sanitary District treatment plant. Ordination was conducted using non-metric multidimensional scaling with the Bray-Curtis distance metric. Numerical values are *Enterococcus* counts (MPN/mL) of individual samples. Microbial community composition in water samples that exceeded regulatory limits for Enterococcus (>35 MPN/mL) was significantly different than in samples with low Enterococcus counts (ANOSIM; P<0.05).
Figure 5:
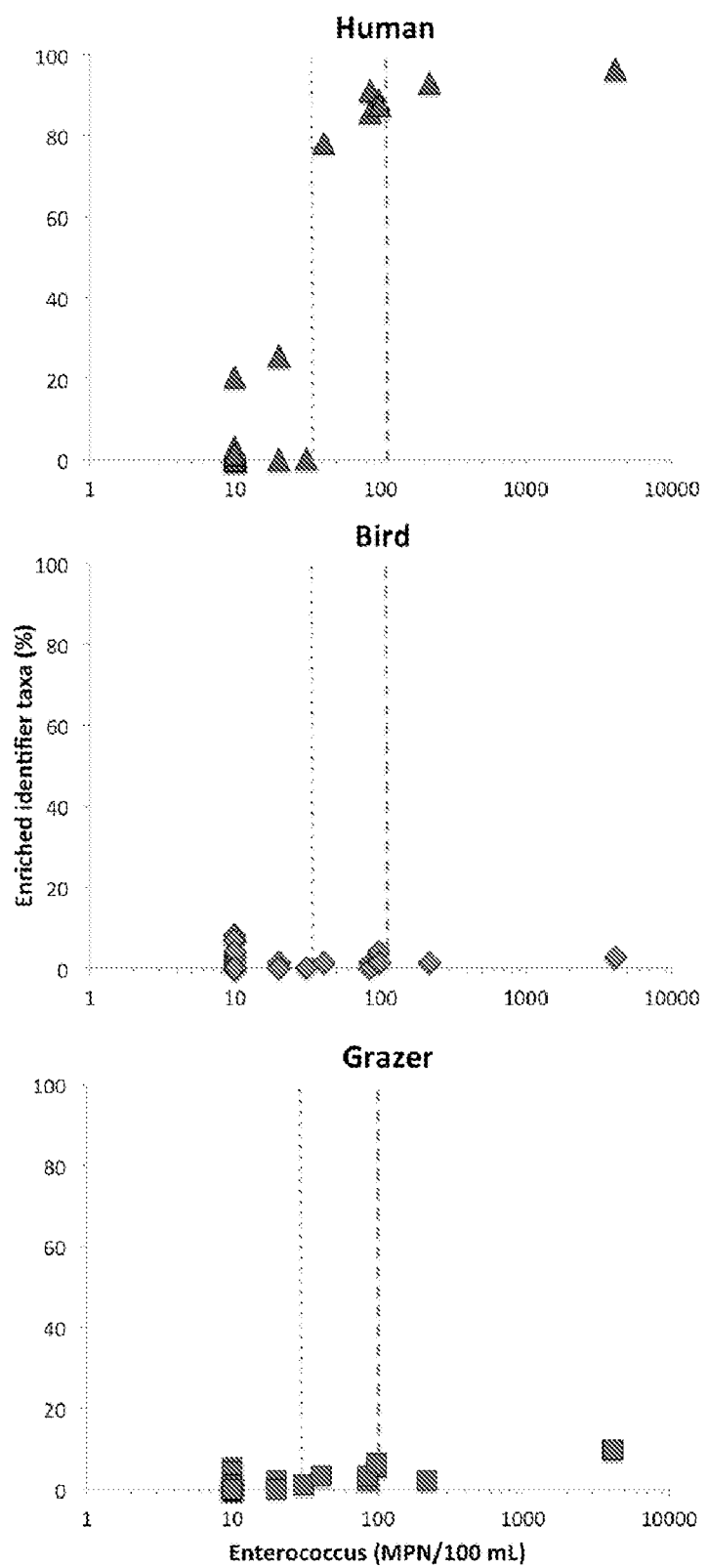
FIG. 5. Source identification in San Francisco Bay water samples collected during sewage spill monitoring (N=28). Results from Enterococcus FIB tests are plotted against the percent of source-identifier taxa that were significantly enriched above background (low FIB) conditions. High and low dashed lines show the single-day Enterococcus concentration limit and 30-day geometric mean limits, respectively. Higher than expected numbers of high *enterococcus* samples were enriched in human identifier taxa (P<0,001) but not bird or grazer identifier taxa (P>0.05).

Source identification field tests. Application of PhyloChip for source identification in marine waters was tested in two field scenarios with defined sources of human and avian contamination. The first test looked investigated microbial communities in Richardson Bay waters adjacent to a large sewage spill. Out of 26 water samples collected during the spill, two exceeded the 1-day Enterococcus concentration limit for marine water (104 MPN/mL) and an additional five exceeded the 30-day geometric mean limit (35 MPN/mL). These exceedance samples had significantly different microbial community compositions than samples that fell below FIB limits (FIG. 4). All samples that were above Enterococcus limits contained most (78-96%) of the expected fecal identifier bacteria for human fecal wastes (FIG. 5). I n contrast, there was little enrichment of bird or grazer identifier bacteria (0-10%) in samples with high Enterococcus counts. Contingency analysis showed greater than expected numbers of samples with enrichment in human identifier taxa (>20% identifiers enriched) in high *enterococcus* samples (P<0.001) but insignificant enrichment of grazer or bird identifier taxa (P>0.05). The results show the PhyloChip analysis is sensitive to human fecal signal in marine waters.

Figure 6:
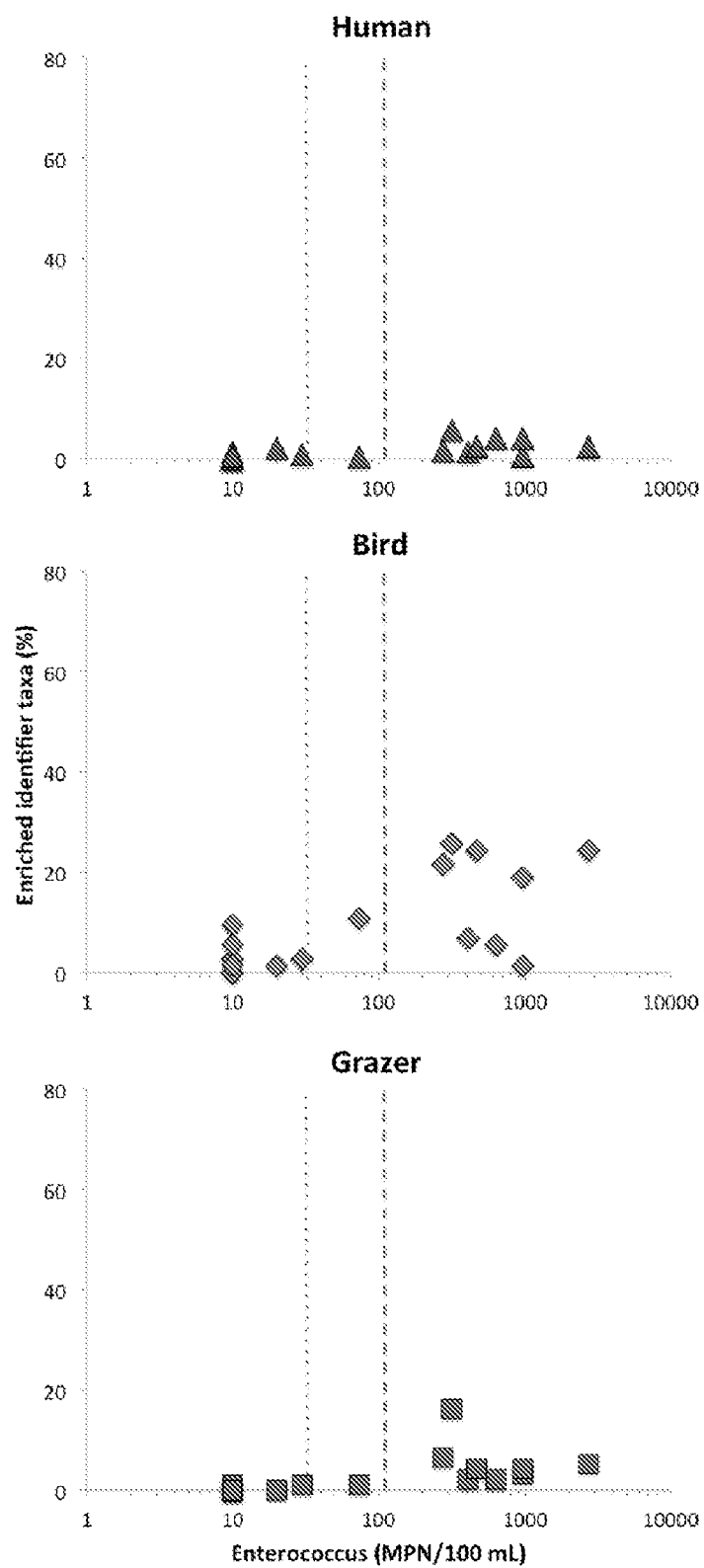
FIG. 6. Source identification at Campbell Cove, Bodega Bay (N=19). Results from Enterococcus FIB tests are plotted against the percent of source-identifier taxa that were significantly enriched above background (low FIB) conditions. High and low dashed lines show the single-day Enterococcus concentration limit and 30-day geometric mean limits, respectively, Higher than expected numbers of high *enterococcus* samples were enriched in bird identifier taxa (P=0.033) but not human or grazer identifier taxa (P>0.05).

The second field test was conducted along the beach of Campbell Cove in Bodega Bay, a site where a previous source tracking investigation found no evidence of human fecal contamination (Sonoma, C. o., Final interim report for Bodega Bay-Campbell Cove tidal circulation study, water quality testing and source abatement measures project. In Services, H., Ed. Santa Rosa, Calif., 2004; p 14). We analyzed a total of nine samples with high *enterococcus* counts (>35 MPN/mL) and eleven non-exceedance samples collected over the course of one year. An average of 1093 out of 6046 detected OTUs were significantly enriched over baseline relative abundances in high *enterococcus* samples. Several samples with high *enterococcus* had significant enrichment of identifier bacteria associated with bird feces (FIG. 6). Contingency analysis showed greater than expected numbers of samples with enrichment in bird identifier taxa (>20% identifiers enriched) in high *enterococcus* samples (P=0.033). Neither human nor grazer fecal identifiers were significantly enriched when *enterococcus* counts were high (P>0.05). From these results we conclude that birds and not human or grazer fecal inputs were associated with high *enterococcus* counts at Campbell Cove. These results are consistent with the findings of the previous source tracking investigation at this site that used *E. coli* ribotyping to determine gulls and not humans were a fecal source (Sonoma, Co., Final interim report for Bodega Bay-Campbell Cove tidal circulation study, water quality testing and source abatement measures project. In Services, H., Ed. Santa Rosa, Calif., 2004; p 14). We also found four high *enterococcus* samples at Campbell Cove with negligible enrichment in any source identifier taxa indicating additional sources of FIB that were not tested. Further investigation of the phylogenetic inventory of all bacterial taxa from this site, not just fecal identifiers, could help reveal additional fecal or environmental sources of FIB.

The phylogenetic microarray approach to source identification uses simultaneous occurrence of many diverse taxa to determine to detect fecal sources, Future work needs to address how fate and transport influences detection rates of these different taxa once they enter the environment. In the sewage spill example presented in this study, almost all human source identifier taxa were detected in water samples with high FIB. These fecal bacteria were input from a large release of sewage directly into the tested waters, and subject to little aging and decay. This situation is in contrast to the non-point source situation at Campbell Cove where high FIB samples contained around 20% of the identifier taxa from a known fecal source (gull feces). Inputs of fecal bacteria at Campbell Cove were not necessarily direct into receiving waters but also from shoreline runoff and leaching through beach sands and sediments (Sonoma, C, o., Final interim report for Bodega Bay-Campbell Cove tidal circulation study, water quality testing and source abatement measures project. In Services, H., Ed. Santa Rosa, Calif., 2004; p 14). As a result, fecal microbial communities were subject to more modification before entering receiving waters compared to direct inputs by the sewage spill. Application of the community identifier approach to source tracking will benefit from adjusting the analysis based on the expected persistence of different taxa.

There are potential advantages and limitations to using a phylogenetic microarray for source identification. An advantage is sensitive detection of taxa with low abundance in the community (DeSantis, T. Z.; Brodie, E. L.; Moberg, J. P.; Zubieta, I. X.; Piceno, Y. M.; Andersen, G. L., High-density universal 16S rRNA microarray analysis reveals broader diversity than typical clone library when sampling the environment. *Microbial Ecology* 2007, 53, 371-383). As fecal sources are diluted in receiving waters, taxa that are critical for source identification will decrease in relative abundance as they mix with the complex microbial background of the environment. The microarray probes for target sequences from the entire sample of PCR amplicons, and this amplicon pool consists of many billions of 16S rRNA gene sequences. 1-hybridization the entire pool amplified sequences may offer an advantage over pyrosequencing or other types of next generation sequencing because these methods randomly sequence a relatively small fraction of the amplified PCR product and consequently are not reliable for detecting less abundant members of the community that may be critical for source identification (Zhou, J. Z.; Wu, L. Y.; Deng, Y.; Zhi, X. Y.; Jiang, Y. H.; Tu, Q. C.; Xie, J. P.; Van Nostrand, J. D.; He, Z. L.; Yang, Y. F., Reproducibility and quantitation of amplicon sequencing-based detection. *Isme Journal* 2011, 5, (8), 1303-1313).

A limitation in applying phylogenetic microarrays to MST may be the insufficient number of probes for sources that are underrepresented in 16S rRNA gene databases. For example, few studies have surveyed microbial diversity in pinnipeds, and as a likely consequence we found no unique taxa in pinnipeds using the PhyloChip. More thorough assessments of sequence composition in some source types will be needed to find additional host-specific targets. In addition, cost and complexity can be barriers to widespread adaptation of this technology' in its current form. Measuring the full range of 16S rRNA gene sequences in the microbial community is not necessary, however, and a down-selected microarray that targets only the subset of microorganisms that is useful for source identification would simplify analysis and reduce cost.

The results of this study show that 16S rRNA gene composition of the bacterial community can be used to discriminate sources of fecal contamination. Differences in the diversity among fecal sources reveal hundreds of unique taxa that are specific to human, bird and grazer feces. Several different phylogenetic lineages, most of which are not considered in existing MST assays, differentiate these sources and are mainly found in the Clostridia, Bacilli and Bacteroidetes. Comprehensive interrogation of microbial communities for these diverse identifier taxa has great potential to improve the reliability of source detection in the environment. Phylogenetic microarrays are an effective tool for rapidly measuring the full assortment of microbial taxa that distinguish fecal contaminants and deserve serious consideration for source tracking.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 1

| Source | #OTU ID | Bird ID taxa BIRD IDENTIFIER TAXA Lineage for representative OUT; GenBank Accession No.; Greengenes ID# (gg_id); clone name or description |
|---|---|---|
| bird feces | 17405 | Bacteria; Acidobacteria; Acidobacteriae_SP; Unclassified; Unclassified; Unclassified; sfA; 17405; AJ000986.2 gg_id: 14397 soil clone DA038 |
| bird feces | 33824 | Bacteria; Acidobacteria; Chloracidobacteria_SP; RB43_CL; Unclassified; Unclassified; sfA; 33824; EU132447.1 gg_id: 249548 grass prairie soil clone FFCH2343 |
| bird feces | 17256 | Bacteria; Acidobacteria; PAUC37f_SP; Unclassified; Unclassified; Unclassified; sfA; 17256; DQ676439.1 gg_id: 225540 Archaeal sediment and plankton freshwater pond suboxic freshwater-pond clone MVP-7A-12 |
| bird feces | 56106 | Bacteria; Acidobacteria; RB25_SP; Unclassified; Unclassified; Unclassified; sfA; 56106; EU652504.1 gg_id: 278125 Seasonal variation microbial Yel Sea sediment clone C8S-7 |
| bird feces | 56119 | Bacteria; Acidobacteria; RB25_SP; Unclassified; Unclassified; Unclassified; sfA; 56119; EU491807.1 gg_id: 258891 Abundance and microbial life ocean crust seafloor lavas East Pacific Rise clone EPR3967-O2-Bc60 |
| bird feces | 52276 | Bacteria; Actinobacteria; Acidimicrobiia_SP; EB1017_group_CL; Acidimicrobidae_bacterium_Ellin7143_OR; Unclassified; sfD; 52276; EU133040.1 gg_id: 241521 grass prairie soil clone FFCH2343 |
| bird feces | 51987 | Bacteria; Actinobacteria; Actinobacteridae_SP; ACK-M1_CL; Unclassified; Unclassified; sfA; 51987; AB154306.1 gg_id: 100186 freshwater clone S9F-17 |
| bird feces | 49065 | Bacteria; Actinobacteria; Actinobacteridae_SP; Actinobacteria_CL; Arthrobacter_OR; Arthrobacter_FM; sfA; 49065; AB248528.2 gg_id: 194632 Arthrobacter sp. str. LC7 |
| bird feces | 50468 | Bacteria; Actinobacteria; Actinobacteridae_SP; Propionibacterineae_CL; Propionibacterineae_OR; Propionibacterineae; sfB; 50468; EU289107.1 gg_id: 251531 microbiome cloacal openings urogenital and anal tracts tammar wallaby Macropus eugenii cloaca clone 8837-D0-1G |
| bird feces | 48861 | Bacteria; Actinobacteria; Actinobacteridae_SP; Unclassified; Unclassified; Unclassified; sfA; 48861; AY509239.1 gg_id: 100636 Arthrobacter rhombi str. S189 |
| bird feces | 48896 | Bacteria; Actinobacteria; Actinobacteridae_SP; Unclassified; Unclassified; Unclassified; sfA; 48896; DQ372937.1 gg_id: 150780 Lituella qinghaiensis str. YIM70185 |
| bird feces | 49101 | Bacteria; Actinobacteria; Actinobacteridae_SP; Unclassified; Unclassified; Unclassified; sfA; 49101; DQ248233.1 gg_id: 142315 carbon tetrachloride contaminated soil clone UC3 |
| bird feces | 49503 | Bacteria; Actinobacteria; Actinobacteridae_SP; Unclassified; Unclassified; Unclassified; sfA; 49503; X87758.1 gg_id: 12497 "Micrococcus mucilaginosus" |
| bird feces | 56374 | Bacteria; Actinobacteria; Actinobacteridae_SP; Unclassified; Unclassified; Unclassified; sfA; 56374; AM697014.1 gg_id: 220825 sequencing libraries indoor dust clone BF0001B040 |
| bird feces | 54803 | Bacteria; Actinobacteria; Coriobacteridae_SP; Coriobacteriales_CL; Coriobacteriales_OR; Coriobacteriales; Collinsella_FM; sfA; 54803; DQ797699.1 gg_id: 198471 human fecal clone RL206_aaj14g08 |
| bird feces | 52742 | Bacteria; Actinobacteria; Rubrobacteridae_SP; MC47_CL; Unclassified; Unclassified; sfA; 52742; DQ906774.1 gg_id: 241726 Oman subsurface soil clone 2A-2 |
| bird feces | 53081 | Bacteria; Actinobacteria; Rubrobacteridae_SP; Thermoleiphilaceae_CL; Thermoleiphilaceae_OR; Thermoleiphilaceae; sfL; 53081; EF516426.1 gg_id: 223287 grassland soil clone FCPO543 |
| bird feces | 12625 | Bacteria; Bacteroidetes; Leadbetterellaceae_SP; Leadbetterellaceae_CL; Leadbetterellaceae_OR; Leadbetterellaceae; sfD; 12625; DQ856549.1 gg_id: 252058 intestinal microflora Chinese mitten crab (Eriocheir sinensis) clone C3G |
| bird feces | 46583 | Bacteria; Bacteroidetes; p-184-o5_SP; Bacteroidales_CL; Bacteroidales; Unclassified; sfF; 46583; EU463421.1 gg_id: 291381 Evolution mammals and their gut microbes domesticated horse feces clone horsem_aai93f03 |
| bird feces | 48140 | Bacteria; Bacteroidetes; Unclassified; Unclassified; Unclassified; Unclassified; sgJ; 48140; EF123538.1 gg_id: 256828 Microbial disease microbial mats on Siderastrea siderea three regions wider Caribbean black band diseased (BBD) coral tissues clone WA_19pf |
| bird feces | 51129 | Bacteria; Chlamydiae; Rhabdochlamydiaceae_SP; Rhabdochlamydiaceae_CL; Rhabdochlamydiaceae_OR; Rhabdochlamydiaceae; sfA; 51129; AF364562.1 gg_id: 24629 Chlamydiales clone P-13 |
| bird feces | 33066 | Bacteria; Chlorobi; SJA-28_SP; PHOS-HC15_CL; Unclassified; Unclassified; sfA; 33066; EF632929.1 gg_id: 241447 Unique microbial contrasting aquatic altitude Andean Altiplano (northern Chile) freshwater sediment clone Pia-s-69 |
| bird feces | 59495 | Bacteria; Chloroflexi; Anaerolineae_SP; Anaerolineae_CL; Anaerolineae_OR; Anaerolineae; smR; 59495; AY555781.1 gg_id: 100661 Bor Khlueng hot spring clone PK28 |
| bird feces | 13282 | Bacteria; Chloroflexi; Unclassified; Unclassified; Unclassified; Unclassified; sfA; 13282; EU133950.1 gg_id: 250801 grass prairie soil clone FFCH5439 |

TABLE 1-continued

BIRD IDENTIFIER TAXA

| Source | #OTU ID | Bird ID taxa Lineage for representative OUT; GenBank Accession No.; Greengenes ID# (gg_id); clone name or description |
|---|---|---|
| bird feces | 52234 | Bacteria; Chloroflexi; Unclassified; Unclassified; Unclassified; Unclassified; sfE; 52234; EU134925.1 gg_id: 243369 grass prairie soil clone FFCH1093 |
| bird feces | 32312 | Bacteria; Elusimicrobia_TG1; Elusimicrobiales_SP; Elusimicrobiales_CL; Elusimicrobiales; Elusimicrobiaceae; sfH; 32312; EU050694.1 gg_id: 244224 Microbial waters production water Daqing oil field clone DQ312-6 |
| bird feces | 31701 | Bacteria; Elusimicrobia_TG1; FAC88_SP; Elusimicrobiales_CL; Elusimicrobiales; Unclassified; sfA; 31701; DQ128511.2 gg_id: 176150 forest soil clone CWT_CU03_E10 |
| bird feces | 53270 | Bacteria; Fibrobacteres; Fibrobacterales_SP; Fibrobacterales_CL; Fibrobacterales; Unclassified; sfA; 53270; AB275496.1 gg_id: 165381 Fibrobacter succinogenes str. OS102 |
| bird feces | 53729 | Bacteria; Fibrobacteres; Fibrobacterales_SP; Fibrobacterales_CL; Fibrobacterales; Unclassified; sfA; 53729; AB275498.1 gg_id: 164826 Fibrobacter succinogenes str. OS112 |
| bird feces | 7654 | Bacteria; Firmicutes; Bacilli_SP; Bacilli_CL; Bacillus_OR; Bacillus_FM; sfA; 7654; DQ005708.1 gg_id: 123915 Bacillus sp. soil-12 12 |
| bird feces | 8830 | Bacteria; Firmicutes; Bacilli_SP; Bacilli_CL; Bacillus_OR; Bacillus_FM; sfA; 8830; AY587834.1 gg_id: 106910 Portuguese dry smoked sausages (chouricos) type Ribatejano isolate str. Te72R |
| bird feces | 8678 | Bacteria; Firmicutes; Bacilli_SP; Halobacillus_CL; Halobacillus_OR; Halobacillus_FM; sfA; 8678; AB189326.1 gg_id: 103803 Gracilibacillus sp. str. SA-Gb1 |
| bird feces | 7822 | Bacteria; Firmicutes; Bacilli_SP; Halobacillus_CL; Halobacillus_OR; Halobacillus_FM; sfE; 7822; EU009752.1 gg_id: 242954 between classification and soils Ross Sea region Antarctic ornithogenic soil clone 3A |
| bird feces | 11161 | Bacteria; Firmicutes; Bacilli_SP; Lactobacillales_CL; Lactobacillales; Aerococcaceae; sfA; 11161; AY992171.1 gg_id: 134514 mouse cecum clone C16_M13 |
| bird feces | 11060 | Bacteria; Firmicutes; Bacilli_SP; Lactobacillales_CL; Lactobacillales; Aerococcaceae; sfB; 11060; AY207063.1 gg_id: 84770 human mouth clone P4PA_155 |
| bird feces | 10164 | Bacteria; Firmicutes; Bacilli_SP; Lactobacillales_CL; Lactobacillales; Lactobacillaceae; sfA; 10164; EU460773.1 gg_id: 298954 Evolution mammals and their gut microbes short-beaked echidna feces clone ECH_aai37g09 |
| bird feces | 10166 | Bacteria; Firmicutes; Bacilli_SP; Lactobacillales_CL; Lactobacillales; Lactobacillaceae; sfA; 10166; DQ815579.1 gg_id: 167922 mouse cecum clone aab43b09 |
| bird feces | 10369 | Bacteria; Firmicutes; Bacilli_SP; Lactobacillales_CL; Lactobacillales; Lactobacillaceae; sfA; 10369; AY445123.1 gg_id: 107193 Lactobacillus sp. str. RA2053 |
| bird feces | 10464 | Bacteria; Firmicutes; Bacilli_SP; Lactobacillales_CL; Lactobacillales; Lactobacillaceae; sfA; 10464; EU474878.1 gg_id: 297652 Evolution mammals and their gut microbes red river hog feces clone RRH_aaa01c12 |
| bird feces | 10486 | Bacteria; Firmicutes; Bacilli_SP; Lactobacillales_CL; Lactobacillales; Lactobacillaceae; sfA; 10486; EF097172.1 gg_id: 182972 mouse cecum clone SWPT18_aaa02d10 |
| bird feces | 10537 | Bacteria; Firmicutes; Bacilli_SP; Lactobacillales_CL; Lactobacillales; Lactobacillaceae; sfA; 10537; EU511492.1 gg_id: 273320 cecal contents Mus musculus strain C57BL/6J; WD9 clone WD9_aak05e02 |
| bird feces | 10823 | Bacteria; Firmicutes; Bacilli_SP; Lactobacillales_CL; Lactobacillales; Lactobacillaceae; sfA; 10823; EF097321.1 gg_id: 186266 mouse cecum clone SWPT19_aaa01a08 |
| bird feces | 10840 | Bacteria; Firmicutes; Bacilli_SP; Lactobacillales_CL; Lactobacillales; Lactobacillaceae; sfA; 10840; EU559595.1 gg_id: 276632 Lactobacillus crispatus str. ZDY35b |
| bird feces | 10897 | Bacteria; Firmicutes; Bacilli_SP; Lactobacillales_CL; Lactobacillales; Lactobacillaceae; sfA; 10897; AB175227.1 gg_id: 217703 Lactobacillus aviarius str. LAV2 |
| bird feces | 11243 | Bacteria; Firmicutes; Bacilli_SP; Lactobacillales_CL; Lactobacillales; Lactobacillaceae; sfA; 11243; AF049743.1 gg_id: 15206 Lactobacillus sp. str. LMG 17676 |
| bird feces | 9638 | Bacteria; Firmicutes; Bacilli_SP; Lactobacillales_CL; Lactobacillales; Lactobacillaceae; sfA; 9638; AY958956.1 gg_id: 134140 Microbes on human vaginal epithelium clone rRNA183 |
| bird feces | 9808 | Bacteria; Firmicutes; Bacilli_SP; Lactobacillales_CL; Lactobacillales; Lactobacillaceae; sfA; 9808; EU505251.1 gg_id: 268712 cecal contents Mus musculus strain C57BL/6J; myd4 clone myd4_aaa01b12 |
| bird feces | 9845 | Bacteria; Firmicutes; Bacilli_SP; Lactobacillales_CL; Lactobacillales; Lactobacillaceae; sfA; 9845; AY958957.1 gg_id: 133308 Microbes on human vaginal epithelium clone rRNA184 |

TABLE 1-continued

| Source | #OTU ID | Bird ID taxa BIRD IDENTIFIER TAXA Lineage for representative OUT; GenBank Accession No.; Greengenes ID# (gg_id); clone name or description |
|---|---|---|
| bird feces | 10570 | Bacteria; Firmicutes; Bacilli_SP; Lactobacillales_CL; Lactobacillales; Streptococcaceae; sfA; 10570; EU660340.1 gg_id: 290080 *Streptococcus pyogenes* str. Sp12 |
| bird feces | 9647 | Bacteria; Firmicutes; Bacilli_SP; Lactobacillales_CL; Lactobacillales; Streptococcaceae; sfA; 9647; AM774228.1 gg_id: 242407 *Streptococcus* sp. str. 1956-02 |
| bird feces | 10913 | Bacteria; Firmicutes; Bacilli_SP; Lactobacillales_CL; Lactobacillales; Unclassified; sfA; 10913; AY167958.1 gg_id: 75810 isolation and identification hyper-ammonia producing swine storage pits manure |
| bird feces | 11200 | Bacteria; Firmicutes; Bacilli_SP; Lactobacillales_CL; Lactobacillales; Unclassified; sfA; 11200; EF510392.1 gg_id: 217682 Loss During Antibiotic Treatment 1 Intubated Patients Colonized Pseudomonas aeruginosa endotracheal aspirate clone P2D1-749 |
| bird feces | 11454 | Bacteria; Firmicutes; Bacilli_SP; Lactobacillales_CL; Lactobacillales; Unclassified; sfA; 11454; AY179329.1 gg_id: 78915 *Vagococcus carniphilus* str. ATCC BAA-640 |
| bird feces | 11564 | Bacteria; Firmicutes; Bacilli_SP; Lactobacillales_CL; Lactobacillales; Unclassified; sfA; 11564; DQ818387.1 gg_id: 167065 mouse cecal microbiota-colonized zebrafish digestive tract clone aaa38a01 |
| bird feces | 11617 | Bacteria; Firmicutes; Bacilli_SP; Lactobacillales_CL; Lactobacillales; Unclassified; sfA; 11617; EF428246.2 gg_id: 226289 *Enterococcus munditi* str. HDYM-22 |
| bird feces | 11265 | Bacteria; Firmicutes; Bacilli_SP; Lactobacillales_CL; Lactobacillales; Unclassified; sfC; 11265; DQ818506.1 gg_id: 164676 mouse cecal microbiota-colonized zebrafish digestive tract clone aaa42g03 |
| bird feces | 8997 | Bacteria; Firmicutes; Bacilli_SP; Marinococcus_CL; Marinococcus_OR; Marinococcus_FM; sfC; 8997; EU118361.1 gg_id: 247299 Haloalkaliphilic AH-6: salt enriched natural saline habitat near Jamnagar (Latitude 22.27 N Longitude 70.07 E) Gujarat (India) salt-enriched soil isolate AH-6 haloalkaliphilic str. AH-6 |
| bird feces | 9077 | Bacteria; Firmicutes; Bacilli_SP; Marinococcus_CL; Marinococcus_OR; Marinococcus_FM; sfC; 9077; EU090232.1 gg_id: 244156 *Bacillus pseudofirmus* str. SJ2 |
| bird feces | 8198 | Bacteria; Firmicutes; Bacilli_SP; Planococcaceae_CL; Planococcaceae_OR; Planococcaceae; sfA; 8198; DQ345483.1 gg_id: 151430 during composting libraries compost clone 0B30 |
| bird feces | 9463 | Bacteria; Firmicutes; Bacilli_SP; Planococcaceae_CL; Planococcaceae_OR; Planococcaceae; sfC; 9463; EU465986.1 gg_id: 303114 Evolution mammals and their gut microbes African elephant feces clone AFEL3_aao15d02 |
| bird feces | 10864 | Bacteria; Firmicutes; Bacilli_SP; Staphylococcaceae_CL; Staphylococcaceae_OR; Staphylococcaceae; sfA; 10864; DQ818649.1 gg_id: 165441 mouse cecal microbiota-colonized zebrafish digestive tract clone aaa47d09 |
| bird feces | 10865 | Bacteria; Firmicutes; Bacilli_SP; Staphylococcaceae_CL; Staphylococcaceae_OR; Staphylococcaceae; sfA; 10865; DQ818011.1 gg_id: 163372 mouse cecal microbiota-colonized zebrafish digestive tract clone aaa51h09 |
| bird feces | 10870 | Bacteria; Firmicutes; Bacilli_SP; Staphylococcaceae_CL; Staphylococcaceae_OR; Staphylococcaceae; sfA; 10870; DQ818536.1 gg_id: 167429 mouse cecal microbiota-colonized zebrafish digestive tract clone aaa43h04 |
| bird feces | 10874 | Bacteria; Firmicutes; Bacilli_SP; Staphylococcaceae_CL; Staphylococcaceae_OR; Staphylococcaceae; sfA; 10874; DQ818949.1 gg_id: 169648 mouse cecal microbiota-colonized zebrafish digestive tract clone aab40a07 |
| bird feces | 10877 | Bacteria; Firmicutes; Bacilli_SP; Staphylococcaceae_CL; Staphylococcaceae_OR; Staphylococcaceae; sfA; 10877; DQ819160.1 gg_id: 163262 mouse cecal microbiota-colonized zebrafish digestive tract clone aab26e09 |
| bird feces | 10882 | Bacteria; Firmicutes; Bacilli_SP; Staphylococcaceae_CL; Staphylococcaceae_OR; Staphylococcaceae; sfA; 10882; DQ817842.1 gg_id: 164432 mouse cecal microbiota-colonized zebrafish digestive tract clone aaa49e06 |
| bird feces | 10889 | Bacteria; Firmicutes; Bacilli_SP; Staphylococcaceae_CL; Staphylococcaceae_OR; Staphylococcaceae; sfA; 10889; DQ818531.1 gg_id: 173153 mouse cecal microbiota-colonized zebrafish digestive tract clone aaa43f06 |
| bird feces | 10891 | Bacteria; Firmicutes; Bacilli_SP; Staphylococcaceae_CL; Staphylococcaceae_OR; Staphylococcaceae; sfA; 10891; DQ818625.1 gg_id: 173507 mouse cecal microbiota-colonized zebrafish digestive tract clone aaa47a02 |
| bird feces | 10905 | Bacteria; Firmicutes; Bacilli_SP; Staphylococcaceae_CL; Staphylococcaceae_OR; Staphylococcaceae; sfA; 10905; DQ818559.1 gg_id: 165086 mouse cecal microbiota-colonized zebrafish digestive tract clone aaa44e08 |
| bird feces | 10922 | Bacteria; Firmicutes; Bacilli_SP; Staphylococcaceae_CL; Staphylococcaceae_OR; Staphylococcaceae; sfA; 10922; DQ818137.1 gg_id: 170568 mouse cecal microbiota-colonized zebrafish digestive tract clone aaa53f04 |
| bird feces | 10933 | Bacteria; Firmicutes; Bacilli_SP; Staphylococcaceae_CL; Staphylococcaceae_OR; Staphylococcaceae; sfA; 10933; DQ819181.1 gg_id: 162111 mouse cecal microbiota-colonized zebrafish digestive tract clone aab26g08 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 10949 | Bacteria; Firmicutes; Bacilli_SP; Staphylococcaceae_CL; Staphylococcaceae_OR; Staphylococcaceae; sfA; 10949; DQ818495.1 gg_id: 168061 mouse cecal microbiota-colonized zebrafish digestive tract clone aaa42e03 |
| bird feces | 10956 | Bacteria; Firmicutes; Bacilli_SP; Staphylococcaceae_CL; Staphylococcaceae_OR; Staphylococcaceae; sfA; 10956; DQ818480.1 gg_id: 162612 mouse cecal microbiota-colonized zebrafish digestive tract clone aaa41h05 |
| bird feces | 10960 | Bacteria; Firmicutes; Bacilli_SP; Staphylococcaceae_CL; Staphylococcaceae_OR; Staphylococcaceae; sfA; 10960; DQ818557.1 gg_id: 172733 mouse cecal microbiota-colonized zebrafish digestive tract clone aaa44e05 |
| bird feces | 10975 | Bacteria; Firmicutes; Bacilli_SP; Staphylococcaceae_CL; Staphylococcaceae_OR; Staphylococcaceae; sfA; 10975; DQ818309.1 gg_id: 167326 mouse cecal microbiota-colonized zebrafish digestive tract clone aaa56c11 |
| bird feces | 10976 | Bacteria; Firmicutes; Bacilli_SP; Staphylococcaceae_CL; Staphylococcaceae_OR; Staphylococcaceae; sfA; 10976; AY395014.1 gg_id: 97108 Staphylococcus lentus NAB7 |
| bird feces | 10981 | Bacteria; Firmicutes; Bacilli_SP; Staphylococcaceae_CL; Staphylococcaceae_OR; Staphylococcaceae; sfA; 10981; DQ819320.1 gg_id: 162400 mouse cecal microbiota-colonized zebrafish digestive tract clone aab28d07 |
| bird feces | 10985 | Bacteria; Firmicutes; Bacilli_SP; Staphylococcaceae_CL; Staphylococcaceae_OR; Staphylococcaceae; sfA; 10985; DQ818084.1 gg_id: 173404 mouse cecal microbiota-colonized zebrafish digestive tract clone aaa52h05 |
| bird feces | 11019 | Bacteria; Firmicutes; Bacilli_SP; Staphylococcaceae_CL; Staphylococcaceae_OR; Staphylococcaceae; sfA; 11019; DQ818885.1 gg_id: 166903 mouse cecal microbiota-colonized zebrafish digestive tract clone aab39c02 |
| bird feces | 11029 | Bacteria; Firmicutes; Bacilli_SP; Staphylococcaceae_CL; Staphylococcaceae_OR; Staphylococcaceae; sfA; 11029; DQ818525.1 gg_id: 172585 mouse cecal microbiota-colonized zebrafish digestive tract clone aaa43d11 |
| bird feces | 11042 | Bacteria; Firmicutes; Bacilli_SP; Staphylococcaceae_CL; Staphylococcaceae_OR; Staphylococcaceae; sfA; 11042; DQ818085.1 gg_id: 172397 mouse cecal microbiota-colonized zebrafish digestive tract clone aaa52h06 |
| bird feces | 11046 | Bacteria; Firmicutes; Bacilli_SP; Staphylococcaceae_CL; Staphylococcaceae_OR; Staphylococcaceae; sfA; 11046; DQ818905.1 gg_id: 171828 mouse cecal microbiota-colonized zebrafish digestive tract clone aab39e04 |
| bird feces | 11051 | Bacteria; Firmicutes; Bacilli_SP; Staphylococcaceae_CL; Staphylococcaceae_OR; Staphylococcaceae; sfA; 11051; AB009946.1 gg_id: 14844 Staphylococcus vitulinus str. ATCC 51145T |
| bird feces | 11054 | Bacteria; Firmicutes; Bacilli_SP; Staphylococcaceae_CL; Staphylococcaceae_OR; Staphylococcaceae; sfA; 11054; DQ818192.1 gg_id: 164046 mouse cecal microbiota-colonized zebrafish digestive tract clone aaa54e08 |
| bird feces | 11122 | Bacteria; Firmicutes; Bacilli_SP; Staphylococcaceae_CL; Staphylococcaceae_OR; Staphylococcaceae; sfA; 11122; DQ817856.1 gg_id: 163058 mouse cecal microbiota-colonized zebrafish digestive tract clone aaa49f11 |
| bird feces | 11125 | Bacteria; Firmicutes; Bacilli_SP; Staphylococcaceae_CL; Staphylococcaceae_OR; Staphylococcaceae; sfA; 11125; DQ818384.1 gg_id: 163610 mouse cecal microbiota-colonized zebrafish digestive tract clone aaa37h03 |
| bird feces | 11146 | Bacteria; Firmicutes; Bacilli_SP; Staphylococcaceae_CL; Staphylococcaceae_OR; Staphylococcaceae; sfA; 11146; DQ818357.1 gg_id: 169788 mouse cecal microbiota-colonized zebrafish digestive tract clone aaa56h11 |
| bird feces | 11150 | Bacteria; Firmicutes; Bacilli_SP; Staphylococcaceae_CL; Staphylococcaceae_OR; Staphylococcaceae; sfA; 11150; DQ817886.1 gg_id: 163230 mouse cecal microbiota-colonized zebrafish digestive tract clone aaa50b11 |
| bird feces | 11151 | Bacteria; Firmicutes; Bacilli_SP; Staphylococcaceae_CL; Staphylococcaceae_OR; Staphylococcaceae; sfA; 11151; DQ818056.1 gg_id: 165904 mouse cecal microbiota-colonized zebrafish digestive tract clone aaa52e02 |
| bird feces | 11158 | Bacteria; Firmicutes; Bacilli_SP; Staphylococcaceae_CL; Staphylococcaceae_OR; Staphylococcaceae; sfA; 11158; DQ818190.1 gg_id: 169597 mouse cecal microbiota-colonized zebrafish digestive tract clone aaa54e05 |
| bird feces | 11159 | Bacteria; Firmicutes; Bacilli_SP; Staphylococcaceae_CL; Staphylococcaceae_OR; Staphylococcaceae; sfA; 11159; DQ818425.1 gg_id: 163324 mouse cecal microbiota-colonized zebrafish digestive tract clone aaa39f03 |
| bird feces | 11176 | Bacteria; Firmicutes; Bacilli_SP; Staphylococcaceae_CL; Staphylococcaceae_OR; Staphylococcaceae; sfA; 11176; DQ819112.1 gg_id: 163932 mouse cecal microbiota-colonized zebrafish digestive tract clone aab26a04 |
| bird feces | 11192 | Bacteria; Firmicutes; Bacilli_SP; Staphylococcaceae_CL; Staphylococcaceae_OR; Staphylococcaceae; sfA; 11192; DQ818564.1 gg_id: 167097 mouse cecal microbiota-colonized zebrafish digestive tract clone aaa44g07 |
| bird feces | 11193 | Bacteria; Firmicutes; Bacilli_SP; Staphylococcaceae_CL; Staphylococcaceae_OR; Staphylococcaceae; sfA; 11193; DQ817822.1 gg_id: 167505 mouse cecal microbiota-colonized zebrafish digestive tract clone aaa49c02 |
| bird feces | 11199 | Bacteria; Firmicutes; Bacilli_SP; Staphylococcaceae_CL; Staphylococcaceae_OR; Staphylococcaceae; sfA; 11199; DQ817940.1 gg_id: 162051 mouse cecal microbiota-colonized zebrafish digestive tract clone aaa51a02 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 11212 | Bacteria; Firmicutes; Bacilli_SP; Staphylococcaceae_CL; Staphylococcaceae_OR; Staphylococcaceae; sfA; 11212; DQ818398.1 gg_id: 171919 mouse cecal microbiota-colonized zebrafish digestive tract clone aaa38e04 |
| bird feces | 11226 | Bacteria; Firmicutes; Bacilli_SP; Staphylococcaceae_CL; Staphylococcaceae_OR; Staphylococcaceae; sfA; 11226; DQ819306.1 gg_id: 169905 mouse cecal microbiota-colonized zebrafish digestive tract clone aab28c03 |
| bird feces | 11240 | Bacteria; Firmicutes; Bacilli_SP; Staphylococcaceae_CL; Staphylococcaceae_OR; Staphylococcaceae; sfA; 11240; DQ818532.1 gg_id: 173146 mouse cecal microbiota-colonized zebrafish digestive tract clone aaa43f09 |
| bird feces | 11251 | Bacteria; Firmicutes; Bacilli_SP; Staphylococcaceae_CL; Staphylococcaceae_OR; Staphylococcaceae; sfA; 11251; DQ817959.1 gg_id: 166866 mouse cecal microbiota-colonized zebrafish digestive tract clone aaa51c01 |
| bird feces | 11269 | Bacteria; Firmicutes; Bacilli_SP; Staphylococcaceae_CL; Staphylococcaceae_OR; Staphylococcaceae; sfA; 11269; DQ817973.1 gg_id: 163367 mouse cecal microbiota-colonized zebrafish digestive tract clone aaa51d05 |
| bird feces | 11282 | Bacteria; Firmicutes; Bacilli_SP; Staphylococcaceae_CL; Staphylococcaceae_OR; Staphylococcaceae; sfA; 11282; DQ818Q4.1 gg_id: 164904 mouse cecal microbiota-colonized zebrafish digestive tract clone aaa53b09 |
| bird feces | 11302 | Bacteria; Firmicutes; Bacilli_SP; Staphylococcaceae_CL; Staphylococcaceae_OR; Staphylococcaceae; sfA; 11302; DQ817917.1 gg_id: 165287 mouse cecal microbiota-colonized zebrafish digestive tract clone aaa50f06 |
| bird feces | 11306 | Bacteria; Firmicutes; Bacilli_SP; Staphylococcaceae_CL; Staphylococcaceae_OR; Staphylococcaceae; sfA; 11306; DQ818299.1 gg_id: 172046 mouse cecal microbiota-colonized zebrafish digestive tract clone aaa56b06 |
| bird feces | 11328 | Bacteria; Firmicutes; Bacilli_SP; Staphylococcaceae_CL; Staphylococcaceae_OR; Staphylococcaceae; sfA; 11328; DQ818371.1 gg_id: 168326 mouse cecal microbiota-colonized zebrafish digestive tract clone aaa37e03 |
| bird feces | 11331 | Bacteria; Firmicutes; Bacilli_SP; Staphylococcaceae_CL; Staphylococcaceae_OR; Staphylococcaceae; sfA; 11331; DQ818515.1 gg_id: 166061 mouse cecal microbiota-colonized zebrafish digestive tract clone aaa43c04 |
| bird feces | 11332 | Bacteria; Firmicutes; Bacilli_SP; Staphylococcaceae_CL; Staphylococcaceae_OR; Staphylococcaceae; sfA; 11332; DQ818746.1 gg_id: 172770 mouse cecal microbiota-colonized zebrafish digestive tract clone aaa37d09 |
| bird feces | 11351 | Bacteria; Firmicutes; Bacilli_SP; Staphylococcaceae_CL; Staphylococcaceae_OR; Staphylococcaceae; sfA; 11351; DQ817839.1 gg_id: 172742 mouse cecal microbiota-colonized zebrafish digestive tract clone aaa49e03 |
| bird feces | 11358 | Bacteria; Firmicutes; Bacilli_SP; Staphylococcaceae_CL; Staphylococcaceae_OR; Staphylococcaceae; sfA; 11358; DQ818687.1 gg_id: 164452 mouse cecal microbiota-colonized zebrafish digestive tract clone aaa48e06 |
| bird feces | 11361 | Bacteria; Firmicutes; Bacilli_SP; Staphylococcaceae_CL; Staphylococcaceae_OR; Staphylococcaceae; sfA; 11361; DQ818136.1 gg_id: 163394 mouse cecal microbiota-colonized zebrafish digestive tract clone aaa53f03 |
| bird feces | 11363 | Bacteria; Firmicutes; Bacilli_SP; Staphylococcaceae_CL; Staphylococcaceae_OR; Staphylococcaceae; sfA; 11363; DQ818606.1 gg_id: 171124 mouse cecal microbiota-colonized zebrafish digestive tract clone aaa46c07 |
| bird feces | 11370 | Bacteria; Firmicutes; Bacilli_SP; Staphylococcaceae_CL; Staphylococcaceae_OR; Staphylococcaceae; sfA; 11370; DQ818503.1 gg_id: 173447 mouse cecal microbiota-colonized zebrafish digestive tract clone aaa42f07 |
| bird feces | 11379 | Bacteria; Firmicutes; Bacilli_SP; Staphylococcaceae_CL; Staphylococcaceae_OR; Staphylococcaceae; sfA; 11379; DQ819208.1 gg_id: 170456 mouse cecal microbiota-colonized zebrafish digestive tract clone aab27b03 |
| bird feces | 11391 | Bacteria; Firmicutes; Bacilli_SP; Staphylococcaceae_CL; Staphylococcaceae_OR; Staphylococcaceae; sfA; 11391; DQ818442.1 gg_id: 172281 mouse cecal microbiota-colonized zebrafish digestive tract clone aaa40e04 |
| bird feces | 11392 | Bacteria; Firmicutes; Bacilli_SP; Staphylococcaceae_CL; Staphylococcaceae_OR; Staphylococcaceae; sfA; 11392; DQ817955.1 gg_id: 170771 mouse cecal microbiota-colonized zebrafish digestive tract clone aaa51b09 |
| bird feces | 11412 | Bacteria; Firmicutes; Bacilli_SP; Staphylococcaceae_CL; Staphylococcaceae_OR; Staphylococcaceae; sfA; 11412; AB212761.1 gg_id: 148758 Staphylococcus sciuri |
| bird feces | 11413 | Bacteria; Firmicutes; Bacilli_SP; Staphylococcaceae_CL; Staphylococcaceae_OR; Staphylococcaceae; sfA; 11413; DQ818105.1 gg_id: 164856 mouse cecal microbiota-colonized zebrafish digestive tract clone aaa53b10 |
| bird feces | 11418 | Bacteria; Firmicutes; Bacilli_SP; Staphylococcaceae_CL; Staphylococcaceae_OR; Staphylococcaceae; sfA; 11418; DQ818416.1 gg_id: 172876 mouse cecal microbiota-colonized zebrafish digestive tract clone aaa39c08 |
| bird feces | 11426 | Bacteria; Firmicutes; Bacilli_SP; Staphylococcaceae_CL; Staphylococcaceae_OR; Staphylococcaceae; sfA; 11426; DQ819158.1 gg_id: 163351 mouse cecal microbiota-colonized zebrafish digestive tract clone aab26e07 |
| bird feces | 11433 | Bacteria; Firmicutes; Bacilli_SP; Staphylococcaceae_CL; Staphylococcaceae_OR; Staphylococcaceae; sfA; 11433; DQ818370.1 gg_id: 168146 mouse cecal microbiota-colonized zebrafish digestive tract clone aaa37d11 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 11439 | Bacteria; Firmicutes; Bacilli_SP; Staphylococcaceae_CL; Staphylococcaceae_OR; Staphylococcaceae; sfA; 11439; DQ818684.1 gg_id: 165790 mouse cecal microbiota-colonized zebrafish digestive tract clone aaa48d09 |
| bird feces | 11456 | Bacteria; Firmicutes; Bacilli_SP; Staphylococcaceae_CL; Staphylococcaceae_OR; Staphylococcaceae; sfA; 11456; DQ818643.1 gg_id: 173509 mouse cecal microbiota-colonized zebrafish digestive tract clone aaa47c09 |
| bird feces | 11464 | Bacteria; Firmicutes; Bacilli_SP; Staphylococcaceae_CL; Staphylococcaceae_OR; Staphylococcaceae; sfA; 11464; DQ817977.1 gg_id: 164262 mouse cecal microbiota-colonized zebrafish digestive tract clone aaa51e02 |
| bird feces | 11478 | Bacteria; Firmicutes; Bacilli_SP; Staphylococcaceae_CL; Staphylococcaceae_OR; Staphylococcaceae; sfA; 11478; DQ819023.1 gg_id: 173261 mouse cecal microbiota-colonized zebrafish digestive tract clone aab25a05 |
| bird feces | 11481 | Bacteria; Firmicutes; Bacilli_SP; Staphylococcaceae_CL; Staphylococcaceae_OR; Staphylococcaceae; sfA; 11481; DQ818439.1 gg_id: 165069 mouse cecal microbiota-colonized zebrafish digestive tract clone aaa40d10 |
| bird feces | 11482 | Bacteria; Firmicutes; Bacilli_SP; Staphylococcaceae_CL; Staphylococcaceae_OR; Staphylococcaceae; sfA; 11482; DQ818773.1 gg_id: 169123 mouse cecal microbiota-colonized zebrafish digestive tract clone aab37g03 |
| bird feces | 11489 | Bacteria; Firmicutes; Bacilli_SP; Staphylococcaceae_CL; Staphylococcaceae_OR; Staphylococcaceae; sfA; 11489; DQ817926.1 gg_id: 167954 mouse cecal microbiota-colonized zebrafish digestive tract clone aaa50g03 |
| bird feces | 11504 | Bacteria; Firmicutes; Bacilli_SP; Staphylococcaceae_CL; Staphylococcaceae_OR; Staphylococcaceae; sfA; 11504; DQ818238.1 gg_id: 170368 mouse cecal microbiota-colonized zebrafish digestive tract clone aaa55b11 |
| bird feces | 11508 | Bacteria; Firmicutes; Bacilli_SP; Staphylococcaceae_CL; Staphylococcaceae_OR; Staphylococcaceae; sfA; 11508; DQ818784.1 gg_id: 173428 mouse cecal microbiota-colonized zebrafish digestive tract clone aab37h04 |
| bird feces | 11530 | Bacteria; Firmicutes; Bacilli_SP; Staphylococcaceae_CL; Staphylococcaceae_OR; Staphylococcaceae; sfA; 11530; DQ818633.1 gg_id: 164560 mouse cecal microbiota-colonized zebrafish digestive tract clone aaa47b06 |
| bird feces | 11541 | Bacteria; Firmicutes; Bacilli_SP; Staphylococcaceae_CL; Staphylococcaceae_OR; Staphylococcaceae; sfA; 11541; DQ819283.1 gg_id: 161810 mouse cecal microbiota-colonized zebrafish digestive tract clone aab27h12 |
| bird feces | 11562 | Bacteria; Firmicutes; Bacilli_SP; Staphylococcaceae_CL; Staphylococcaceae_OR; Staphylococcaceae; sfA; 11562; DQ817873.1 gg_id: 167224 mouse cecal microbiota-colonized zebrafish digestive tract clone aaa50a05 |
| bird feces | 11563 | Bacteria; Firmicutes; Bacilli_SP; Staphylococcaceae_CL; Staphylococcaceae_OR; Staphylococcaceae; sfA; 11563; DQ817963.1 gg_id: 163110 mouse cecal microbiota-colonized zebrafish digestive tract clone aaa51c05 |
| bird feces | 11570 | Bacteria; Firmicutes; Bacilli_SP; Staphylococcaceae_CL; Staphylococcaceae_OR; Staphylococcaceae; sfA; 11570; DQ817979.1 gg_id: 165870 mouse cecal microbiota-colonized zebrafish digestive tract clone aaa51e04 |
| bird feces | 11589 | Bacteria; Firmicutes; Bacilli_SP; Staphylococcaceae_CL; Staphylococcaceae_OR; Staphylococcaceae; sfA; 11589; DQ818433.1 gg_id: 161796 mouse cecal microbiota-colonized zebrafish digestive tract clone aaa40c10 |
| bird feces | 11597 | Bacteria; Firmicutes; Bacilli_SP; Staphylococcaceae_CL; Staphylococcaceae_OR; Staphylococcaceae; sfA; 11597; DQ817837.1 gg_id: 164380 mouse cecal microbiota-colonized zebrafish digestive tract clone aaa49d11 |
| bird feces | 11598 | Bacteria; Firmicutes; Bacilli_SP; Staphylococcaceae_CL; Staphylococcaceae_OR; Staphylococcaceae; sfA; 11598; DQ818602.1 gg_id: 169651 mouse cecal microbiota-colonized zebrafish digestive tract clone aaa46b09 |
| bird feces | 11613 | Bacteria; Firmicutes; Bacilli_SP; Staphylococcaceae_CL; Staphylococcaceae_OR; Staphylococcaceae; sfA; 11613; DQ818288.1 gg_id: 172787 mouse cecal microbiota-colonized zebrafish digestive tract clone aaa56a05 |
| bird feces | 11616 | Bacteria; Firmicutes; Bacilli_SP; Staphylococcaceae_CL; Staphylococcaceae_OR; Staphylococcaceae; sfA; 11616; DQ818068.1 gg_id: 162034 mouse cecal microbiota-colonized zebrafish digestive tract clone aaa52f07 |
| bird feces | 11624 | Bacteria; Firmicutes; Bacilli_SP; Staphylococcaceae_CL; Staphylococcaceae_OR; Staphylococcaceae; sfA; 11624; AF467405.1 gg_id: 64578 Staphylococcus sp. clone Tminor25 |
| bird feces | 11631 | Bacteria; Firmicutes; Bacilli_SP; Staphylococcaceae_CL; Staphylococcaceae_OR; Staphylococcaceae; sfA; 11631; DQ818184.1 gg_id: 162944 mouse cecal microbiota-colonized zebrafish digestive tract clone aaa54d10 |
| bird feces | 11638 | Bacteria; Firmicutes; Bacilli_SP; Staphylococcaceae_CL; Staphylococcaceae_OR; Staphylococcaceae; sfA; 11638; DQ818912.1 gg_id: 168549 mouse cecal microbiota-colonized zebrafish digestive tract clone aab39f02 |
| bird feces | 11639 | Bacteria; Firmicutes; Bacilli_SP; Staphylococcaceae_CL; Staphylococcaceae_OR; Staphylococcaceae; sfA; 11639; DQ818386.1 gg_id: 163608 mouse cecal microbiota-colonized zebrafish digestive tract clone aaa37h10 |
| bird feces | 11654 | Bacteria; Firmicutes; Bacilli_SP; Staphylococcaceae_CL; Staphylococcaceae_OR; Staphylococcaceae; sfA; 11654; DQ818871.1 gg_id: 168886 mouse cecal microbiota-colonized zebrafish digestive tract clone aab39a03 |

TABLE 1-continued

| Source | #OTU ID | Bird ID taxa BIRD IDENTIFIER TAXA Lineage for representative OUT; GenBank Accession No.; Greengenes ID# (gg_id); clone name or description |
|---|---|---|
| bird feces | 11658 | Bacteria; Firmicutes; Bacilli_SP; Staphylococcaceae_CL; Staphylococcaceae_OR; Staphylococcaceae; sfA; 11658; DQ818325.1 gg_id: 170467 mouse cecal microbiota-colonized zebrafish digestive tract clone aaa56e07 |
| bird feces | 11667 | Bacteria; Firmicutes; Bacilli_SP; Staphylococcaceae_CL; Staphylococcaceae_OR; Staphylococcaceae; sfA; 11667; DQ817965.1 gg_id: 172941 mouse cecal microbiota-colonized zebrafish digestive tract clone aaa51c07 |
| bird feces | 11677 | Bacteria; Firmicutes; Bacilli_SP; Staphylococcaceae_CL; Staphylococcaceae_OR; Staphylococcaceae; sfA; 11677; DQ818426.1 gg_id: 169999 mouse cecal microbiota-colonized zebrafish digestive tract clone aaa39f06 |
| bird feces | 11699 | Bacteria; Firmicutes; Bacilli_SP; Staphylococcaceae_CL; Staphylococcaceae_OR; Staphylococcaceae; sfA; 11699; DQ818464.1 gg_id: 163147 mouse cecal microbiota-colonized zebrafish digestive tract clone aaa41d08 |
| bird feces | 11702 | Bacteria; Firmicutes; Bacilli_SP; Staphylococcaceae_CL; Staphylococcaceae_OR; Staphylococcaceae; sfA; 11702; DQ817814.1 gg_id: 173200 mouse cecal microbiota-colonized zebrafish digestive tract clone aaa49b05 |
| bird feces | 9330 | Bacteria; Firmicutes; Bacilli_SP; Staphylococcaceae_CL; Staphylococcaceae_OR; Staphylococcaceae; sfA; 9330; AB009940.1 gg_id: 14831 *Staphylococcus kloosii* str. ATCC 43959T |
| bird feces | 9546 | Bacteria; Firmicutes; Bacilli_SP; Staphylococcaceae_CL; Staphylococcaceae_OR; Staphylococcaceae; sfA; 9546; DQ279396.1 gg_id: 143602 Dynamic during maturation Tuber magnatum Pico ascoma Staphylococcus clone TM13_18 |
| bird feces | 7723 | Bacteria; Firmicutes; Bacilli_SP; Unclassified; Unclassified; Unclassified; sfA; 7723; EU434531.1 gg_id: 270179 *Bacillus firmus* str. b250 |
| bird feces | 7755 | Bacteria; Firmicutes; Bacilli_SP; Unclassified; Unclassified; Unclassified; sfA; 7755; EF405625.1 gg_id: 214941 *Bacillus* sp. str. CCBAU 13245 |
| bird feces | 7866 | Bacteria; Firmicutes; Bacilli_SP; Unclassified; Unclassified; Unclassified; sfA; 7866; AJ229179.1 gg_id: 27496 anoxic bulk soil flooded rice microcosm clone BSV05 clone |
| bird feces | 7989 | Bacteria; Firmicutes; Bacilli_SP; Unclassified; Unclassified; Unclassified; sfA; 7989; AY493963.1 gg_id: 136810 Fingerprinting aggregates soil clone 1370 |
| bird feces | 8380 | Bacteria; Firmicutes; Bacilli_SP; Unclassified; Unclassified; Unclassified; sfA; 8380; EF682914.1 gg_id: 249220 Eastern Mediterranean atmosphere clone F12_1B_FL |
| bird feces | 8535 | Bacteria; Firmicutes; Bacilli_SP; Unclassified; Unclassified; Unclassified; sfA; 8535; AY289508.1 gg_id: 101214 *Bacillus* sp. IDA5367 |
| bird feces | 8882 | Bacteria; Firmicutes; Bacilli_SP; Unclassified; Unclassified; Unclassified; sfA; 8882; EF451042.1 gg_id: 211366 *Bacillus aeris* str. HIO-9 |
| bird feces | 4200 | Bacteria; Firmicutes; Clostridia_SP; C23_k02_CL; Clostridiales; C22_o06_FM; sfB; 4200; EU510417.1 gg_id: 270726 cecal contents *Mus musculus* strain C57BL/6J; WD4 clone WD4_aal38c10 |
| bird feces | 38481 | Bacteria; Firmicutes; Clostridia_SP; Catabacter_CL; Catabacter_OR; Catabacter_FM; sgG; 38481; EU219960.1 gg_id: 253182 study prokaryotic approach landfill soil 5.5 ft. depth clone C134B |
| bird feces | 39361 | Bacteria; Firmicutes; Clostridia_SP; Clostridiales_CL; Clostridiales; Clostridiaceae; sfA; 39361; DQ816172.1 gg_id: 169374 zebrafish gut microbiota-colonized mouse cecum clone aaa77e04 |
| bird feces | 39200 | Bacteria; Firmicutes; Clostridia_SP; Clostridiales_CL; Clostridiales; Clostridiaceae; sfC; 39200; X77814.1 gg_id: 16193 Segmented filamentous bacterium |
| bird feces | 7513 | Bacteria; Firmicutes; Clostridia_SP; Clostridiales_CL; Clostridiales; Clostridium_FM; sfU; 7513; EU463227.1 gg_id: 292680 Evolution mammals and their gut microbes naked mole-rat feces clone molerat_aai72a05 |
| bird feces | 539 | Bacteria; Firmicutes; Clostridia_SP; Clostridiales_CL; Clostridiales; Eubacterium_FM; sgL; 539; DQ802093.1 gg_id: 174108 human fecal clone RL241_aaj03a04 |
| bird feces | 38836 | Bacteria; Firmicutes; Clostridia_SP; Clostridiales_CL; Clostridiales; Ruminococcus_FM; shE; 38836; EU381752.1 gg_id: 262007 Rumen implicates Bacteroidetes major particulate phylum rumen liquid phase fistulated Holstein heifer clone L3A_G11 |
| bird feces | 38272 | Bacteria; Firmicutes; Clostridia_SP; Clostridiales_CL; Clostridiales; Ruminococcus_FM; shM; 38272; AB192036.1 gg_id: 141236 termite gut homogenate clone M2PB4-02 |
| bird feces | 2451 | Bacteria; Firmicutes; Clostridia_SP; Clostridiales_CL; Clostridiales; Unclassified; sfA; 2451; AY993423.1 gg_id: 134953 mouse cecum clone C19_K19 |
| bird feces | 40773 | Bacteria; Firmicutes; Clostridia_SP; Clostridiales_CL; Clostridiales; Unclassified; sfC; 40773; EU474824.1 gg_id: 300854 Evolution mammals and their gut microbes takin feces clone TAK_aaa02g06 |
| bird feces | 41772 | Bacteria; Firmicutes; Clostridia_SP; Clostridiales_CL; Clostridiales; Unclassified; skB; 41772; EU470366.1 gg_id: 28724 Evolution mammals and their gut microbes Grevy's zebra feces clone GZ_aaa01d12 |
| bird feces | 4765 | Bacteria; Firmicutes; Clostridia_SP; F24-F10_CL; Clostridiales; Unclassified; sfA; 4765; EU344710.1 gg_id: 259684 Foregut Fermentation Birds: Hoatzin Crop Supports Case Convergence Ruminants adult hoatzin crop clone hoa6l_12e03 |

TABLE 1-continued

| Source | #OTU ID | Bird ID taxa — Lineage for representative OUT; GenBank Accession No.; Greengenes ID# (gg_id); clone name or description | BIRD IDENTIFIER TAXA |
|---|---|---|---|
| bird feces | 5959 | Bacteria; Firmicutes; Clostridia; Clostridiales; Unclassified; sfA; 5959; EU506804.1 gg_id: 277492 cecal contents *Mus musculus* strain C57BL/6J; MD20 clone MD20_aap56f04 | |
| bird feces | 5961 | Bacteria; Firmicutes; Clostridia; Clostridiales; Unclassified; sfA; 5961; EU508137.1 gg_id: 266340 cecal contents *Mus musculus* strain C57BL/6J; MD26 clone MD26_aaa01b10 | |
| bird feces | 5996 | Bacteria; Firmicutes; Clostridia; Clostridiales; Unclassified; sfA; 5996; EU508389.1 gg_id: 263798 cecal contents *Mus musculus* strain C57BL/6J; MD27 clone MD27_aaa04g05 | |
| bird feces | 6103 | Bacteria; Firmicutes; Clostridia; Clostridiales; Unclassified; sfA; 6103; EU507310.1 gg_id: 276961 cecal contents *Mus musculus* strain C57BL/6J; MD23 clone MD23_2aaa01e02 | |
| bird feces | 6273 | Bacteria; Firmicutes; Clostridia; Clostridiales; Unclassified; sfA; 6273; EU507026.1 gg_id: 270403 cecal contents *Mus musculus* strain C57BL/6J; MD21 clone MD21_aar10a06 | |
| bird feces | 6347 | Bacteria; Firmicutes; Clostridia; Clostridiales; Unclassified; sfA; 6347; EU509549.1 gg_id: 262388 cecal contents *Mus musculus* strain C57BL/6J; MD9 clone MD9_aap60f03 | |
| bird feces | 6359 | Bacteria; Firmicutes; Clostridia; Clostridiales; Unclassified; sfA; 6359; EU506947.1 gg_id: 269979 cecal contents *Mus musculus* strain C57BL/6J; MD21 clone MD21_aar08g04 | |
| bird feces | 6366 | Bacteria; Firmicutes; Clostridia; Clostridiales; Unclassified; sfA; 6366; EU506630.1 gg_id: 276637 cecal contents *Mus musculus* strain C57BL/6J; MD20 clone MD20_aap53f06 | |
| bird feces | 6454 | Bacteria; Firmicutes; Clostridia; Clostridiales; Unclassified; sfA; 6454; EU509385.1 gg_id: 268420 cecal contents *Mus musculus* strain C57BL/6J; MD9 clone MD9_aap57a08 | |
| bird feces | 6516 | Bacteria; Firmicutes; Clostridia; Clostridiales; Unclassified; sfA; 6516; EU506439.1 gg_id: 275931 cecal contents *Mus musculus* strain C57BL/6J; MD19 clone MD19_aaa01g06 | |
| bird feces | 6556 | Bacteria; Firmicutes; Clostridia; Clostridiales; Unclassified; sfA; 6556; EU508174.1 gg_id: 276801 cecal contents *Mus musculus* strain C57BL/6J; MD26 clone MD26_aaa02e05 | |
| bird feces | 6568 | Bacteria; Firmicutes; Clostridia; Clostridiales; Unclassified; sfA; 6568; EU508259.1 gg_id: 267552 cecal contents *Mus musculus* strain C57BL/6J; MD26 clone MD26_aaa04g08 | |
| bird feces | 6673 | Bacteria; Firmicutes; Clostridia; Clostridiales; Unclassified; sfA; 6673; EU508263.1 gg_id: 259490 cecal contents *Mus musculus* strain C57BL/6J; MD26 clone MD26_aaa04g10 | |
| bird feces | 6695 | Bacteria; Firmicutes; Clostridia; Clostridiales; Unclassified; sfA; 6695; EU507630.1 gg_id: 264644 cecal contents *Mus musculus* strain C57BL/6J; MD23 clone MD23_aaa02b11 | |
| bird feces | 6771 | Bacteria; Firmicutes; Clostridia; Clostridiales; Unclassified; sfA; 6771; EU508720.1 gg_id: 258353 cecal contents *Mus musculus* strain C57BL/6J; MD4 clone MD4_aap49h05 | |
| bird feces | 6855 | Bacteria; Firmicutes; Clostridia; Clostridiales; Unclassified; sfA; 6855; EU508528.1 gg_id: 273169 cecal contents *Mus musculus* strain C57BL/6J; MD2 clone MD2_aap34h10 | |
| bird feces | 6938 | Bacteria; Firmicutes; Clostridia; Clostridiales; Unclassified; sfA; 6938; EU506820.1 gg_id: 261032 cecal contents *Mus musculus* strain C57BL/6J; MD20 clone MD20_aap56h05 | |
| bird feces | 6950 | Bacteria; Firmicutes; Clostridia; Clostridiales; Unclassified; sfA; 6950; EU506765.1 gg_id: 277513 cecal contents *Mus musculus* strain C57BL/6J; MD20 clone MD20_aap55h09 | |
| bird feces | 7009 | Bacteria; Firmicutes; Clostridia; Clostridiales; Unclassified; sfA; 7009; EU508329.1 gg_id: 266121 cecal contents *Mus musculus* strain C57BL/6J; MD27 clone MD27_aaa02g06 | |
| bird feces | 7043 | Bacteria; Firmicutes; Clostridia; Clostridiales; Unclassified; sfA; 7043; EU506726.1 gg_id: 258560 cecal contents *Mus musculus* strain C57BL/6J; MD20 clone MD20_aap55c02 | |
| bird feces | 7094 | Bacteria; Firmicutes; Clostridia; Clostridiales; Unclassified; sfA; 7094; EU506654.1 gg_id: 259562 cecal contents *Mus musculus* strain C57BL/6J; MD20 clone MD20_aap54a03 | |
| bird feces | 7147 | Bacteria; Firmicutes; Clostridia; Clostridiales; Unclassified; sfA; 7147; EU507028.1 gg_id: 266414 cecal contents *Mus musculus* strain C57BL/6J; MD21 clone MD21_aar10h01 | |
| bird feces | 7213 | Bacteria; Firmicutes; Clostridia; Clostridiales; Unclassified; sfA; 7213; EU506314.1 gg_id: 276253 cecal contents *Mus musculus* strain C57BL/6J; MD18 clone MD18_aap63b04 | |
| bird feces | 7227 | Bacteria; Firmicutes; Clostridia; Clostridiales; Unclassified; sfA; 7227; EU506835.1 gg_id: 275802 cecal contents *Mus musculus* strain C57BL/6J; MD21 clone MD21_aar07b02 | |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 7230 | Bacteria; Firmicutes; Clostridia_SP; M2_1g06_CL; Clostridiales; Unclassified; sfA; 7230; EU506734.1 gg_id: 272379 cecal contents *Mus musculus* strain C57BL/6J; MD20 clone MD20_aap55c10 |
| bird feces | 7256 | Bacteria; Firmicutes; Clostridia_SP; M2_1g06_CL; Clostridiales; Unclassified; sfA; 7256; EU509421.1 gg_id: 271053 cecal contents *Mus musculus* strain C57BL/6J; MD9 clone MD9_aap57h03 |
| bird feces | 7352 | Bacteria; Firmicutes; Clostridia_SP; M2_1g06_CL; Clostridiales; Unclassified; sfA; 7352; EU508390.1 gg_id: 266641 cecal contents *Mus musculus* strain C57BL/6J; MD27 clone MD27_aaa04g06 |
| bird feces | 7370 | Bacteria; Firmicutes; Clostridia_SP; M2_1g06_CL; Clostridisates; Unclassified; sfA; 7370; EU506342.1 gg_id: 271911 cecal contents *Mus musculus* strain C57BL/6J; MD18 clone MD18_aap63f07 |
| bird feces | 7427 | Bacteria; Firmicutes; Clostridia_SP; M2_1g06_CL; Clostridiales; Unclassified; sfA; 7427; EU509527.1 gg_id: 274897 cecal contents *Mus musculus* strain C57BL/6J; MD9 clone MD9_aap60b10 |
| bird feces | 7581 | Bacteria; Firmicutes; Clostridia_SP; M2_1g06_CL; Clostridiales; Unclassified; sfA; 7581; EU506468.1 gg_id: 258977 cecal contents *Mus musculus* strain C57BL/6J; MD19 clone MD19_aaa02d07 |
| bird feces | 43298 | Bacteria; Firmicutes; Clostridia_SP; Peptostreptococcaceae_CL; Peptostreptococcaceae_OR; Peptostreptococcaceae; siX; 43298; EU475677.1 gg_id: 287746 Evolution mammals and their gut microbes *babirusa* feces BARB_aaa01c08 |
| bird feces | 58841 | Bacteria; Firmicutes; Mollicutes_SP; Mycoplasmatales_CL; Mycoplasmatales; Mycoplasma_FM; sgM; 58841; U06095.1 gg_id: 15810 *Ureaplasma urealyticum* str. U26 (serovar 14) |
| bird feces | 58653 | Bacteria; Firmicutes; Mollicutes_SP; Spiroplasma_CL; Spiroplasma_OR; Spiroplasma_FM; sfA; 58653; AF303132.1 gg_id: 71794 *Mesoplasma lactucae* str. 831-C4; ATCC 49193 ATCC |
| bird feces | 58972 | Bacteria; Firmicutes; Mollicutes_SP; *Spiroplasma* CL; Spiroplasma_OR; Spiroplasma_FM; sfC; 58972; AY325304.1 gg_id: 100058 *Spiroplasma melliferum* str. BC-3 |
| bird feces | 9208 | Bacteria; Firmicutes; Mollicutes_SP; Unclassified; Unclassified; Unclassified; sfH; 9208; EU471917.1 gg_id: 295226 Evolution mammals and their gut microbes Asiatic elephant feces clone AE3_aaa02d08 |
| bird feces | 9056 | Bacteria; Firmicutes; Symbiobacteria_SP; D2_CL; Symbiobacterales; Unclassified; sfA; 9056; EF174259.1 gg_id: 175339 direct activated 4th maturation stage sludge clone F31-814 |
| bird feces | 30576 | Bacteria; Firmicutes; Unclassified; Unclassified; Unclassified; Unclassified; sfK; 30576; EU101270.1 gg_id: 257793 Sulfide/oxygen supply ratio predicts outcome competition among sulfur-oxidizing waters Frasassi sulfidic cave stream biofilm clone RS06101_B8 |
| bird feces | 33370 | Bacteria; Fusobacteria; Fusobacteriaceae_SP; Fusobacteriaceae_CL; Fusobacteriaceae_OR; Fusobacteriaceae; sfA; 33370; DQ814895.1 gg_id: 165848 zebrafish digestive tract clone aab55b10 |
| bird feces | 33716 | Bacteria; Fusobacteria; Fusobacteriaceae_SP; Fusobacteriaceae_CL; Fusobacteriaceae_OR; Fusobacteriaceae; sfA; 33716; DQ814909.1 gg_id: 166066 zebrafish digestive tract clone aab55d03 |
| bird feces | 33920 | Bacteria; Fusobacteria; Fusobacteriaceae_SP; Fusobacteriaceae_CL; Fusobacteriaceae_OR; Fusobacteriaceae; sfA; 33920; DQ815299.1 gg_id: 169717 zebrafish digestive tract clone aab52h12 |
| bird feces | 34023 | Bacteria; Fusobacteria; Fusobacteriaceae_SP; Fusobacteriaceae_CL; Fusobacteriaceae_OR; Fusobacteriaceae; sfA; 34023; DQ814705.1 gg_id: 162228 zebrafish digestive tract clone aaa35c07 |
| bird feces | 34232 | Bacteria; Fusobacteria; Fusobacteriaceae_SP; Fusobacteriaceae_CL; Fusobacteriaceae_OR; Fusobacteriaceae; sfA; 34232; DQ817035.1 gg_id: 172000 zebrafish gut microbiota-colonized mouse cecum clone aaa94h08 |
| bird feces | 34273 | Bacteria; Fusobacteria; Fusobacteriaceae_SP; Fusobacteriaceae_CL; Fusobacteriaceae_OR; Fusobacteriaceae; sfA; 34273; DQ815286.1 gg_id: 171805 zebrafish digestive tract clone aab52g04 |
| bird feces | 33894 | Bacteria; Fusobacteria; Ilyobacter_SP; Ilyobacter_CL; Ilyobacter_OR; Ilyobacter_FM; sfA; 33894; AY592371.1 gg_id: 105657 deep-sea mud volcano clone Amsterdam-2B-11; BC20-2B-11 |
| bird feces | 55194 | Bacteria; Gemmatimonadetes; Gemmatimonadales_SP; Gemmatimonadales_CL; Gemmatimonadales; Unclassified; sfA; 55194; EU134855.1 gg_id: 245934 grass prairie soil clone FFCH15336 |
| bird feces | 54550 | Bacteria; Gemmatimonadetes; Unclassified; Unclassified; Unclassified; sfE; 54550; DQ125826.1 gg_id: 134102 uranium contaminated soil clone AKAU4049 |
| bird feces | 52241 | Bacteria; Lentisphaerae; Unclassified; Unclassified; Unclassified; Unclassified; sfD; 52241; EU491130.1 gg_id: 265874 Abundance and microbial life ocean crust seafloor lavas Loi'hi Seamount Pisces Peak X2 clone P9X2b3E06 |
| bird feces | 31526 | Bacteria; MBMPE71; Unclassified; Unclassified; Unclassified; Unclassified; sfA; 31526; EU385751.1 gg_id: 269013 Stratified microbes sediments Core MD05-2896 subseafloor sediment South China Sea clone MD2896-B151 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 32665 | Bacteria; Moorella; Unclassified; Unclassified; Unclassified; Unclassified; sfA; 32665; AY884087.1 gg_id: 130065 Moorella thermoacetica str. AMP |
| bird feces | 54672 | Bacteria; NKB19; Unclassified; Unclassified; Unclassified; Unclassified; sfE; 54672; EU491334.1 gg_id: 275015 Abundance and microbial life ocean crust seafloor lavas Loi'hi Seamount Pisces Peak X2 clone P9X2b2E07 |
| bird feces | 55350 | Bacteria; NKB19; Unclassified; Unclassified; Unclassified; Unclassified; sfI; 55350; AJ387899.1 gg_id: 38854 anaerobic TCB-dechlorinating consortium clone SJP-2 |
| bird feces | 54580 | Bacteria; NKB19; Unclassified; Unclassified; Unclassified; Unclassified; sfI; 54580; AJ387900.1 gg_id: 49810 anaerobic TCB-dechlorinating consortium clone SJP-3 |
| bird feces | 14114 | Bacteria; OP1; Unclassified; Unclassified; Unclassified; Unclassified; sfG; 14114; EU542526.1 gg_id: 275118 Effects chemical structure concentration on pathways microbial during dechlorination coplanar PCBs slurries sediment and soil slurry clone Er-LLAYS-77 |
| bird feces | 58207 | Bacteria; OP11; OP11-3_SP; Unclassified; Unclassified; Unclassified; sfI; 58207; EU386117.1 gg_id: 270788 Biogeographical and microbes sediments on subseafloor sediment South China Sea clone MD2905-B5 |
| bird feces | 53132 | Bacteria; Planctomycetes; WPS-1_SP; Unclassified; Unclassified; Unclassified; sfX; 53132; AJ241009.1 gg_id: 2843 marine sediment clone Sva0503 |
| bird feces | 30687 | Bacteria; Proteobacteria; Alphaproteobacteria_SP; Aurantimonadaceae_CL; Aurantimonadaceae_OR; Aurantimonadaceae; sfA; 30687; EU535534.1 gg_id: 280975 profile human microbiota antecubital fossa (inner elbow) skin clone nbr26g02 |
| bird feces | 15421 | Bacteria; Proteobacteria; Alphaproteobacteria_SP; Bradyrhizobiales_CL; Bradyrhizobiales; Methylobacteriaceae; sfA; 15421; AY436812.1 gg_id: 105470 Methylobacterium sp. str. ST4.9 |
| bird feces | 15692 | Bacteria; Proteobacteria; Alphaproteobacteria_SP; Bradyrhizobiales_CL; Bradyrhizobiales; Methylobacteriaceae; sfA; 15692; EF116582.1 gg_id: 182127 Methylobacterium populi str. TNAU1 |
| bird feces | 15910 | Bacteria; Proteobacteria; Alphaproteobacteria_SP; Bradyrhizobiales_CL; Bradyrhizobiales; Methylobacteriaceae; sfA; 15910; M95653.1 gg_id: 4775 Methylobacterium sp str. M27 |
| bird feces | 15914 | Bacteria; Proteobacteria; Alphaproteobacteria_SP; Bradyrhizobiales_CL; Bradyrhizobiales; Methylobacteriaceae; sfA; 15914; AY436811.1 gg_id: 105313 Methylobacterium sp. str. ST4.1 |
| bird feces | 31012 | Bacteria; Proteobacteria; Alphaproteobacteria_SP; Bradyrhizobiales_CL; Bradyrhizobiales; Unclassified; sfB; 31012; AB099936.1 gg_id: 79338 inactive deep-sea hydrothermal vent chimneys clone IheB2-3 |
| bird feces | 16917 | Bacteria; Proteobacteria; Alphaproteobacteria_SP; Caedibacteraceae_CL; Caedibacteraceae_OR; Caedibacteraceae; sfB; 16917; EU137369.1 gg_id: 258296 Bartonella-positive fleas: and assembly patterns Oropsylla hirsuta (prairie dog flea) Cynomys ludovicianus (black-tailed prairie dog) clone Oh3123O11E |
| bird feces | 17358 | Bacteria; Proteobacteria; Alphaproteobacteria_SP; Caedibacteraceae_CL; Caedibacteraceae_OR; Caedibacteraceae; sfB; 17358; EU137515.1 gg_id: 265520 Bartonella-positive fleas: and assembly patterns Oropsylla hirsuta (prairie dog flea) Cynomys ludovicianus (black-tailed prairie dog) clone Oh_3123F4B |
| bird feces | 30873 | Bacteria; Proteobacteria; Alphaproteobacteria_SP; Caedibacteraceae_CL; Caedibacteraceae_OR; Caedibacteraceae; sfU; 30873; AB089086.1 gg_id: 78256 termite gut homogenate clone Rs-M08 |
| bird feces | 14806 | Bacteria; Proteobacteria; Alphaproteobacteria_SP; Oleomonas_CL; Oleomonas_OR; Oleomonas_FM; sfC; 14806; EU133521.1 gg_id: 244485 grass prairie soil clone FFCH17833 |
| bird feces | 14401 | Bacteria; Proteobacteria; Alphaproteobacteria_SP; Oleomonas_CL; Oleomonas_OR; Oleomonas_FM; sgL; 14401; DQ648974.1 gg_id: 188118 biodiversity and rhizosphere polluted site TGGE screening libraries PCB contaminated soil clone lhap15 |
| bird feces | 15219 | Bacteria; Proteobacteria; Alphaproteobacteria_SP; Oleomonas_CL; OCS126_OR; Unclassified; sfA; 15219; AY907748.1 gg_id: 136455 identification picoplankton populations contrasting waters Arabian Sea water clone A313005 |
| bird feces | 18182 | Bacteria; Proteobacteria; Alphaproteobacteria_SP; Pelagibacter_CL; Consistiales; SAR11_FM; sfA; 18182; AB193892.1 gg_id: 108809 deep-sea vent clone Ma-NB12 |
| bird feces | 15613 | Bacteria; Proteobacteria; Alphaproteobacteria_SP; Rhizobiaceae_CL; Rhizobiaceae_OR; Rhizobiaceae; sfA; 15613; AY691400.1 gg_id: 103507 Rhizobium sp. 1pud22.2 |
| bird feces | 15723 | Bacteria; Proteobacteria; Alphaproteobacteria_SP; Rhizobiaceae_CL; Rhizobiaceae_OR; Rhizobiaceae; sfA; 15723; EF364374.1 gg_id: 217747 Rhizobium leguminosarum str. Alm-3 |
| bird feces | 15832 | Bacteria; Proteobacteria; Alphaproteobacteria_SP; Rhizobiaceae_CL; Rhizobiaceae_OR; Rhizobiaceae; sfA; 15832; AM697022.1 gg_id: 217449 sequencing libraries indoor dust clone BF0001B048 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 16076 | Bacteria; Proteobacteria; Alphaproteobacteria_SP; Rhizobiaceae_CL; Rhizobiaceae_OR; Rhizobiaceae; sfA; 16076; AY221178.1 gg_id: 80113 Rhizobium tropici EBRI 32 |
| bird feces | 16256 | Bacteria; Proteobacteria; Alphaproteobacteria_SP; Rhizobiaceae_CL; Rhizobiaceae_OR; Rhizobiaceae; sfA; 16256; EF364384.1 gg_id: 218446 Rhizobium leguminosarum str. Mad-7 |
| bird feces | 31967 | Bacteria; Proteobacteria; Alphaproteobacteria_SP; Rickettsiales_CL; Rickettsiales; Unclassified; sfP; 31967; EF667921.1 gg_id: 236767 Long-term maintenance species-specific microbiota basal metazoan Hydra epithelium clone Hv(lakePohlsee)_25 |
| bird feces | 54677 | Bacteria; Proteobacteria; Deltaproteobacteria_SP; Bacteriovorax_CL; Bacteriovorax_OR; Bacteriovorax_FM; sfS; 54677; EU050840.1 gg_id: 254686 libraries sediment Kings Bay Svalbard Arctic clone ss1_B_07_54 |
| bird feces | 29794 | Bacteria; Proteobacteria; Deltaproteobacteria_SP; CTD005-82B-02_CL; Unclassified; Unclassified; sfG; 29794; AM259914.1 gg_id: 251443 Chondrilla nucula-specific sponge mesohyl clone CN28 |
| bird feces | 54786 | Bacteria; Proteobacteria; Deltaproteobacteria_SP; EB1021_CL; Unclassified; Unclassified; sfH; 54786; EF076107.1 gg_id: 244235 Sponge-microorganisms: evolution ecology and biotechnological potential Bahamas: Little San Salvador Island clone PK066 |
| bird feces | 51760 | Bacteria; Proteobacteria; Deltaproteobacteria_SP; Geobacter_CL; Geobacter_OR; Geobacter_FM; sfC; 51760; EU134475.1 gg_id: 251863 grass prairie soil clone FFCH4187 |
| bird feces | 31188 | Bacteria; Proteobacteria; Deltaproteobacteria_SP; MIZ46_CL; CrystalBog021E5_OR; Unclassified; sfC; 31188; EU373907.1 gg_id: 264962 southern Cretan margin (eastern Mediterranean Sea) canyon and slope sediment clone HCM3MC91_5E_FL |
| bird feces | 54856 | Bacteria; Proteobacteria; Deltaproteobacteria_SP; Myxococcales_CL; Myxococcales; Polyangiaceae; sfC; 54856; EU134472.1 gg_id: 250014 grass prairie soil clone FFCH4137 |
| bird feces | 54514 | Bacteria; Proteobacteria; Deltaproteobacteria_SP; Myxococcales_CL; Myxococcales; Unclassified; sgQ; 54514; EU134562.1 gg_id: 240430 grass prairie soil clone FFCH3849 |
| bird feces | 13243 | Bacteria; Proteobacteria; Deltaproteobacteria_SP; Unclassified; Unclassified; Unclassified; sil; 13243; AB089107.1 gg_id: 100887 termite gut homogenate clone Rs-M47 |
| bird feces | 59132 | Bacteria; Proteobacteria; Epsilonproteobacteria_SP; Campylobacterales_CL; Campylobacteraceae_OR; Campylobacteraceae; sfA; 59132; AB181362.1 gg_id: 100512 Campylobacter lari str. A1 |
| bird feces | 59222 | Bacteria; Proteobacteria; Epsilonproteobacteria_SP; Campylobacterales_CL; Campylobacteraceae_OR; Campylobacteraceae; sfA; 59222; AF371868.1 gg_id: 104552 swine intestine clone p-4321-4Wa3 |
| bird feces | 58765 | Bacteria; Proteobacteria; Epsilonproteobacteria_SP; Helicobacterales_CL; Helicobacteraceae; sfA; 58765; EU508577.1 gg_id: 259514 cecal contents Mus musculus strain C57BL/6J; MD2 clone MD2_aap35f02 |
| bird feces | 59113 | Bacteria; Proteobacteria; Epsilonproteobacteria_SP; Helicobacterales_CL; Helicobacteraceae; sfA; 59113; AY461713.1 gg_id: 100344 mouse caecum clone |
| bird feces | 59160 | Bacteria; Proteobacteria; Epsilonproteobacteria_SP; Helicobacterales_CL; Helicobacteraceae; sfA; 59160; EU508405.1 gg_id: 262004 cecal contents Mus musculus strain C57BL/6J; MD2 clone MD2_aap33a10 |
| bird feces | 59243 | Bacteria; Proteobacteria; Epsilonproteobacteria_SP; Helicobacterales_CL; Helicobacteraceae; sfA; 59243; AY631948.1 gg_id: 106719 Helicobacter felis str. Lee CS3 |
| bird feces | 58907 | Bacteria; Proteobacteria; Epsilonproteobacteria_SP; Sulfurovumales_CL; Sulfurovumales; Unclassified; sfC; 58907; EU555133.1 gg_id: 262157 Microbial Sulfide Hydrothermal Vent Field Juan de Fuca Ridge Dudley hydrothermal vent clone 4132B37 |
| bird feces | 19385 | Bacteria; Proteobacteria; Gammaproteobacteria_SP; Alteromonadales_CL; Alteromonadales; Unclassified; sfI; 19385; AB369184.1 gg_id: 247072 Microbiological Assessment Circulation Mud Fluids During First Operation Drilling Deep-Earth Research Vessel 'Chikyu' Offshore Shimokita Peninsula Riser drilling mud fluid clone CK06-06_Mud_MAS4B-19 |
| bird feces | 23335 | Bacteria; Proteobacteria; Gammaproteobacteria_SP; B2M28_CL; Unclassified; Unclassified; sfA; 23335; DQ394926.1 gg_id: 156200 harbor sediment clone VHS-B3-3 |
| bird feces | 29939 | Bacteria; Proteobacteria; Gammaproteobacteria_SP; Betaproteobacteria_CL; Comamonadaceae_OR; Comamonadaceae; sfA; 29939; AY081982.1 gg_id: 68619 atrazine-catabolizing microbial presence methanol clone KRA30 + 15 |
| bird feces | 30494 | Bacteria; Proteobacteria; Gammaproteobacteria_SP; Betaproteobacteria_CL; Comamonadaceae_OR; Comamonadaceae; sfA; 30494; AB187018.1 gg_id: 102476 Suiyo seamount hydrothermal vent water 0.2 micro-m filterable fraction clone SSM-EB11 |
| bird feces | 20804 | Bacteria; Proteobacteria; Gammaproteobacteria_SP; Betaproteobacteria_CL; Methylophilales; OM43_FM; sfA; 20804; EU010148.1 gg_id: 254163 Biogeography Singapore seawaters seawater clone B72 |

TABLE 1-continued

| Source | #OTU ID | Bird ID taxa BIRD IDENTIFIER TAXA Lineage for representative OUT; GenBank Accession No.; Greengenes ID# (gg_id); clone name or description |
|---|---|---|
| bird feces | 21997 | Bacteria; Proteobacteria; Betaproteobacteria_SP; Betaproteobacteria_CL; Ralstoniaceae_OR; Ralstoniaceae; sfA; 21997; EF562174.1 gg_id: 249438 Subsurface microbial deep-granitic-fracture water Colorado Henderson Molybdenum Mine clone 7150D1B72 |
| bird feces | 22088 | Bacteria; Proteobacteria; Betaproteobacteria_SP; Betaproteobacteria_CL; Ralstoniaceae_OR; Ralstoniaceae; sfA; 22088; EF600587.1 gg_id: 287646 leaf litter clone E2-27 |
| bird feces | 22356 | Bacteria; Proteobacteria; Betaproteobacteria_SP; Betaproteobacteria_CL; Ralstoniaceae_OR; Ralstoniaceae; sfA; 22356; AB021403.1 gg_id: 7408 Ralstonia syzygii str. ATCC 49543T |
| bird feces | 22209 | Bacteria; Proteobacteria; Betaproteobacteria_SP; Betaproteobacteria_CL; Rhodocyclales; Azospira_FM; sfA; 2209; AJ630274.1 gg_id: 99759 electricity-generating microbial fuel cell clone MFC-EB4 |
| bird feces | 18127 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 18127; DQ815280.1 gg_id: 162387 zebrafish digestive tract clone aab52f06 |
| bird feces | 18209 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 18209; X82248.1 gg_id: 10216 Photorhabdus subsp. luminescens str. DSM 3368 |
| bird feces | 18739 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 18739; EU513180.1 gg_id: 264777 Xenorhabdus poinarii str. SRK 1 |
| bird feces | 18838 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 18838; DQ816382.1 gg_id: 172232 zebrafish gut microbiota-colonized mouse cecum clone aab17c12 |
| bird feces | 28509 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 28509; Z96096.1 gg_id: 9802 Brenneria paradisiaca str. LMG 2542 |
| bird feces | 28827 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 28827; AM179913.1 gg_id: 145059 identification microflora (Oncorhynchus mykiss) rainbow trout intestine clone G4-5 |
| bird feces | 29075 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 29075; EF025326.1 gg_id: 176468 Enterobacter cloacae str. SREPS1 |
| bird feces | 29400 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 29400; AY501386.1 gg_id: 99525 Pantoea sp. str. PPE7 |
| bird feces | 29406 | Bacteria; Proteobacteria; Gammaproteobacteria_SP; Enterobacteriales_CL; Enterobacteriales_Enterobacteriaceae_OR; Enterobacteriales_Enterobacteriaceae; sfA; 29406; EF469625.1 gg_id: 220333 Specific symbiotic flies Subfamily Tephritinae (Diptera Tephritidae) and their extraperitrophic area midgut |
| bird feces | 32537 | Bacteria; Proteobacteria; Gammaproteobacteria_SP; Enterobacteriales_CL; Enterobacteriales_Enterobacteriaceae_OR; Enterobacteriales_Enterobacteriaceae; sfB; 32537; M63248.1 gg_id: 9641 Buchnera aphidicola |
| bird feces | 32889 | Bacteria; Proteobacteria; Gammaproteobacteria_SP; Enterobacteriales_CL; Enterobacteriales_Enterobacteriaceae_OR; Enterobacteriales_Enterobacteriaceae; sgD; 32889; AB067723.1 gg_id: 28528 Megacopta punctatissima symbiont |
| bird feces | 31097 | Bacteria; Proteobacteria; Gammaproteobacteria_SP; Legionellales_CL; Legionellales; Aquicella_FM; sfA; 31097; EU134712.1 gg_id: 245968 grass prairie soil clone FFCH5316 |
| bird feces | 23235 | Bacteria; Proteobacteria; Gammaproteobacteria_SP; Legionellales_CL; Legionellales; Unclassified; sfR; 23235; EU134741.1 gg_id: 236854 grass prairie soil clone FFCH12674 |
| bird feces | 23285 | Bacteria; Proteobacteria; Gammaproteobacteria_SP; Legionellales_CL; Legionellales; Unclassified; siW; 23285; EU134755.1 gg_id: 249080 grass prairie soil clone FFCH15639 |
| bird feces | 33295 | Bacteria; Proteobacteria; Gammaproteobacteria_SP; Moraxellaceae_CL; Moraxellaceae_OR; Moraxellaceae; sfA; 33295; AY277551.1 gg_id: 89870 Acinetobacter lwoffii str, 1E |
| bird feces | 19785 | Bacteria; Proteobacteria; Gammaproteobacteria_SP; Oceanimonaceae_CL; Oceanimonaceae_OR; Oceanimonaceae; sfA; 19785; AB019390.1 gg_id: 9401 Oceanimonas doudoroffii str. MBIC1298 (=ATCC27123) |
| bird feces | 22684 | Bacteria; Proteobacteria; Gammaproteobacteria_SP; Oligobrachia_CL; Oligobrachia_OR; Oligobrachia_FM; sfA; 22684; EU086774.1 gg_id: 281000 Siboglinum fiordicum and Endosymbionts Siboglinidae (Annelida) Norway: Raunefjorden clone 49_2 |
| bird feces | 18852 | Bacteria; Proteobacteria; Gammaproteobacteria_SP; Pasteurellaceae_CL; Pasteurellaceae_OR; Pasteurellaceae; sfA; 18852; AY172732.1 gg_id: 91315 Bisgaard taxon 40 str. B301529/00/1 |

TABLE 1-continued

Bird ID taxa
BIRD IDENTIFIER TAXA

| Source | #OTU ID | Lineage for representative OUT; GenBank Accession No.; Greengenes ID# (gg_id); clone name or description |
|---|---|---|
| bird feces | 24740 | Bacteria; Proteobacteria; Gammaproteobacteria_SP; Pseudomonadaceae_CL; Pseudomonadaceae_OR; Pseudomonadaceae; sfA; 24740; EU169179.1 gg_id: 253450 *Pseudomonas fluorescens* str. B73 |
| bird feces | 25559 | Bacteria; Proteobacteria; Gammaproteobacteria_SP; Pseudomonadaceae_CL; Pseudomonadaceae_OR; Pseudomonadaceae; sfA; 25559; EU537631.1 gg_id: 281835 profile human microbiota antecubital fossa (inner elbow) skin clone nbt74a01 |
| bird feces | 25624 | Bacteria; Proteobacteria; Gammaproteobacteria_SP; Pseudomonadaceae_CL; Pseudomonadaceae_OR; Pseudomonadaceae; sfA; 25624; AJ846281.1 gg_id: 102254 *Pseudomonas* sp. HHS16 |
| bird feces | 23143 | Bacteria; Proteobacteria; Gammaproteobacteria_SP; Unclassified; Unclassified; Unclassified; sfF; 23143; AF223298.1 gg_id: 37006 marine sediment clone B2M54 |
| bird feces | 23604 | Bacteria; Proteobacteria; Gammaproteobacteria_SP; Unclassified; Unclassified; Unclassified; sgZ; 23604; EU528230.1 gg_id: 286126 Seasonal Dynamics Mudflat Mouth Major Kentucky Lake Reservoir Tributary sediment clone 3.5.8 |
| bird feces | 34380 | Bacteria; Proteobacteria; Gammaproteobacteria_SP; Vibrionaceae_CL; Vibrionaceae_OR; Vibrionaceae; sfB; 34380; EU073024.1 gg_id: 245931 *Vibrio penaeicida* HC051105-8 |
| bird feces | 14019 | Bacteria; SC3; Unclassified; Unclassified; Unclassified; Unclassified; sfC; 14019; DQ128633.2 gg_id: 181780 no tillage soil clone HSB NT21_A06 |
| bird feces | 34755 | Bacteria; Spirochaetes; Spirochaetales_SP; Spirochaetales_CL; Spirochaetales; Spirochaetaceae; sfK; 34755; AF524010.1 gg_id: 63216 forested wetland clone FW20 |
| bird feces | 34467 | Bacteria; Spirochaetes; Spirochaetales_SP; Spirochaetales_CL; Spirochaetales; Spirochaetaceae; sgX; 34467; EU469944.1 gg_id: 287483 Evolution mammals and their gut microbes western lowland *gorilla* feces clone GOR_aag74h11 |
| bird feces | 53836 | Bacteria; Thermi; Deinococcales_SP; Deinococcales_CL; Deinococcales; Deinococcaceae; sfD; 53836; Y11331.1 gg_id: 1408 *Deinococcus proteolyticus* str. DSM 20540T |
| bird feces | 57901 | Bacteria; TM7; MJK10_SP; Unclassified; Unclassified; Unclassified; sfB; 57901; EU134918.1 gg_id: 241684 grass prairie soil clone FFCH16433 |
| bird feces | 36273 | Bacteria; WPS-2; Unclassified; Unclassified; Unclassified; Unclassified; sfA; 36273; EU462261.1 gg_id: 288010 Evolution mammals and their gut microbes chimpanzee feces clone CHIMP1_aaj38f12 |
| bird feces | 48655 | Bacteria; WPS-2; Unclassified; Unclassified; Unclassified; Unclassified; sfC; 48655; EU475271.1 gg_id: 295252 Evolution mammals and their gut microbes rock hyrax feces clone RHSD_aaa02g09 |
| bird feces | 17542 | Bacteria; WS1; Unclassified; Unclassified; Unclassified; Unclassified; sfA; 17542; EU245588.1 gg_id: 239409 Miniprimer new lens viewing world hypersaline microbial mat clone MAT-CR-M3-D06 |
| bird feces | 58104 | Bacteria; ZB2; FW128_SP; Unclassified; Unclassified; Unclassified; sfM; 58104; AB177137.1 gg_id: 202153 Biogeographical and microbes hydrate-bearing deep marine sediments on Pacific Ocean Margin methane hydrate bearing subseafloor sediment Peru margin (ODP Leg 201) clone ODP1230B10.08 |

TABLE 2

Grazer ID taxa
GRAZER IDENTIFIER TAXA

| Source | #OTU ID | Lineage for representative OUT; GenBank Accession No.; Greengenes ID# (gg_id); clone name or description |
|---|---|---|
| grazer feces | 17332 | Bacteria; AC1; Unclassified; Unclassified; Unclassified; Unclassified; sfI; 17332; AM712334.1 gg_id: 254942 detection and ly microbial population Brothers Seamount Kermadec Arc New Zealand biofilm hydrothermal vent orifice clone MS12-2-F10 |
| grazer feces | 56668 | Bacteria; Acidobacteria; BPC102_SP; Unclassified; Unclassified; Unclassified; sfB; 56668; DQ906917.1 gg_id: 247876 Oman subsurface soil clone 12C-3 |
| grazer feces | 55845 | Bacteria; Acidobacteria; BPC102_SP; Unclassified; Unclassified; Unclassified; sfE; 55845; EU373940.1 gg_id: 262954 southern Cretan margin (eastern Mediterranean Sea) canyon and slope sediment clone HCM3MC91_4C_FL |
| grazer feces | 56680 | Bacteria; Acidobacteria; Unclassified; Unclassified; Unclassified; Unclassified; sfG; 56680; EU287123.1 gg_id: 256935 Pacific arctic surface sediment clone P13-30 |
| grazer feces | 47318 | Bacteria; Bacteroidetes; Bacteroidales_SP; Bacteroidales_CL; Bacteroidales; Bacteroidaceae; siH; 47318; EU475009.1 gg_id: 288250 Evolution mammals and their gut microbes red river hog feces clone RRH_aaa04d04 |
| grazer feces | 47014 | Bacteria; Bacteroidetes; Bacteroidales_SP; Bacteroidales_CL; Bacteroidales; Odoribacteriaceae; sfA; 47014; AY983350.1 gg_id: 121452 human descending colon mucosal biopsy clone A451 |
| grazer feces | 47671 | Bacteria; Bacteroidetes; Bacteroidales_SP; Bacteroidales_CL; Bacteroidales; Rikenellaceae; sfA; 47671; EF100039.1 gg_id: 190844 mouse cecum clone SWPT5_aaa03g11 |
| grazer feces | 47910 | Bacteria; Bacteroidetes; Bacteroidales_SP; Bacteroidales_CL; Bacteroidales; Rikenellaceae; sfA; 47910; EU468891.1 gg_id: 296840 Evolution mammals and their gut microbes Speke's gazelle feces clone SP2_f11 |
| grazer feces | 47926 | Bacteria; Bacteroidetes; Bacteroidales_SP; Bacteroidales_CL; Bacteroidales; Rikenellaceae; sfA; 47926; EU468718.1 gg_id: 301755 Evolution mammals and their gut microbes okapi feces clone OK2_e10_2 |
| grazer feces | 47993 | Bacteria; Bacteroidetes; Bacteroidales_SP; Bacteroidales_CL; Bacteroidales; Rikenellaceae; sfL; 47993; EF608538.1 gg_id: 232888 predatory *Poecilus chalcites* their response lab rearing and antibiotic treatment digestive tract ground beetle clone PCD-16 |
| grazer feces | 47111 | Bacteria; Bacteroidetes; Bacteroidales_SP; Bacteroidales_CL; Bacteroidales; Rikenellaceae; sfM; 47111; AB198561.1 gg_id: 135820 termite gut wall fraction clone RsW02-107 |
| grazer feces | 46643 | Bacteria; Bacteroidetes; Bacteroidales_SP; Bacteroidales_CL; Bacteroidales; Unclassified; sfA; 46643; EU474825.1 gg_id: 296618 Evolution mammals and their gut microbes takin feces clone TAK_aaa02h09 |
| grazer feces | 46849 | Bacteria; Bacteroidetes; Bacteroidales_SP; Bacteroidales_CL; Bacteroidales; Unclassified; sfE; 46849; EU465890.1 gg_id: 302081 Evolution mammals and their gut microbes African elephant feces clone AFEL3_aao13e11 |
| grazer feces | 47008 | Bacteria; Bacteroidetes; Bacteroidales_SP; Bacteroidales_CL; Bacteroidales; Unclassified; sfE; 47008; EF686629.1 gg_id: 247878 Sequences Manifest Rumen Yunnan Yel Cattle (*Bos Taurus*) rumen fluid clone YNRC118 |
| grazer feces | 47264 | Bacteria; Bacteroidetes; Bacteroidales_SP; Bacteroidales_CL; Bacteroidales; Unclassified; sfE; 47264; EU460173.1 gg_id: 287676 Evolution mammals their gut microbes eastern black and white colobus feces clone COL_aai15h05 |
| grazer feces | 46363 | Bacteria; Bacteroidetes; Bacteroidales_SP; Bacteroidales_CL; Bacteroidales; Unclassified; sfH; 46363; EU471655.1 gg_id: 301407 Evolution mammals and their gut microbes Asiatic elephant feces clone AE1_aaa03a02 |
| grazer feces | 12128 | Bacteria; Bacteroidetes; Bacteroidales_SP; Bacteroidales_CL; Bacteroidales; Unclassified; sfJ; 12128; AF320926.1 gg_id: 70586 Lake Michigan sediment clone LMBA49 |
| grazer feces | 46929 | Bacteria; Bacteroidetes; Bacteroidales_SP; Bacteroidales_CL; Bacteroidales; Unclassified; sfL; 46929; EF562564.1 gg_id: 236411 stable microbial consortia capable degrading complex organic matter paper pulp column clone CE_11 |
| grazer feces | 47150 | Bacteria; Bacteroidetes; Bacteroidales_SP; Bacteroidales_CL; Bacteroidales; Unclassified; smI; 47150; EU381902.1 gg_id: 270609 Rumen implicates Bacteroidetes major phylum rumen particulate phase fistulated Holstein heifer clone P5_K20 |
| grazer feces | 46260 | Bacteria; Bacteroidetes; Bacteroidetes_bacterium_PPf50E2_SP; E1-K9_CL; Bacteroidales; BA017_FM; sfB; 46260; EU774250.1 gg_id: 303921 Evolution mammals and their gut microbes Chimpanzee feces clone CHIMP12_d06_2 |
| grazer feces | 12404 | Bacteria; Bacteroidetes; F1CA7_SP; Cc180_CL; Flavobacteriales; Unclassified; sfA; 12404; DQ009081.1 gg_id: 122531 bacterioplankton clone SPOTSAPR01_5m232 |
| grazer feces | 12754 | Bacteria; Bacteroidetes; Flexibacterales_SP; Flexibacterales_CL; Flexibacterales; Flexibacter_FM; sfE; 12754; AF445737.1 gg_id: 32271 CFB group clone SM2G05 |
| grazer feces | 47408 | Bacteria; Bacteroidetes; p-2534-18B5_SP; Bacteroidales_CL; Bacteroidales; Unclassified; sfC; 47408; AF371924.1 gg_id: 16915 swine intestine clone p-2534-18B5 |
| grazer feces | 45928 | Bacteria; Bacteroidetes; RF14_SP; BS14_CL; Bacteroidales; Unclassified; sfA; 45928; EU470449.1 gg_id: 296079 Evolution mammals and their gut microbes Grevy's zebra feces clone GZ_aaa04e01 |
| grazer feces | 46184 | Bacteria; Bacteroidetes; RF14_SP; BS14_CL; Bacteroidales; Unclassified; sfA; 46184; EU470289.1 gg_id: 297914 Evolution mammals and their gut microbes Grevy's zebra feces clone GZ_aaa03b07 |
| grazer feces | 59417 | Bacteria; Chloroflexi; Anaerolineae_SP; Anaerolineae_CL; Anaerolineae_OR; Anaerolineae; shH; 59417; EU245158.1 gg_id: 247835 Miniprimer new lens viewing world hypersaline microbial mat clone MAT-CR-H3-C04 |
| grazer feces | 8050 | Bacteria; Firmicutes; Bacilli_SP; *Halobacillus*_CL; *Halobacillus*_OR; *Halobacillus*_FM; sfA; 8050; AY121439.1 gg_id: 63140 *Salibacillus* sp. str. YIM-kkny16 |
| grazer feces | 8805 | Bacteria; Firmicutes; Bacilli_SP; *Halobacillus*_CL; *Halobacillus*_OR; *Halobacillus*_FM; sfA; 8805; AY667497.1 gg_id: 103142 *Virgibacillus* sp. str. BH260 |
| grazer feces | 38670 | Bacteria; Firmicutes; Bacilli_SP; Planococcaceae_CL; Planococcaceae_OR; Planococcaceae; sfA; 38670; EU466021.1 gg_id: 291363 Evolution mammals and their gut microbes African elephant feces clone AFEL3_aao16a03 |
| grazer feces | 7600 | Bacteria; Firmicutes; Bacilli_SP; Planococcaceae_CL; Planococcaceae_OR; Planococcaceae; sfA; 7600; EU468081.1 gg_id: 297399 Evolution mammals and their gut microbes cheetah feces clone CE2_e01_2 |
| grazer feces | 7605 | Bacteria; Firmicutes; Bacilli_SP; Planococcaceae_CL; Planococcaceae_OR; Planococcaceae; sfA; 7605; EU466017.1 gg_id: 297626 Evolution mammals and their gut microbes African elephant feces clone AFEL3_aao15h09 |
| grazer feces | 7606 | Bacteria; Firmicutes; Bacilli_SP; Planococcaceae_CL; Planococcaceae_OR; Planococcaceae; sfA; 7606; EU466709.1 gg_id: 294326 Evolution mammals and their gut microbes argali sheep feces clone AS3_aao20c09 |
| grazer feces | 7620 | Bacteria; Firmicutes; Bacilli_SP; Planococcaceae_CL; Planococcaceae_OR; Planococcaceae; sfA; 7620; EU464669.1 gg_id: 290990 Evolution mammals and their gut microbes African elephant feces clone AFEL_aai32g10 |
| grazer feces | 7763 | Bacteria; Firmicutes; Bacilli_SP; Planococcaceae_CL; Planococcaceae_OR; Planococcaceae; sfA; 7763; AJ006086.1 gg_id: 14990 *Bacillus silvestris* HR3-23 |
| grazer feces | 7777 | Bacteria; Firmicutes; Bacilli_SP; Planococcaceae_CL; Planococcaceae_OR; Planococcaceae; sfA; 7777; EU464615.1 gg_id: 302384 Evolution mammals and their gut microbes African elephant feces clone AFEL_aai31h04 |
| grazer feces | 7787 | Bacteria; Firmicutes; Bacilli_SP; Planococcaceae_CL; Planococcaceae_OR; Planococcaceae; sfA; 7787; EU466769.1 gg_id: 291375 Evolution mammals and their gut microbes African elephant feces clone AFEL2_aao29c04 |

TABLE 2-continued

Grazer ID taxa
GRAZER IDENTIFIER TAXA

| Source | #OTU ID | Lineage for representative OUT; GenBank Accession No.; Greengenes ID# (gg_id); clone name or description |
|---|---|---|
| grazer feces | 7828 | Bacteria; Firmicutes; Bacilli_SP; Planococcaceae_CL; Planococcaceae_OR; Planococcaceae; sfA; 7828; DQ824627.1 gg_id: 193376 human fecal clone RL185_aaj70f09 |
| grazer feces | 7841 | Bacteria; Firmicutes; Bacilli_SP; Planococcaceae_CL; Planococcaceae_OR; Planococcaceae; sfA; 7841; EU465161.1 gg_id: 299996 Evolution mammals and their gut microbes African elephant feces clone AFYEL_aaj68h09 |
| grazer feces | 7845 | Bacteria; Firmicutes; Bacilli_SP; Planococcaceae_CL; Planococcaceae_OR; Planococcaceae; sfA; 7845; X70315.1 gg_id: 14993 Caryophanon tenue str. NCDO 2324 |
| grazer feces | 7892 | Bacteria; Firmicutes; Bacilli_SP; Planococcaceae_CL; Planococcaceae_OR; Planococcaceae; sfA; 7892; EU466719.1 gg_id: 290588 Evolution mammals and their gut microbes argali sheep feces clone AS3_aao20d10 |
| grazer feces | 7930 | Bacteria; Firmicutes; Bacilli_SP; Planococcaceae_CL; Planococcaceae_OR; Planococcaceae; sfA; 7930; EU466818.1 gg_id: 299913 Evolution mammals and their gut microbes African elephant feces clone AFEL2_aao29h04 |
| grazer feces | 7964 | Bacteria; Firmicutes; Bacilli_SP; Planococcaceae_CL; Planococcaceae_OR; Planococcaceae; sfA; 7964; EU464558.1 gg_id: 289900 Evolution mammals and their gut microbes African elephant feces clone AFEL_aai31a08 |
| grazer feces | 7966 | Bacteria; Firmicutes; Bacilli_SP; Planococcaceae_CL; Planococcaceae_OR; Planococcaceae; sfA; 7966; EU465967.1 gg_id: 302938 Evolution mammals and their gut microbes African elephant feces clone AFEL3_aao15a02 |
| grazer feces | 7981 | Bacteria; Firmicutes; Bacilli_SP; Planococcaceae_CL; Planococcaceae_OR; Planococcaceae; sfA; 7981; EU466839.1 gg_id: 287438 Evolution mammals and their gut microbes African elephant feces clone AFEL2_aao30b10 |
| grazer feces | 8034 | Bacteria; Firmicutes; Bacilli_SP; Planococcaceae_CL; Planococcaceae_OR; Planococcaceae; sfA; 8034; EU466899.1 gg_id: 291942 Evolution mammals and their gut microbes African elephant feces clone AFEL2_aao31a10 |
| grazer feces | 8096 | Bacteria; Firmicutes; Bacilli_SP; Planococcaceae_CL; Planococcaceae_OR; Planococcaceae; sfA; 8096; EU465742.1 gg_id: 301456 Evolution mammals and their gut microbes argali sheep feces clone AS2_aao34e07 |
| grazer feces | 8182 | Bacteria; Firmicutes; Bacilli_SP; Planococcaceae_CL; Planococcaceae_OR; Planococcaceae; sfA; 8182; EU466051.1 gg_id: 290668 Evolution mammals and their gut microbes African elephant feces clone AFEL3_aao16f08 |
| grazer feces | 8185 | Bacteria; Firmicutes; Bacilli_SP; Planococcaceae_CL; Planococcaceae_OR; Planococcaceae; sfA; 8185; EU464519.1 gg_id: 296718 Evolution mammals and their gut microbes African elephant feces clone AFEL_aai30e05 |
| grazer feces | 8202 | Bacteria; Firmicutes; Bacilli_SP; Planococcaceae_CL; Planococcaceae_OR; Planococcaceae; sfA; 8202; EU464523.1 gg_id: 299298 Evolution mammals and their gut microbes African elephant feces clone AFEL_aai30e10 |
| grazer feces | 8206 | Bacteria; Firmicutes; Bacilli_SP; Planococcaceae_CL; Planococcaceae_OR; Planococcaceae; sfA; 8206; EU464662.1 gg_id: 289396 Evolution mammals and their gut microbes African elephant feces clone AFEL_aai32f11 |
| grazer feces | 8212 | Bacteria; Firmicutes; Bacilli_SP; Planococcaceae_CL; Planococcaceae_OR; Planococcaceae; sfA; 8212; EU469349.1 gg_id: 300325 Evolution mammals and their gut microbes springbok feces clone SBK_d10_2 |
| grazer feces | 8216 | Bacteria; Firmicutes; Bacilli_SP; Planococcaceae_CL; Planococcaceae_OR; Planococcaceae; sfA; 8216; EU466702.1 gg_id: 290968 Evolution mammals and their gut microbes argali sheep feces clone AS3_aao20b09 |
| grazer feces | 8235 | Bacteria; Firmicutes; Bacilli_SP; Planococcaceae_CL; Planococcaceae_OR; Planococcaceae; sfA; 8235; EU464507.1 gg_id: 302131 Evolution mammals and their gut microbes African elephant feces clone AFEL_aai30c12 |
| grazer feces | 8242 | Bacteria; Firmicutes; Bacilli_SP; Planococcaceae_CL; Planococcaceae_OR; Planococcaceae; sfA; 8242; EU466932.1 gg_id: 287503 Evolution mammals and their gut microbes African elephant feces clone AFEL2_aao31e05 |
| grazer feces | 8270 | Bacteria; Firmicutes; Bacilli_SP; Planococcaceae_CL; Planococcaceae_OR; Planococcaceae; sfA; 8270; EU464619.1 gg_id: 288715 Evolution mammals and their gut microbes African elephant feces clone AFEL_aai31h12 |
| grazer feces | 8277 | Bacteria; Firmicutes; Bacilli_SP; Planococcaceae_CL; Planococcaceae_OR; Planococcaceae; sfA; 8277; EU464435.1 gg_id: 289502 Evolution mammals and their gut microbes African elephant feces clone AFEL_aai29b05 |
| grazer feces | 8280 | Bacteria; Firmicutes; Bacilli_SP; Planococcaceae_CL; Planococcaceae_OR; Planococcaceae; sfA; 8280; EU464595.1 gg_id: 294723 Evolution mammals and their gut microbes African elephant feces clone AFEL_aai31e08 |
| grazer feces | 8377 | Bacteria; Firmicutes; Bacilli_SP; Planococcaceae_CL; Planococcaceae_OR; Planococcaceae; sfA; 8377; AM773821.1 gg_id: 239221 Bacillus bhargavae |
| grazer feces | 8398 | Bacteria; Firmicutes; Bacilli_SP; Planococcaceae_CL; Planococcaceae_OR; Planococcaceae; sfA; 8398; AF548880.1 gg_id: 55578 Bacillus sp. str. CPB 9 |
| grazer feces | 8446 | Bacteria; Firmicutes; Bacilli_SP; Planococcaceae_CL; Planococcaceae_OR; Planococcaceae; sfA; 8446; EU466980.1 gg_id: 291933 Evolution mammals and their gut microbes African elephant feces clone AFEL2_aao32c04 |
| grazer feces | 8473 | Bacteria; Firmicutes; Bacilli_SP; Planococcaceae_CL; Planococcaceae_OR; Planococcaceae; sfA; 8473; EU465907.1 gg_id: 287559 Evolution mammals and their gut microbes African elephant feces clone AFEL3_aao13h04 |
| grazer feces | 8517 | Bacteria; Firmicutes; Bacilli_SP; Planococcaceae_CL; Planococcaceae_OR; Planococcaceae; sfA; 8517; EU458326.1 gg_id: 295839 Evolution mammals and their gut microbes spotted hyena feces clone HY1_e04 |
| grazer feces | 8540 | Bacteria; Firmicutes; Bacilli_SP; Planococcaceae_CL; Planococcaceae_OR; Planococcaceae; sfA; 8540; EU466031.1 gg_id: 287489 Evolution mammals and their gut microbes African elephant feces clone AFEL3_aao16c01 |
| grazer feces | 8553 | Bacteria; Firmicutes; Bacilli_SP; Planococcaceae_CL; Planococcaceae_OR; Planococcaceae; sfA; 8553; EU466929.1 gg_id: 300324 Evolution mammals and their gut microbes African elephant feces clone AFEL2_aao31e01 |
| grazer feces | 8558 | Bacteria; Firmicutes; Bacilli_SP; Planococcaceae_CL; Planococcaceae_OR; Planococcaceae; sfA; 8558; EU466799.1 gg_id: 295772 Evolution mammals and their gut microbes African elephant feces clone AFEL2_aao29f07 |
| grazer feces | 8571 | Bacteria; Firmicutes; Bacilli_SP; Planococcaceae_CL; Planococcaceae_OR; Planococcaceae; sfA; 8571; EU458313.1 gg_id: 297949 Evolution mammals and their gut microbes spotted hyena feces clone HY1_c01 |
| grazer feces | 8574 | Bacteria; Firmicutes; Bacilli_SP; Planococcaceae_CL; Planococcaceae_OR; Planococcaceae; sfA; 8574; EU464521.1 gg_id: 293562 Evolution mammals and their gut microbes African elephant feces clone AFEL_aai30e07 |
| grazer feces | 8587 | Bacteria; Firmicutes; Bacilli_SP; Planococcaceae_CL; Planococcaceae_OR; Planococcaceae; sfA; 8587; EU464448.1 gg_id: 287393 Evolution mammals and their gut microbes African elephant feces clone AFEL_aai29c12 |
| grazer feces | 8598 | Bacteria; Firmicutes; Bacilli_SP; Planococcaceae_CL; Planococcaceae_OR; Planococcaceae; sfA; 8598; EU249572.1 gg_id: 237395 Bacillus sp. str. DFVB3 |
| grazer feces | 8599 | Bacteria; Firmicutes; Bacilli_SP; Planococcaceae_CL; Planococcaceae_OR; Planococcaceae; sfA; 8599; EU458392.1 gg_id: 290167 Evolution mammals and their gut microbes spotted hyena feces clone HY1_b07_1 |
| grazer feces | 8613 | Bacteria; Firmicutes; Bacilli_SP; Planococcaceae_CL; Planococcaceae_OR; Planococcaceae; sfA; 8613; EU466827.1 gg_id: 293521 Evolution mammals and their gut microbes African elephant feces clone AFEL2_aao30a06 |
| grazer feces | 8744 | Bacteria; Firmicutes; Bacilli_SP; Planococcaceae_CL; Planococcaceae_OR; Planococcaceae; sfA; 8744; EU464657.1 gg_id: 301998 Evolution mammals and their gut microbes African elephant feces clone AFEL_aai32f06 |
| grazer feces | 8769 | Bacteria; Firmicutes; Bacilli_SP; Planococcaceae_CL; Planococcaceae_OR; Planococcaceae; sfA; 8769; EU469340.1 gg_id: 296844 Evolution mammals and their gut microbes springbok feces clone SBK_c09 |

TABLE 2-continued

Grazer ID taxa
GRAZER IDENTIFIER TAXA

| Source | #OTU ID | Lineage for representative OUT; GenBank Accession No.; Greengenes ID# (gg_id); clone name or description |
|---|---|---|
| grazer feces | 8794 | Bacteria; Firmicutes; Bacilli_SP; Planococcaceae_CL; Planococcaceae_OR; Planococcaceae; sfA; 8794; EU466806.1 gg_id: 290595 Evolution mammals and their gut microbes African elephant feces clone AFEL2__aao29g02 |
| grazer feces | 8803 | Bacteria; Firmicutes; Bacilli_SP; Planococcaceae_CL; Planococcaceae_OR; Planococcaceae; sfA; 8803; EU466880.1 gg_id: 290915 Evolution mammals and their gut microbes African elephant feces clone AFEL2__aao30g07 |
| grazer feces | 8842 | Bacteria; Firmicutes; Bacilli_SP; Planococcaceae_CL; Planococcaceae_OR; Planococcaceae; sfA; 8842; EU466821.1 gg_id: 287657 Evolution mammals and their gut microbes African elephant feces clone AFEL2__aao29h07 |
| grazer feces | 8851 | Bacteria; Firmicutes; Bacilli_SP; Planococcaceae_CL; Planococcaceae_OR; Planococcaceae; sfA; 8851; EU464563.1 gg_id: 294760 Evolution mammals and their gut microbes African elephant feces clone AFEL__aai31b03 |
| grazer feces | 8853 | Bacteria; Firmicutes; Bacilli_SP; Planococcaceae_CL; Planococcaceae_OR; Planococcaceae; sfA; 8853; EU458363.1 gg_id: 303075 Evolution mammals and their gut microbes spotted hyena feces clone HY1__d11__1 |
| grazer feces | 9370 | Bacteria; Firmicutes; Bacilli_SP; Planococcaceae_CL; Planococcaceae_OR; Planococcaceae; sfA; 9370; EU466607.1 gg_id: 297737 Evolution mammals and their gut microbes argali sheep feces clone AS3__aao18d01 |
| grazer feces | 8227 | Bacteria; Firmicutes; Bacilli_SP; Unclassified; Unclassified; Unclassified; sfA; 8227; DQ395945.1 gg_id: 155276 deep-sea octacoral clone ctg_CGOGA51 |
| grazer feces | 8679 | Bacteria; Firmicutes; Bacilli_SP; Unclassified; Unclassified; Unclassified; sfA; 8679; AJ236893.1 gg_id: 14638 *Bacillus* sp. IDA624 |
| grazer feces | 4021 | Bacteria; Firmicutes; Clostridia_SP; adhufec25_CL; Clostridiales; Unclassified; sfA; 4021; DQ795794.1 gg_id: 198960 human fecal clone RL245__aai82e05 |
| grazer feces | 35456 | Bacteria; Firmicutes; Clostridia_SP; BA49_CL; Clostridiales; Unclassified; sfA; 35456; EF098768.1 gg_id: 179614 mouse cecum clone SWPT16__aaa04f06 |
| grazer feces | 35641 | Bacteria; Firmicutes; Clostridia_SP; C18_h03_2_CL; Clostridiales; Unclassified; sfA; 35641; EU506189.1 gg_id: 276173 cecal contents *Mus musculus* strain C57BL/6J; MD18 clone MD18__aaa02g08 |
| grazer feces | 35941 | Bacteria; Firmicutes; Clostridia_SP; C18_h03_2_CL; Clostridiales; Unclassified; sfA; 35941; EF096279.1 gg_id: 185967 mouse cecum clone obob1__aaa04a07 |
| grazer feces | 36136 | Bacteria; Firmicutes; Clostridia_SP; C18_h03_2_CL; Clostridiales; Unclassified; sfA; 36136; EU509176.1 gg_id: 258539 cecal contents *Mus musculus* strain C57BL/6J; MD8 clone MD8__aap45d08 |
| grazer feces | 36239 | Bacteria; Firmicutes; Clostridia_SP; C18_h03_2_CL; Clostridiales; Unclassified; sfA; 36239; EU506172.1 gg_id: 265423 cecal contents *Mus musculus* strain C57BL/6J; MD18 clone MD18__aaa02a05 |
| grazer feces | 4179 | Bacteria; Firmicutes; Clostridia_SP; C22_e17_CL; Clostridiales; M1_b07_2_FM; sfA; 4179; EU511169.1 gg_id: 271815 cecal contents *Mus musculus* strain C57BL/6J; WD7 clone WD7__aal03g08 |
| grazer feces | 38094 | Bacteria; Firmicutes; Clostridia_SP; Catabacter_CL; Catabacter_OR; Catabacter_FM; sfI; 38094; DQ815454.1 gg_id: 164595 mouse cecum clone aab48f09 |
| grazer feces | 36463 | Bacteria; Firmicutes; Clostridia_SP; Clostridiales_CL; Clostridiales; *Acetivibrio*_FM; sfD; 36463; AY916331.1 gg_id: 114115 human stool clone C288 |
| grazer feces | 39405 | Bacteria; Firmicutes; Clostridia_SP; Clostridiales_CL; Clostridiales; Clostridiaceae; sfA; 39405; DQ817030.1 gg_id: 164033 zebrafish gut microbiota-colonized mouse cecum clone aaa94h02 |
| grazer feces | 35359 | Bacteria; Firmicutes; Clostridia_SP; Clostridiales_CL; Clostridiales; *Clostridium*_FM; sfB; 35359; AY244908.1 gg_id: 85153 cow rumen clone BF30 |
| grazer feces | 35364 | Bacteria; Firmicutes; Clostridia_SP; Clostridiales_CL; Clostridiales; *Clostridium*_FM; sfB; 35364; EU506544.1 gg_id: 270066 cecal contents *Mus musculus* strain C57BL/6J; MD19 clone MD19__aaa03g02 |
| grazer feces | 35563 | Bacteria; Firmicutes; Clostridia_SP; Clostridiales_CL; Clostridiales; *Clostridium*_FM; sfB; 35563; EU465687.1 gg_id: 302641 Evolution mammals and their gut microbes argali sheep feces clone AS2__aao33e07 |
| grazer feces | 35598 | Bacteria; Firmicutes; Clostridia_SP; Clostridiales_CL; Clostridiales; *Clostridium*_FM; sfB; 35598; EU504457.1 gg_id: 271490 cecal contents *Mus musculus* strain C57BL/6J; CRWD6 clone CRWD6__aaa04g02 |
| grazer feces | 35822 | Bacteria; Firmicutes; Clostridia_SP; Clostridiales_CL; Clostridiales; *Clostridium*_FM; sfB; 35822; EU506923.1 gg_id: 273345 cecal contents *Mus musculus* strain C57BL/6J; MD21 clone MD21__aar08d09 |
| grazer feces | 6945 | Bacteria; Firmicutes; Clostridia_SP; Clostridiales_CL; Clostridiales; *Eubacterium*_FM; sfA; 6945; EU506309.1 gg_id: 268204 cecal contents *Mus musculus* strain C57BL/6J; MD18 clone MD18__aap63a08 |
| grazer feces | 41631 | Bacteria; Firmicutes; Clostridia_SP; Clostridiales_CL; Clostridiales; *Eubacterium*_FM; sfO; 41631; EU468659.1 gg_id: 301126 Evolution mammals and their gut microbes okapi feces clone OK2__g08 |
| grazer feces | 38022 | Bacteria; Firmicutes; Clostridia_SP; Clostridiales_CL; Clostridiales; *Ruminococcus*_FM; sfA; 38022; DQ793417.1 gg_id: 177697 human fecal clone RL199__aaj43e03 |
| grazer feces | 38154 | Bacteria; Firmicutes; Clostridia_SP; Clostridiales_CL; Clostridiales; *Ruminococcus*_FM; sfA; 38154; EU467336.1 gg_id: 297875 Evolution mammals and their gut microbes chimpanzee feces clone CHIMP1__c02 |
| grazer feces | 38166 | Bacteria; Firmicutes; Clostridia_SP; Clostridiales_CL; Clostridiales; *Ruminococcus*_FM; sfA; 38166; EF096604.1 gg_id: 192848 mouse cecum clone SWPT11__aaa01g04 |
| grazer feces | 38201 | Bacteria; Firmicutes; Clostridia_SP; Clostridiales_CL; Clostridiales; *Ruminococcus*_FM; sfA; 38201; EU461043.1 gg_id: 291053 Evolution mammals and their gut microbes red kangaroo feces clone KO1__aai43a03 |
| grazer feces | 38297 | Bacteria; Firmicutes; Clostridia_SP; Clostridiales_CL; Clostridiales; *Ruminococcus*_FM; sfA; 38297; EU472119.1 gg_id: 296626 Evolution mammals and their gut microbes francois langur feces clone FL_1aaa02g05 |
| grazer feces | 38697 | Bacteria; Firmicutes; Clostridia_SP; Clostridiales_CL; Clostridiales; *Ruminococcus*_FM; sfA; 38697; DQ015653.1 gg_id: 132635 mouse cecum clone M3__f10__3 |
| grazer feces | 38829 | Bacteria; Firmicutes; Clostridia_SP; Clostridiales_CL; Clostridiales; *Ruminococcus*_FM; sfA; 38829; AY916162.1 gg_id: 114069 human transverse colon biopsy clone M511 |
| grazer feces | 38601 | Bacteria; Firmicutes; Clostridia_SP; Clostridiales_CL; Clostridiales; *Ruminococcus*_FM; sfC; 38601; EU467635.1 gg_id: 288877 Evolution mammals and their gut microbes naked mole-rat feces clone molerat__2g12 |
| grazer feces | 38716 | Bacteria; Firmicutes; Clostridia_SP; Clostridiales_CL; Clostridiales; *Ruminococcus*_FM; sfC; 38716; EU467689.1 gg_id: 297344 Evolution mammals and their gut microbes naked mole-rat feces clone molerat__2e03 |
| grazer feces | 38817 | Bacteria; Firmicutes; Clostridia_SP; Clostridiales_CL; Clostridiales; *Ruminococcus*_FM; sfC; 38817; EU463046.1 gg_id: 291553 Evolution mammals and their gut microbes naked mole-rat feces clone molerat__aai69a02 |
| grazer feces | 38931 | Bacteria; Firmicutes; Clostridia_SP; Clostridiales_CL; Clostridiales; *Ruminococcus*_FM; sfC; 38931; EU463250.1 gg_id: 288946 Evolution mammals and their gut microbes naked mole-rat feces clone molerat__aai72c11 |
| grazer feces | 3264 | Bacteria; Firmicutes; Clostridia_SP; Clostridiales_CL; Clostridiales; Unclassified; sfA; 3264; EU470125.1 gg_id: 294416 Evolution mammals and their gut microbes trancaspain urial feces clone TU2__aaa04a03 |

TABLE 2-continued

Grazer ID taxa
GRAZER IDENTIFIER TAXA

| Source | #OTU ID | Lineage for representative OUT; GenBank Accession No.; Greengenes ID# (gg_id); clone name or description |
|---|---|---|
| grazer feces | 4196 | Bacteria; Firmicutes; Clostridia_SP; Clostridiales_CL; Clostridiales; Unclassified; sfA; 4196; AY991751.1 gg_id: 130076 mouse cecum clone C20__c10 |
| grazer feces | 4204 | Bacteria; Firmicutes; Clostridia_SP; Clostridiales_CL; Clostridiales; Unclassified; sfA; 4204; AF371580.1 gg_id: 22721 swine intestine clone p-265-o5 |
| grazer feces | 4355 | Bacteria; Firmicutes; Clostridia_SP; Clostridiales_CL; Clostridiales; Unclassified; sfA; 4355; EU381827.1 gg_id: 265665 Rumen implicates Bacteroidetes major phylum rumen particulate phase fistulated Holstein heifer clone P5__H01 |
| grazer feces | 4631 | Bacteria; Firmicutes; Clostridia_SP; Clostridiales_CL; Clostridiales; Unclassified; sfA; 4631; EU460099.1 gg_id: 301194 Evolution mammals their gut microbes eastern black and white colobus feces clone COL__aai14f01 |
| grazer feces | 34857 | Bacteria; Firmicutes; Clostridia_SP; Clostridiales_CL; Clostridiales; Unclassified; sfB; 34857; EU468589.1 gg_id: 295631 Evolution mammals and their gut microbes okapi feces clone OK1__e09_3 |
| grazer feces | 35077 | Bacteria; Firmicutes; Clostridia_SP; Clostridiales_CL; Clostridiales; Unclassified; sfB; 35077; DQ455828.1 gg_id: 158836 pre-adolescent turkey cecum clone CFT19A7 |
| grazer feces | 35097 | Bacteria; Firmicutes; Clostridia_SP; Clostridiales_CL; Clostridiales; Unclassified; sfB; 35097; AY854337.1 gg_id: 110859 herbivore gastrointestinal tract clone Thompsons50 |
| grazer feces | 35206 | Bacteria; Firmicutes; Clostridia_SP; Clostridiales_CL; Clostridiales; Unclassified; sfB; 35206; DQ815474.1 gg_id: 164242 mouse cecum clone aab41c04 |
| grazer feces | 35252 | Bacteria; Firmicutes; Clostridia_SP; Clostridiales_CL; Clostridiales; Unclassified; sfB; 35252; EU472629.1 gg_id: 293575 Evolution mammals and their gut microbes Angola colobus feces clone EAC_2__aaa04d02 |
| grazer feces | 35286 | Bacteria; Firmicutes; Clostridia_SP; Clostridiales_CL; Clostridiales; Unclassified; sfB; 35286; EU466096.1 gg_id: 287842 Evolution mammals and their gut microbes bighorn sheep feces clone BH1__aao25g07 |
| grazer feces | 35314 | Bacteria; Firmicutes; Clostridia_SP; Clostridiales_CL; Clostridiales; Unclassified; sfB; 35314; EU470142.1 gg_id: 292360 Evolution mammals and their gut microbes trancaspain urial feces clone TU2__aaa01d02 |
| grazer feces | 35449 | Bacteria; Firmicutes; Clostridia_SP; Clostridiales_CL; Clostridiales; Unclassified; sfB; 35449; EU463435.1 gg_id: 299836 Evolution mammals and their gut microbes domesticated horse feces clone horsem__aai93h06 |
| grazer feces | 35483 | Bacteria; Firmicutes; Clostridia_SP; Clostridiales_CL; Clostridiales; Unclassified; sfB; 35483; EU466460.1 gg_id: 302489 Evolution mammals and their gut microbes bighorn sheep feces clone BH2__aao24b03 |
| grazer feces | 35523 | Bacteria; Firmicutes; Clostridia_SP; Clostridiales_CL; Clostridiales; Unclassified; sfB; 35523; EU468867.1 gg_id: 290041 Evolution mammals and their gut microbes Speke's gazelle feces clone SP2__c12 |
| grazer feces | 35609 | Bacteria; Firmicutes; Clostridia_SP; Clostridiales_CL; Clostridiales; Unclassified; sfB; 35609; DQ801347.1 gg_id: 181030 human fecal clone RL388__aao94c11 |
| grazer feces | 36096 | Bacteria; Firmicutes; Clostridia_SP; Clostridiales_CL; Clostridiales; Unclassified; sfB; 36096; EF445203.1 gg_id: 216747 rabbit cecum clone NED3G12 |
| grazer feces | 36097 | Bacteria; Firmicutes; Clostridia_SP; Clostridiales_CL; Clostridiales; Unclassified; sfB; 36097; EU465604.1 gg_id: 291988 Evolution mammals and their gut microbes argali sheep feces clone AS1__aao39c10.Contig1 |
| grazer feces | 40263 | Bacteria; Firmicutes; Clostridia_SP; Clostridiales_CL; Clostridiales; Unclassified; sfC; 40263; EU468892.1 gg_id: 293728 Evolution mammals and their gut microbes Speke's gazelle feces clone SP2__g01 |
| grazer feces | 40347 | Bacteria; Firmicutes; Clostridia_SP; Clostridiales_CL; Clostridiales; Unclassified; sfC; 40347; AF371776.1 gg_id: 41287 swine intestine clone p-1651-c5 |
| grazer feces | 40353 | Bacteria; Firmicutes; Clostridia_SP; Clostridiales_CL; Clostridiales; Unclassified; sfC; 40353; EU460995.1 gg_id: 298877 Evolution mammals and their gut microbes red kangaroo feces clone KO1__aai41h03 |
| grazer feces | 40437 | Bacteria; Firmicutes; Clostridia_SP; Clostridiales_CL; Clostridiales; Unclassified; sfC; 40437; DQ805141.1 gg_id: 182044 human fecal clone RL249__aaj81h07 |
| grazer feces | 40698 | Bacteria; Firmicutes; Clostridia_SP; Clostridiales_CL; Clostridiales; Unclassified; sfC; 40698; DQ801064.1 gg_id: 193895 human fecal clone RL387__aao91f04 |
| grazer feces | 3185 | Bacteria; Firmicutes; Clostridia_SP; Clostridiales_CL; Clostridiales; Unclassified; sfE; 3185; EU464533.1 gg_id: 293841 Evolution mammals and their gut microbes African elephant feces clone AFEL__aai30f09 |
| grazer feces | 4255 | Bacteria; Firmicutes; Clostridia_SP; Clostridiales_CL; Clostridiales; Unclassified; sfE; 4255; EU461525.1 gg_id: 295410 Evolution mammals and their gut microbes black rhinoceros feces clone RH__aaj91f05 |
| grazer feces | 35929 | Bacteria; Firmicutes; Clostridia_SP; Clostridiales_CL; Clostridiales; Unclassified; sfG; 35929; EU469833.1 gg_id: 293546 Evolution mammals and their gut microbes western lowland gorilla feces clone GOR__aag72a09 |
| grazer feces | 36636 | Bacteria; Firmicutes; Clostridia_SP; Clostridiales_CL; Clostridiales; Unclassified; sfO; 36636; DQ795747.1 gg_id: 198826 human fecal clone RL245__aai81g02 |
| grazer feces | 40436 | Bacteria; Firmicutes; Clostridia_SP; Clostridiales_CL; Clostridiales; Unclassified; sfP; 40436; AY916333.1 gg_id: 114325 human stool clone C342 |
| grazer feces | 37719 | Bacteria; Firmicutes; Clostridia_SP; Clostridiales_CL; Clostridiales; Unclassified; sfY; 37719; AB185742.1 gg_id: 107605 rumen clone U29-A04 |
| grazer feces | 37906 | Bacteria; Firmicutes; Clostridia_SP; Clostridiales_CL; Clostridiales; Unclassified; sgT; 37906; EU465635.1 gg_id: 293025 Evolution mammals and their gut microbes argali sheep feces clone AS1__aao40d08.Contig1 |
| grazer feces | 201 | Bacteria; Firmicutes; Clostridia_SP; Clostridiales_CL; Clostridiales; Unclassified; shR; 201; EU344459.1 gg_id: 275693 Foregut Fermentation Birds: Hoatzin Crop Supports Case Convergence Ruminants adult hoatzin crop clone hoa33__76D10 |
| grazer feces | 40528 | Bacteria; Firmicutes; Clostridia_SP; Clostridiales_CL; Clostridiales; Unclassified; shU; 40528; AF050581.1 gg_id: 16062 contaminated aquifer clone WCHB1-49 |
| grazer feces | 41321 | Bacteria; Firmicutes; Clostridia_SP; Clostridiales_CL; Clostridiales; Unclassified; siU; 41321; AF050582.1 gg_id: 16073 contaminated aquifer clone WCHB1-54 |
| grazer feces | 35008 | Bacteria; Firmicutes; Clostridia_SP; Clostridiales_CL; Clostridiales; Unclassified; smO; 35008; EU466082.1 gg_id: 302431 Evolution mammals and their gut microbes bighorn sheep feces clone BH1__aao25e07 |
| grazer feces | 6778 | Bacteria; Firmicutes; Clostridia_SP; Clostridiales_CL; Clostridiales; Unclassified; snG; 6778; EU344509.1 gg_id: 262457 Foregut Fermentation Birds: Hoatzin Crop Supports Case Convergence Ruminants adult hoatzin crop clone hoa33__13E02 |
| grazer feces | 2859 | Bacteria; Firmicutes; Clostridia_SP; Clostridiales_CL; Clostridiales; Unclassified; spI; 2859; EU471660.1 gg_id: 293637 Evolution mammals and their gut microbes Asiatic elephant feces clone AE1__aaa02g07 |
| grazer feces | 4973 | Bacteria; Firmicutes; Clostridia_SP; F24-F10_CL; Clostridiales; Unclassified; sfA; 4973; EU344478.1 gg_id: 263050 Foregut Fermentation Birds: Hoatzin Crop Supports Case Convergence Ruminants adult hoatzin crop clone hoa34__57A08 |

TABLE 2-continued

Grazer ID taxa
GRAZER IDENTIFIER TAXA

| Source | #OTU ID | Lineage for representative OUT; GenBank Accession No.; Greengenes ID# (gg__id); clone name or description |
|---|---|---|
| grazer feces | 5354 | Bacteria; Firmicutes; Clostridia_SP; F24-F10__CL; Clostridiales; Unclassified; sfA; 5354; EU466207.1 gg__id: 288489 Evolution mammals and their gut microbes bighorn sheep feces clone BH1__aao28a07 |
| grazer feces | 3195 | Bacteria; Firmicutes; Clostridia_SP; HuDI84__CL; Clostridiales; Unclassified; sfA; 3195; EU460106.1 gg__id: 290929 Evolution mammals their gut microbes eastern black and white colobus feces clone COL__aai14g02 |
| grazer feces | 35741 | Bacteria; Firmicutes; Clostridia_SP; NED2F10__CL; Clostridiales; Unclassified; sfA; 35741; EU509986.1 gg__id: 260248 cecal contents *Mus musculus* strain C57BL/6J; WD1 clone WD1__aaf15b06 |
| grazer feces | 35988 | Bacteria; Firmicutes; Clostridia_SP; NED2F10__CL; Clostridiales; Unclassified; sfA; 35988; DQ015142.1 gg__id: 135795 mouse cecum clone M2__b01__1 |
| grazer feces | 38115 | Bacteria; Firmicutes; Clostridia_SP; p-4154-6Wa5__CL; Clostridiales; C10_I02__FM; sfB; 38115; EU461085.1 gg__id: 297202 Evolution mammals and their gut microbes red kangaroo feces clone KO1__aai43h06 |
| grazer feces | 41084 | Bacteria; Firmicutes; Clostridia_SP; Peptostreptococcaceae__CL; Peptostreptococcaceae__OR; Peptostreptococcaceae; sfA; 41084; EF604614.1 gg__id: 229761 *Salmonella typhimurium* Exploits inflammation Compete Intestinal Microbiota mouse cecum clone 16saw39-1a07.w2k |
| grazer feces | 40579 | Bacteria; Firmicutes; Clostridia_SP; Peptostreptococcaceae__CL; Peptostreptococcaceae__OR; Peptostreptococcaceae; siU; 40579; EU464127.1 gg__id: 299087 Evolution mammals and their gut microbes reticulated giraffe feces clone gir__aah94d05 |
| grazer feces | 42217 | Bacteria; Firmicutes; Clostridia_SP; RF30__CL; Clostridiales; RF6__FM; sfA; 42217; EF445201.1 gg__id: 210361 rabbit cecum clone NED2G1 |
| grazer feces | 42218 | Bacteria; Firmicutes; Clostridia_SP; RF30__CL; Clostridiales; RF6__FM; sfA; 42218; EU463538.1 gg__id: 303030 Evolution mammals and their gut microbes domesticated horse feces clone horsem__aai95g03 |
| grazer feces | 42298 | Bacteria; Firmicutes; Clostridia_SP; RF30__CL; Clostridiales; RF6__FM; sfA; 42298; DQ394605.1 gg__id: 152014 -Arctic peninsula Svalbard Norway determined genes and rumen isolates reindeer on natural summer pasture clone NP43 |
| grazer feces | 42300 | Bacteria; Firmicutes; Clostridia_SP; RF30__CL; Clostridiales; RF6__FM; sfA; 42300; DQ115994.1 gg__id: 132122 bovine teat canal clone B-75 |
| grazer feces | 42356 | Bacteria; Firmicutes; Clostridia_SP; RF30__CL; Clostridiales; RF6__FM; sfA; 42356; EU464281.1 gg__id: 292672 Evolution mammals and their gut microbes hamadryas baboon feces clone AFBAB__aai01f07 |
| grazer feces | 42482 | Bacteria; Firmicutes; Clostridia_SP; RF30__CL; Clostridiales; RF6__FM; sfA; 42482; EU381962.1 gg__id: 259550 Rumen implicates Bacteroidetes major phylum rumen particulate phase fistulated Holstein heifer clone P5__A23 |
| grazer feces | 42605 | Bacteria; Firmicutes; Clostridia_SP; RF30__CL; Clostridiales; RF6__FM; sfA; 42605; EF436433.1 gg__id: 215731 library-based ruminal water buffalo (*Bubalus bubalis*) rumen fluid clone BRC147 |
| grazer feces | 42618 | Bacteria; Firmicutes; Clostridia_SP; RF30__CL; Clostridiales; RF6__FM; sfA; 42618; DQ327572.1 gg__id: 146754 Metagenomic gut microbiome healthy human stool clone EB56 |
| grazer feces | 42750 | Bacteria; Firmicutes; Clostridia_SP; RF30__CL; Clostridiales; RF6__FM; sfA; 42750; DQ394660.1 gg__id: 153291 on -Arctic peninsula Svalbard Norway determined genes and rumen isolates reindeer fed pelleted concentrates (RF-80) clone AF11 |
| grazer feces | 42783 | Bacteria; Firmicutes; Clostridia_SP; RF30__CL; Clostridiales; RF6__FM; sfA; 42783; DQ394665.1 gg__id: 155763 on -Arctic peninsula Svalbard Norway determined genes and rumen isolates reindeer fed pelleted concentrates (RF-80) clone AF18A |
| grazer feces | 42926 | Bacteria; Firmicutes; Clostridia_SP; RF30__CL; Clostridiales; RF6__FM; sfA; 42926; DQ394637.1 gg__id: 152278 -Arctic peninsula Svalbard Norway determined genes and rumen isolates reindeer on natural late summer pasture clone SR7 |
| grazer feces | 42941 | Bacteria; Firmicutes; Clostridia_SP; RF30__CL; Clostridiales; RF6__FM; sfA; 42941; EF445156.1 gg__id: 210895 rabbit cecum clone NED3A9 |
| grazer feces | 43037 | Bacteria; Firmicutes; Clostridia_SP; RF30__CL; Clostridiales; RF6__FM; sfA; 43037; DQ394662.1 gg__id: 154424 on -Arctic peninsula Svalbard Norway determined genes and rumen isolates reindeer fed pelleted concentrates (RF-80) clone AF59 |
| grazer feces | 43067 | Bacteria; Firmicutes; Clostridia_SP; RF30__CL; Clostridiales; RF6__FM; sfA; 43067; EF686583.1 gg__id: 240746 Sequences Manifest Rumen Yunnan Yel Cattle (*Bos Taurus*) rumen fluid clone YNRC72 |
| grazer feces | 43038 | Bacteria; Firmicutes; Clostridia_SP; RF30__CL; Clostridiales; RF6__FM; sfB; 43038; DQ394636.1 gg__id: 152890 -Arctic peninsula Svalbard Norway determined genes and rumen isolates reindeer on natural late summer pasture clone SR17 |
| grazer feces | 42078 | Bacteria; Firmicutes; Clostridia_SP; RF30__CL; Clostridiales; RF6__FM; sfC; 42078; AB288899.1 gg__id: 201543 termite gut homogenate clone BOf4-02 |
| grazer feces | 6184 | Bacteria; Firmicutes; Clostridia_SP; Rs-F27__CL; Clostridiales; Unclassified; sfA; 6184; EU509245.1 gg__id: 273136 cecal contents *Mus musculus* strain C57BL/6J; MD8 clone MD8__aap46e08 |
| grazer feces | 7327 | Bacteria; Firmicutes; Clostridia_SP; Rs-F27__CL; Clostridiales; Unclassified; sfA; 7327; EU505613.1 gg__id: 272216 cecal contents *Mus musculus* strain C57BL/6J; myd5 clone myd5__aaa03d09 |
| grazer feces | 7571 | Bacteria; Firmicutes; Clostridia_SP; Rs-F27__CL; Clostridiales; Unclassified; sfA; 7571; EU507989.1 gg__id: 258826 cecal contents *Mus musculus* strain C57BL/6J; MD25 clone MD25__aaa01d05 |
| grazer feces | 41947 | Bacteria; Firmicutes; Clostridia_SP; SHA-32__CL; Unclassified; Unclassified; sfA; 41947; AB270037.1 gg__id: 168506 Influence temperature and humidity on heifers rumen contents Holstein heifer (*Bos taurus*) clone T28H60F25 |
| grazer feces | 42035 | Bacteria; Firmicutes; Clostridia_SP; SHA-32__CL; Unclassified; Unclassified; sfA; 42035; EF686567.1 gg__id: 238421 Sequences Manifest Rumen Yunnan Yel Cattle (*Bos Taurus*) rumen fluid clone YNRC56 |
| grazer feces | 42094 | Bacteria; Firmicutes; Clostridia_SP; SHA-32__CL; Unclassified; Unclassified; sfA; 42094; AB185594.1 gg__id: 103532 rumen clone F24-C04 |
| grazer feces | 42110 | Bacteria; Firmicutes; Clostridia_SP; SHA-32__CL; Unclassified; Unclassified; sfA; 42110; AY854306.1 gg__id: 109894 herbivore gastrointestinal tract clone Thompsons10a |
| grazer feces | 42268 | Bacteria; Firmicutes; Clostridia_SP; SHA-32__CL; Unclassified; Unclassified; sfA; 42268; DQ394596.1 gg__id: 152810 -Arctic peninsula Svalbard Norway determined genes and rumen isolates reindeer on natural summer pasture clone NP45 |
| grazer feces | 42410 | Bacteria; Firmicutes; Clostridia_SP; SHA-32__CL; Unclassified; Unclassified; sfA; 42410; EU459464.1 gg__id: 290585 Evolution mammals and their gut microbes capybara feces clone CAP__aah97f05 |
| grazer feces | 42787 | Bacteria; Firmicutes; Clostridia_SP; SHA-32__CL; Unclassified; Unclassified; sfA; 42787; AB270133.1 gg__id: 168877 Influence temperature and humidity on heifers rumen contents Holstein heifer (*Bos taurus*) clone T33H60F63 |
| grazer feces | 42837 | Bacteria; Firmicutes; Clostridia_SP; SHA-32__CL; Unclassified; Unclassified; sfA; 42837; EU475345.1 gg__id: 288441 Evolution mammals and their gut microbes rock hyrax feces clone RHSD__aaa01e03 |

TABLE 2-continued

Grazer ID taxa
GRAZER IDENTIFIER TAXA

| Source | #OTU ID | Lineage for representative OUT; GenBank Accession No.; Greengenes ID# (gg_id); clone name or description |
|---|---|---|
| grazer feces | 42854 | Bacteria; Firmicutes; Clostridia_SP; SHA-32_CL; Unclassified; Unclassified; sfA; 42854; EU381606.1 gg_id: 270690 Rumen implicates Bacteroidetes major particulate phylum rumen liquid phase fistulated Holstein heifer clone L7A_F04 |
| grazer feces | 37904 | Bacteria; Firmicutes; Clostridia_SP; SR5_CL; Clostridiales; Unclassified; sfJ; 37904; DQ797643.1 gg_id: 174182 human fecal clone RL206_aaj14b07 |
| grazer feces | 38302 | Bacteria; Firmicutes; Clostridia_SP; UC7-69_CL; Clostridiales; Unclassified; sfA; 38302; EU468471.1 gg_id: 297060 Evolution mammals and their gut microbes okapi feces clone OK1_d07 |
| grazer feces | 38468 | Bacteria; Firmicutes; Clostridia_SP; UC7-69_CL; Clostridiales; Unclassified; sfA; 38468; AB192045.1 gg_id: 144669 termite gut homogenate clone M2PT2-11 |
| grazer feces | 42081 | Bacteria; Firmicutes; Clostridia_SP; Unclassified; Unclassified; Unclassified; sfA; 42081; EU381585.1 gg_id: 277400 Rumen implicates Bacteroidetes major particulate phylum rumen liquid phase fistulated Holstein heifer clone L7B_A11 |
| grazer feces | 42177 | Bacteria; Firmicutes; Clostridia_SP; Unclassified; Unclassified; Unclassified; sfA; 42177; EU382054.1 gg_id: 270654 Rumen implicates Bacteroidetes major phylum rumen particulate phase fistulated Holstein heifer clone P5_O12 |
| grazer feces | 42250 | Bacteria; Firmicutes; Clostridia_SP; Unclassified; Unclassified; Unclassified; sfA; 42250; AB270086.1 gg_id: 171932 Influence temperature and humidity on heifers rumen contents Holstein heifer (*Bos taurus*) clone T33H60F10 |
| grazer feces | 42287 | Bacteria; Firmicutes; Clostridia_SP; Unclassified; Unclassified; Unclassified; sfA; 42287; DQ806377.1 gg_id: 174033 human fecal clone RL186_aan91d11 |
| grazer feces | 42311 | Bacteria; Firmicutes; Clostridia_SP; Unclassified; Unclassified; Unclassified; sfA; 42311; AB270058.1 gg_id: 167555 Influence temperature and humidity on heifers rumen contents Holstein heifer (*Bos taurus*) clone T28H60F53 |
| grazer feces | 42383 | Bacteria; Firmicutes; Clostridia_SP; Unclassified; Unclassified; Unclassified; sfA; 42383; EU381688.1 gg_id: 258556 Rumen implicates Bacteroidetes major particulate phylum rumen liquid phase fistulated Holstein heifer clone L3A_A03 |
| grazer feces | 42408 | Bacteria; Firmicutes; Clostridia_SP; Unclassified; Unclassified; Unclassified; sfA; 42408; AY858392.2 gg_id: 111550 gastrointestinal tract Grant's gazelle clone GRANT60 |
| grazer feces | 42446 | Bacteria; Firmicutes; Clostridia_SP; Unclassified; Unclassified; Unclassified; sfA; 42446; AB270042.1 gg_id: 172652 Influence temperature and humidity on heifers rumen contents Holstein heifer (*Bos taurus*) clone T28H60F30 |
| grazer feces | 42517 | Bacteria; Firmicutes; Clostridia_SP; Unclassified; Unclassified; Unclassified; sfA; 42517; EU381933.1 gg_id: 262286 Rumen implicates Bacteroidetes major phylum rumen particulate phase fistulated Holstein heifer clone P5_E07 |
| grazer feces | 42563 | Bacteria; Firmicutes; Clostridia_SP; Unclassified; Unclassified; Unclassified; sfA; 42563; EU344390.1 gg_id: 258986 Foregut Fermentation Birds: Hoatzin Crop Supports Case Convergence Ruminants adult hoatzin crop clone hoa2_42c07 |
| grazer feces | 42670 | Bacteria; Firmicutes; Clostridia_SP; Unclassified; Unclassified; Unclassified; sfA; 42670; AB185569.1 gg_id: 106984 rumen clone F23-H07 |
| grazer feces | 42903 | Bacteria; Firmicutes; Clostridia_SP; Unclassified; Unclassified; Unclassified; sfA; 42903; AB185682.1 gg_id: 104046 rumen clone U28-C04 |
| grazer feces | 43070 | Bacteria; Firmicutes; Clostridia_SP; Unclassified; Unclassified; Unclassified; sfA; 43070; AY858426.2 gg_id: 111485 gastrointestinal tract Grant's gazelle clone GRANT49 |
| grazer feces | 6421 | Bacteria; Firmicutes; Clostridia_SP; Unclassified; Unclassified; Unclassified; sfA; 6421; DQ116004.1 gg_id: 133222 bovine teat canal clone D-45 |
| grazer feces | 17068 | Bacteria; Firmicutes; Clostridia_SP; Unclassified; Unclassified; Unclassified; sfM; 17068; EU471521.1 gg_id: 288726 Evolution mammals and their gut microbes Asiatic elephant feces clone AE1_aaa01g09 |
| grazer feces | 40223 | Bacteria; Firmicutes; Mollicutes_SP; RF39_CL; adhufec202_OR; FM046_FM; sfA; 40223; EU381514.1 gg_id: 269742 Rumen implicates Bacteroidetes major particulate phylum rumen liquid phase fistulated Holstein heifer clone L7B_G03 |
| grazer feces | 40474 | Bacteria; Firmicutes; Mollicutes_SP; RF39_CL; p-3870-23G5_OR; Unclassified; sfA; 40474; EF445197.1 gg_id: 209031 rabbit cecum clone NED1F6 |
| grazer feces | 40417 | Bacteria; Firmicutes; Mollicutes_SP; RF39_CL; Unclassified; Unclassified; sfA; 40417; AF371529.1 gg_id: 42395 swine intestine clone p-3133-SwA3 |
| grazer feces | 40488 | Bacteria; Firmicutes; Mollicutes_SP; RF39_CL; Unclassified; Unclassified; sfA; 40488; EU462656.1 gg_id: 287460 Evolution mammals and their gut microbes Sumatran orangutan feces clone orang2_aai66g12 |
| grazer feces | 41289 | Bacteria; Firmicutes; Mollicutes_SP; RF39_CL; Unclassified; Unclassified; sfA; 41289; EU381705.1 gg_id: 266198 Rumen implicates Bacteroidetes major particulate phylum rumen liquid phase fistulated Holstein heifer clone L7B_D05 |
| grazer feces | 31478 | Bacteria; LD1; Unclassified; Unclassified; Unclassified; Unclassified; sfD; 31478; EU385692.1 gg_id: 258278 Stratified microbes sediments Core MD05-2896 subseafloor sediment South China Sea clone MD2896-B76 |
| grazer feces | 32433 | Bacteria; *Moorella*; Unclassified; Unclassified; Unclassified; Unclassified; sfA; 32433; AJ633105.1 gg_id: 107449 DSM 12993 |
| grazer feces | 32899 | Bacteria; *Moorella*; Unclassified; Unclassified; Unclassified; Unclassified; sfA; 32899; AY766037.1 gg_id: 108103 *Moorella* sp. str. AIP 246.00 |
| grazer feces | 32967 | Bacteria; *Moorella*; Unclassified; Unclassified; Unclassified; Unclassified; sfA; 32967; AJ242494.1 gg_id: 13703 *Moorella thermoacetica* str. ET-5a |
| grazer feces | 33223 | Bacteria; *Moorella*; Unclassified; Unclassified; Unclassified; Unclassified; sfA; 33223; L09168.1 gg_id: 13704 *Moorella thermoautotrophica* |
| grazer feces | 52221 | Bacteria; Planctomycetes; Unclassified; Unclassified; Unclassified; Unclassified; shA; 52221; EF999374.1 gg_id: 246960 Vertical and Methanotrophs Estuarine Sediments Pearl River Estuary sediments 22 cm depth clone MidBa21 |
| grazer feces | 34781 | Bacteria; Spirochaetes; Treponemaceae_SP; Treponemaceae_CL; Treponemaceae_OR; Treponemaceae; sfD; 34781; AF068417.1 gg_id: 3976 termite gut homogenate clone RFS59 |
| grazer feces | 52466 | Bacteria; Verrucomicrobia; Opitutae_SP; Unclassified; Unclassified; Unclassified; sfM; 52466; AF523903.1 gg_id: 63314 coal effluent wetland clone RCP2-6 |

TABLE 3

Sewage ID taxa
HUMAN WASTE IDENTIFIER TAXA

| Source | #OTU ID | Lineage for representative OTU |
|---|---|---|
| human waste | 43941 | Bacteria; Bacteroidetes; Bacteroidales_SP; Bacteroidales_CL; Bacteroidales; Bacteroidaceae; sfA; 43941; DQ807427.1 gg_id: 187841 human fecal clone RL307__aam06e04 |
| human waste | 43956 | Bacteria; Bacteroidetes; Bacteroidales_SP; Bacteroidales_CL; Bacteroidales; Bacteroidaceae; sfA; 43956; DQ805892.1 gg_id: 182886 human fecal clone RL306aal92d02 |
| human waste | 44083 | Bacteria; Bacteroidetes; Bacteroidales_SP; Bacteroidales_CL; Bacteroidales; Bacteroidaceae; sfA; 44083; AY981603.1 gg_id: 116720 human sigmoid colon mucosal biopsy clone L795 |
| human waste | 44127 | Bacteria; Bacteroidetes; Bacteroidales_SP; Bacteroidales_CL; Bacteroidales; Bacteroidaceae; sfA; 44127; EF400364.1 gg_id: 206345 human fecal clone SJTU__E__12__20 |
| human waste | 44141 | Bacteria; Bacteroidetes; Bacteroidales_SP; Bacteroidales_CL; Bacteroidales; Bacteroidaceae; sfA; 44141; EF404774.1 gg_id: 209549 human fecal clone SJTU__C__04__23 |
| human waste | 44150 | Bacteria; Bacteroidetes; Bacteroidales_SP; Bacteroidales_CL; Bacteroidales; Bacteroidaceae; sfA; 44150; EU468121.1 gg_id: 292641 Evolution mammals and their gut microbes bush dog feces clone bdog3__aad68e11 |
| human waste | 44161 | Bacteria; Bacteroidetes; Bacteroidales_SP; Bacteroidales_CL; Bacteroidales; Bacteroidaceae; sfA; 44161; DQ801084.1 gg_id: 190166 human fecal clone RL387__aao91h08 |
| human waste | 44219 | Bacteria; Bacteroidetes; Bacteroidales_SP; Bacteroidales_CL; Bacteroidales; Bacteroidaceae; sfA; 44219; AY975836.1 gg_id: 125699 human ascending colon mucosal biopsy clone Y362 |
| human waste | 44261 | Bacteria; Bacteroidetes; Bacteroidales_SP; Bacteroidales_CL; Bacteroidales; Bacteroidaceae; sfA; 44261; EU530387.1 gg_id: 260770 mucosa adherent and invasive microbes adenoma colorectal cancer profile non-adenoma control clone M5-28 |
| human waste | 44307 | Bacteria; Bacteroidetes; Bacteroidales_SP; Bacteroidales_CL; Bacteroidales; Bacteroidaceae; sfA; 44307; EF401089.1 gg_id: 207492 human fecal clone SJTU__D__05__59 |
| human waste | 44345 | Bacteria; Bacteroidetes; Bacteroidales_SP; Bacteroidales_CL; Bacteroidales; Bacteroidaceae; sfA; 44345; AY978434.1 gg_id: 125359 human transverse colon mucosal biopsy clone KO44 |
| human waste | 44403 | Bacteria; Bacteroidetes; Bacteroidales_SP; Bacteroidales_CL; Bacteroidales; Bacteroidaceae; sfA; 44403; X83953.1 gg_id: 2030 *Bacteroides stercoris* str. ATCC 43183T |
| human waste | 44458 | Bacteria; Bacteroidetes; Bacteroidales_SP; Bacteroidales_CL; Bacteroidales; Bacteroidaceae; sfA; 44458; AY982609.1 gg_id: 117026 human descending colon mucosal biopsy clone KW86 |
| human waste | 44509 | Bacteria; Bacteroidetes; Bacteroidales_SP; Bacteroidales_CL; Bacteroidales; Bacteroidaceae; sfA; 44509; DQ799548.1 gg_id: 192828 human fecal clone RL305aal87e09 |
| human waste | 44531 | Bacteria; Bacteroidetes; Bacteroidales_SP; Bacteroidales_CL; Bacteroidales; Bacteroidaceae; sfA; 44531; AJ408988.1 gg_id: 33268 human colonic clone HuCB3 |
| human waste | 44582 | Bacteria; Bacteroidetes; Bacteroidales_SP; Bacteroidales_CL; Bacteroidales; Bacteroidaceae; sfA; 44582; AY981508.1 gg_id: 115442 human sigmoid colon mucosal biopsy clone L628 |
| human waste | 44662 | Bacteria; Bacteroidetes; Bacteroidales_SP; Bacteroidales_CL; Bacteroidales; Bacteroidaceae; sfA; 44662; DQ799526.1 gg_id: 192839 human fecal clone RL305aal87c11 |
| human waste | 44670 | Bacteria; Bacteroidetes; Bacteroidales_SP; Bacteroidales_CL; Bacteroidales; Bacteroidaceae; sfA; 44670; DQ456331.1 gg_id: 158660 pre-adolescent turkey cecum clone CFT212B1 |
| human waste | 44772 | Bacteria; Bacteroidetes; Bacteroidales_SP; Bacteroidales_CL; Bacteroidales; Bacteroidaceae; sfA; 44772; AY982880.1 gg_id: 125638 human descending colon mucosal biopsy clone L050 |
| human waste | 44775 | Bacteria; Bacteroidetes; Bacteroidales_SP; Bacteroidales_CL; Bacteroidales; Bacteroidaceae; sfA; 44775; DQ801359.1 gg_id: 191898 human fecal clone RL388__aao94e01 |
| human waste | 44936 | Bacteria; Bacteroidetes; Bacteroidales_SP; Bacteroidales_CL; Bacteroidales; Bacteroidaceae; sfA; 44936; AY977445.1 gg_id: 118850 human cecum mucosal biopsy clone W154 |
| human waste | 45038 | Bacteria; Bacteroidetes; Bacteroidales_SP; Bacteroidales_CL; Bacteroidales; Bacteroidaceae; sfA; 45038; AB050111.1 gg_id: 22971 *Bacteroides vulgatus* str. JCM 5826T |
| human waste | 45120 | Bacteria; Bacteroidetes; Bacteroidales_SP; Bacteroidales_CL; Bacteroidales; Bacteroidaceae; sfA; 45120; DQ800338.1 gg_id: 185316 human fecal clone RL303__aal71g07 |
| human waste | 45204 | Bacteria; Bacteroidetes; Bacteroidales_SP; Bacteroidales_CL; Bacteroidales; Bacteroidaceae; sfA; 45204; DQ809254.1 gg_id: 184753 human fecal clone RL308__aal84b09 |
| human waste | 45223 | Bacteria; Bacteroidetes; Bacteroidales_SP; Bacteroidales_CL; Bacteroidales; Bacteroidaceae; sfA; 45223; DQ805681.1 gg_id: 193283 human fecal clone RL306aal89g04 |
| human waste | 46741 | Bacteria; Bacteroidetes; Bacteroidales_SP; Bacteroidales_CL; Bacteroidales; Bacteroidaceae; sfA; 46741; DQ795060.1 gg_id: 182958 human fecal clone RL310__aam39f11 |
| human waste | 46763 | Bacteria; Bacteroidetes; Bacteroidales_SP; Bacteroidales_CL; Bacteroidales; Bacteroidaceae; sfA; 46763; EU461748.1 gg_id: 292640 Evolution mammals and their gut microbes mongoose lemur feces clone ML__aaj28b11 |
| human waste | 46764 | Bacteria; Bacteroidetes; Bacteroidales_SP; Bacteroidales_CL; Bacteroidales; Bacteroidaceae; sfA; 46764; EU461664.1 gg_id: 287914 Evolution mammals and their gut microbes mongoose lemur feces clone ML__aaj26f03 |
| human waste | 46771 | Bacteria; Bacteroidetes; Bacteroidales_SP; Bacteroidales_CL; Bacteroidales; Bacteroidaceae; sfA; 46771; EF400686.1 gg_id: 206144 human fecal clone SJTU__E__09__21 |
| human waste | 46778 | Bacteria; Bacteroidetes; Bacteroidales_SP; Bacteroidales_CL; Bacteroidales; Bacteroidaceae; sfA; 46778; AB050850.1 gg_id: 33062 clone CA75 |
| human waste | 46818 | Bacteria; Bacteroidetes; Bacteroidales_SP; Bacteroidales_CL; Bacteroidales; Bacteroidaceae; sfA; 46818; DQ801617.1 gg_id: 184787 human fecal clone RL117__aae92g03 |
| human waste | 46830 | Bacteria; Bacteroidetes; Bacteroidales_SP; Bacteroidales_CL; Bacteroidales; Bacteroidaceae; sfA; 46830; EU469469.1 gg_id: 301928 Evolution mammals and their gut microbes black lemur feces clone BKLE_d09__2 |
| human waste | 46852 | Bacteria; Bacteroidetes; Bacteroidales_SP; Bacteroidales_CL; Bacteroidales; Bacteroidaceae; sfA; 46852; EU459868.1 gg_id: 294155 Evolution mammals and their gut microbes Prevost's squirrel feces clone SQ__aah80d07 |
| human waste | 46873 | Bacteria; Bacteroidetes; Bacteroidales_SP; Bacteroidales_CL; Bacteroidales; Bacteroidaceae; sfA; 46873; EU462268.1 gg_id: 292041 Evolution mammals and their gut microbes chimpanzee feces clone CHIMP1__aaj38g08 |
| human waste | 46894 | Bacteria; Bacteroidetes; Bacteroidales_SP; Bacteroidales_CL; Bacteroidales; Bacteroidaceae; sfA; 46894; AY975979.1 gg_id: 123691 human ascending colon mucosal biopsy clone LT04 |
| human waste | 46902 | Bacteria; Bacteroidetes; Bacteroidales_SP; Bacteroidales_CL; Bacteroidales; Bacteroidaceae; sfA; 46902; DQ800150.1 gg_id: 186315 human fecal clone RL247__aaj24h01 |
| human waste | 46906 | Bacteria; Bacteroidetes; Bacteroidales_SP; Bacteroidales_CL; Bacteroidales; Bacteroidaceae; sfA; 46906; EF400018.1 gg_id: 203578 human fecal clone SJTU__E__07__74 |

TABLE 3-continued

Sewage ID taxa
HUMAN WASTE IDENTIFIER TAXA

| Source | #OTU ID | Lineage for representative OTU |
|---|---|---|
| human waste | 46910 | Bacteria; Bacteroidetes; Bacteroidales_SP; Bacteroidales_CL; Bacteroidales; Bacteroidaceae; sfA; 46910; DQ113691.1 gg_id: 132214 dog colon clone C5-79 |
| human waste | 46938 | Bacteria; Bacteroidetes; Bacteroidales_SP; Bacteroidales_CL; Bacteroidales; Bacteroidaceae; sfA; 46938; DQ113737.1 gg_id: 132480 dog colon clone C5-17 |
| human waste | 46966 | Bacteria; Bacteroidetes; Bacteroidales_SP; Bacteroidales_CL; Bacteroidales; Bacteroidaceae; sfA; 46966; AY979558.1 gg_id: 127006 human transverse colon mucosal biopsy clone M219 |
| human waste | 46968 | Bacteria; Bacteroidetes; Bacteroidales_SP; Bacteroidales_CL; Bacteroidales; Bacteroidaceae; sfA; 46968; EU467121.1 gg_id: 293143 Evolution mammals and their gut microbes mongoose lemur feces clone ML_aae88g03 |
| human waste | 46975 | Bacteria; Bacteroidetes; Bacteroidales_SP; Bacteroidales_CL; Bacteroidales; Bacteroidaceae; sfA; 46975; DQ801565.1 gg_id: 194357 human fecal clone RL117_aae91e01 |
| human waste | 47002 | Bacteria; Bacteroidetes; Bacteroidales_SP; Bacteroidales_CL; Bacteroidales; Bacteroidaceae; sfA; 47002; AY982519.1 gg_id: 122780 human sigmoid colon mucosal biopsy clone MN42 |
| human waste | 47004 | Bacteria; Bacteroidetes; Bacteroidales_SP; Bacteroidales_CL; Bacteroidales; Bacteroidaceae; sfA; 47004; AY976221.1 gg_id: 117505 human ascending colon mucosal biopsy clone LW48 |
| human waste | 47007 | Bacteria; Bacteroidetes; Bacteroidales_SP; Bacteroidales_CL; Bacteroidales; Bacteroidaceae; sfA; 47007; AY983887.1 gg_id: 123211 human descending colon mucosal biopsy clone MA60 |
| human waste | 47011 | Bacteria; Bacteroidetes; Bacteroidales_SP; Bacteroidales_CL; Bacteroidales; Bacteroidaceae; sfA; 47011; AY979509.1 gg_id: 115799 human transverse colon mucosal biopsy clone M155 |
| human waste | 47063 | Bacteria; Bacteroidetes; Bacteroidales_SP; Bacteroidales_CL; Bacteroidales; Bacteroidaceae; sfA; 47063; EU462001.1 gg_id: 298154 Evolution mammals and their gut microbes black-handed spider monkey feces clone SPIM_aaj33b06 |
| human waste | 47115 | Bacteria; Bacteroidetes; Bacteroidales_SP; Bacteroidales_CL; Bacteroidales; Bacteroidaceae; sfA; 47115; EU461698.1 gg_id: 296522 Evolution mammals and their gut microbes mongoose lemur feces clone ML_aaj27c12 |
| human waste | 47151 | Bacteria; Bacteroidetes; Bacteroidales_SP; Bacteroidales_CL; Bacteroidales; Bacteroidaceae; sfA; 47151; EU461683.1 gg_id: 299285 Evolution mammals and their gut microbes mongoose lemur feces clone ML_aaj27a06 |
| human waste | 47170 | Bacteria; Bacteroidetes; Bacteroidales_SP; Bacteroidales_CL; Bacteroidales; Bacteroidaceae; sfA; 47170; DQ797117.1 gg_id: 189432 human fecal clone RL386_aao87b12 |
| human waste | 47188 | Bacteria; Bacteroidetes; Bacteroidales_SP; Bacteroidales_CL; Bacteroidales; Bacteroidaceae; sfA; 47188; DQ801614.1 gg_id: 195924 human fecal clone RL117_aae92f10 |
| human waste | 47195 | Bacteria; Bacteroidetes; Bacteroidales_SP; Bacteroidales_CL; Bacteroidales; Bacteroidaceae; sfA; 47195; EF400137.1 gg_id: 216740 human fecal clone SJTU_E_09_32 |
| human waste | 47204 | Bacteria; Bacteroidetes; Bacteroidales_SP; Bacteroidales_CL; Bacteroidales; Bacteroidaceae; sfA; 47204; EU458688.1 gg_id: 291144 Evolution mammals and their gut microbes Goeldi's marmoset feces clone CAL_b09 |
| human waste | 47206 | Bacteria; Bacteroidetes; Bacteroidales_SP; Bacteroidales_CL; Bacteroidales; Bacteroidaceae; sfA; 47206; EU459974.1 gg_id: 298264 Evolution mammals and their gut microbes Prevost's squirrel feces clone SQ_aah82b12 |
| human waste | 47243 | Bacteria; Bacteroidetes; Bacteroidales_SP; Bacteroidales_CL; Bacteroidales; Bacteroidaceae; sfA; 47243; AY982378.1 gg_id: 117849 human sigmoid colon mucosal biopsy clone MK20 |
| human waste | 47250 | Bacteria; Bacteroidetes; Bacteroidales_SP; Bacteroidales_CL; Bacteroidales; Bacteroidaceae; sfA; 47250; AY982457.1 gg_id: 119224 human sigmoid colon mucosal biopsy clone ML91 |
| human waste | 47263 | Bacteria; Bacteroidetes; Bacteroidales_SP; Bacteroidales_CL; Bacteroidales; Bacteroidaceae; sfA; 47263; EU467222.1 gg_id: 294806 Evolution mammals and their gut microbes black-handed spider monkey feces clone SPIM_e11 |
| human waste | 47265 | Bacteria; Bacteroidetes; Bacteroidales_SP; Bacteroidales_CL; Bacteroidales; Bacteroidaceae; sfA; 47265; EU461737.1 gg_id: 295554 Evolution mammals and their gut microbes mongoose lemur feces clone ML_aaj28a07 |
| human waste | 47316 | Bacteria; Bacteroidetes; Bacteroidales_SP; Bacteroidales_CL; Bacteroidales; Bacteroidaceae; sfA; 47316; EU459867.1 gg_id: 298617 Evolution mammals and their gut microbes Prevost's squirrel feces clone SQ_aah80d05 |
| human waste | 47360 | Bacteria; Bacteroidetes; Bacteroidales_SP; Bacteroidales_CL; Bacteroidales; Bacteroidaceae; sfA; 47360; EU458706.1 gg_id: 296262 Evolution mammals and their gut microbes Goeldi's marmoset feces clone CAL_f10 |
| human waste | 47388 | Bacteria; Bacteroidetes; Bacteroidales_SP; Bacteroidales_CL; Bacteroidales; Bacteroidaceae; sfA; 47388; DQ794918.1 gg_id: 191249 human fecal clone RL310_aam37h08 |
| human waste | 47396 | Bacteria; Bacteroidetes; Bacteroidales_SP; Bacteroidales_CL; Bacteroidales; Bacteroidaceae; sfA; 47396; EF400258.1 gg_id: 211793 human fecal clone SJTU_E_10_88 |
| human waste | 47411 | Bacteria; Bacteroidetes; Bacteroidales_SP; Bacteroidales_CL; Bacteroidales; Bacteroidaceae; sfA; 47411; EF400377.1 gg_id: 203899 human fecal clone SJTU_E_12_47 |
| human waste | 47431 | Bacteria; Bacteroidetes; Bacteroidales_SP; Bacteroidales_CL; Bacteroidales; Bacteroidaceae; sfA; 47431; EU461718.1 gg_id: 298857 Evolution mammals and their gut microbes mongoose lemur feces clone ML_aaj27f07 |
| human waste | 47432 | Bacteria; Bacteroidetes; Bacteroidales_SP; Bacteroidales_CL; Bacteroidales; Bacteroidaceae; sfA; 47432; EU461728.1 gg_id: 289983 Evolution mammals and their gut microbes mongoose lemur feces clone ML_aaj27g09 |
| human waste | 47433 | Bacteria; Bacteroidetes; Bacteroidales_SP; Bacteroidales_CL; Bacteroidales; Bacteroidaceae; sfA; 47433; EU462279.1 gg_id: 294270 Evolution mammals and their gut microbes chimpanzee feces clone CHIMP1_aaj39b01 |
| human waste | 47466 | Bacteria; Bacteroidetes; Bacteroidales_SP; Bacteroidales_CL; Bacteroidales; Bacteroidaceae; sfA; 47466; DQ797184.1 gg_id: 174975 human fecal clone RL386_aao88b01 |
| human waste | 47501 | Bacteria; Bacteroidetes; Bacteroidales_SP; Bacteroidales_CL; Bacteroidales; Bacteroidaceae; sfA; 47501; EU469531.1 gg_id: 293939 Evolution mammals and their gut microbes black lemur feces clone BKLE_f08_2 |
| human waste | 47504 | Bacteria; Bacteroidetes; Bacteroidales_SP; Bacteroidales_CL; Bacteroidales; Bacteroidaceae; sfA; 47504; DQ809204.1 gg_id: 192651 human fecal clone RL308_aal83d05 |
| human waste | 47529 | Bacteria; Bacteroidetes; Bacteroidales_SP; Bacteroidales_CL; Bacteroidales; Bacteroidaceae; sfA; 47529; AY979613.1 gg_id: 123169 human transverse colon mucosal biopsy clone M306 |
| human waste | 47545 | Bacteria; Bacteroidetes; Bacteroidales_SP; Bacteroidales_CL; Bacteroidales; Bacteroidaceae; sfA; 47545; AY980828.1 gg_id: 124789 human rectum mucosal biopsy clone LO82 |
| human waste | 47554 | Bacteria; Bacteroidetes; Bacteroidales_SP; Bacteroidales_CL; Bacteroidales; Bacteroidaceae; sfA; 47554; DQ796298.1 gg_id: 186364 human fecal clone RL179_aah25d08 |
| human waste | 47562 | Bacteria; Bacteroidetes; Bacteroidales_SP; Bacteroidales_CL; Bacteroidales; Bacteroidaceae; sfA; 47562; EU462275.1 gg_id: 291569 Evolution mammals and their gut microbes chimpanzee feces clone CHIMP1_aaj38h09 |
| human waste | 47601 | Bacteria; Bacteroidetes; Bacteroidales_SP; Bacteroidales_CL; Bacteroidales; Bacteroidaceae; sfA; 47601; AY982484.1 gg_id: 116450 human sigmoid colon mucosal biopsy clone MM55 |

TABLE 3-continued

Sewage ID taxa
HUMAN WASTE IDENTIFIER TAXA

| Source | #OTU ID | Lineage for representative OTU |
|---|---|---|
| human waste | 47640 | Bacteria; Bacteroidetes; Bacteroidales_SP; Bacteroidales_CL; Bacteroidales; Bacteroidaceae; sfA; 47640; DQ801569.1 gg_id: 192124 human fecal clone RL117_aae91f01 |
| human waste | 47669 | Bacteria; Bacteroidetes; Bacteroidales_SP; Bacteroidales_CL; Bacteroidales; Bacteroidaceae; sfA; 47669; AY983808.1 gg_id: 127263 human descending colon mucosal biopsy clone M868 |
| human waste | 47677 | Bacteria; Bacteroidetes; Bacteroidales_SP; Bacteroidales_CL; Bacteroidales; Bacteroidaceae; sfA; 47677; AY976024.1 gg_id: 117319 human ascending colon mucosal biopsy clone LT70 |
| human waste | 47696 | Bacteria; Bacteroidetes; Bacteroidales_SP; Bacteroidales_CL; Bacteroidales; Bacteroidaceae; sfA; 47696; EF399655.1 gg_id: 214048 human fecal clone SJTU_E_01_71 |
| human waste | 47703 | Bacteria; Bacteroidetes; Bacteroidales_SP; Bacteroidales_CL; Bacteroidales; Bacteroidaceae; sfA; 47703; EF400411.1 gg_id: 203890 human fecal clone SJTU_E_13_08 |
| human waste | 47704 | Bacteria; Bacteroidetes; Bacteroidales_SP; Bacteroidales_CL; Bacteroidales; Bacteroidaceae; sfA; 47704; EU461635.1 gg_id: 300732 Evolution mammals and their gut microbes mongoose lemur feces clone ML_aaj26a02 |
| human waste | 47741 | Bacteria; Bacteroidetes; Bacteroidales_SP; Bacteroidales_CL; Bacteroidales; Bacteroidaceae; sfA; 47741; AY911436.1 gg_id: 123215 rock interior clone NEC02083 |
| human waste | 47749 | Bacteria; Bacteroidetes; Bacteroidales_SP; Bacteroidales_CL; Bacteroidales; Bacteroidaceae; sfA; 47749; EU459820.1 gg_id: 290871 Evolution mammals and their gut microbes Prevost's squirrel feces clone SQ_aah79d12 |
| human waste | 47807 | Bacteria; Bacteroidetes; Bacteroidales_SP; Bacteroidales_CL; Bacteroidales; Bacteroidaceae; sfA; 47807; DQ797088.1 gg_id: 177751 human fecal clone RL386_aao86h01 |
| human waste | 47808 | Bacteria; Bacteroidetes; Bacteroidales_SP; Bacteroidales_CL; Bacteroidales; Bacteroidaceae; sfA; 47808; AY976026.1 gg_id: 127059 human ascending colon mucosal biopsy clone LT72 |
| human waste | 47809 | Bacteria; Bacteroidetes; Bacteroidales_SP; Bacteroidales_CL; Bacteroidales; Bacteroidaceae; sfA; 47809; EF400393.1 gg_id: 213428 human fecal clone SJTU_E_12_74 |
| human waste | 47811 | Bacteria; Bacteroidetes; Bacteroidales_SP; Bacteroidales_CL; Bacteroidales; Bacteroidaceae; sfA; 47811; AY980957.1 gg_id: 117270 human rectum mucosal biopsy clone V028 |
| human waste | 47836 | Bacteria; Bacteroidetes; Bacteroidales_SP; Bacteroidales_CL; Bacteroidales; Bacteroidaceae; sfA; 47836; EU462159.1 gg_id: 301898 Evolution mammals and their gut microbes black-handed spider monkey feces clone SPIM_aaj36b06 |
| human waste | 47867 | Bacteria; Bacteroidetes; Bacteroidales_SP; Bacteroidales_CL; Bacteroidales; Bacteroidaceae; sfA; 47867; AY980928.1 gg_id: 117167 human rectum mucosal biopsy clone LR44 |
| human waste | 47901 | Bacteria; Bacteroidetes; Bacteroidales_SP; Bacteroidales_CL; Bacteroidales; Bacteroidaceae; sfA; 47901; AY976458.1 gg_id: 124114 human ascending colon mucosal biopsy clone LZ62 |
| human waste | 47942 | Bacteria; Bacteroidetes; Bacteroidales_SP; Bacteroidales_CL; Bacteroidales; Bacteroidaceae; sfA; 47942; DQ801367.1 gg_id: 181561 human fecal clone RL388_aao94e10 |
| human waste | 47959 | Bacteria; Bacteroidetes; Bacteroidales_SP; Bacteroidales_CL; Bacteroidales; Bacteroidaceae; sfA; 47959; AY980875.1 gg_id: 116049 human rectum mucosal biopsy clone LQ01 |
| human waste | 47967 | Bacteria; Bacteroidetes; Bacteroidales_SP; Bacteroidales_CL; Bacteroidales; Bacteroidaceae; sfA; 47967; EF400084.1 gg_id: 216981 human fecal clone SJTU_E_08_66 |
| human waste | 47970 | Bacteria; Bacteroidetes; Bacteroidales_SP; Bacteroidales_CL; Bacteroidales; Bacteroidaceae; sfA; 47970; EF400522.1 gg_id: 211644 human fecal clone SJTU_E_14_44 |
| human waste | 47997 | Bacteria; Bacteroidetes; Bacteroidales_SP; Bacteroidales_CL; Bacteroidales; Bacteroidaceae; sfA; 47997; AY976328.1 gg_id: 115520 human ascending colon mucosal biopsy clone LX89 |
| human waste | 48008 | Bacteria; Bacteroidetes; Bacteroidales_SP; Bacteroidales_CL; Bacteroidales; Bacteroidaceae; sfA; 48008; EF405193.1 gg_id: 214671 human fecal clone SJTU_G_04_12 |
| human waste | 48029 | Bacteria; Bacteroidetes; Bacteroidales_SP; Bacteroidales_CL; Bacteroidales; Bacteroidaceae; sfA; 48029; DQ794923.1 gg_id: 186767 human fecal clone RL310_aam38a02 |
| human waste | 48048 | Bacteria; Bacteroidetes; Bacteroidales_SP; Bacteroidales_CL; Bacteroidales; Bacteroidaceae; sfA; 48048; AY982452.1 gg_id: 117045 human sigmoid colon mucosal biopsy clone ML81 |
| human waste | 48049 | Bacteria; Bacteroidetes; Bacteroidales_SP; Bacteroidales_CL; Bacteroidales; Bacteroidaceae; sfA; 48049; EU461763.1 gg_id: 299750 Evolution mammals and their gut microbes mongoose lemur feces clone ML_aaj28e03 |
| human waste | 48074 | Bacteria; Bacteroidetes; Bacteroidales_SP; Bacteroidales_CL; Bacteroidales; Bacteroidaceae; sfA; 48074; EU461764.1 gg_id: 297071 Evolution mammals and their gut microbes mongoose lemur feces clone ML_aaj28e05 |
| human waste | 48079 | Bacteria; Bacteroidetes; Bacteroidales_SP; Bacteroidales_CL; Bacteroidales; Bacteroidaceae; sfA; 48079; AY979815.1 gg_id: 118647 human transverse colon mucosal biopsy clone M626 |
| human waste | 48092 | Bacteria; Bacteroidetes; Bacteroidales_SP; Bacteroidales_CL; Bacteroidales; Bacteroidaceae; sfA; 48092; AY979791.1 gg_id: 126167 human transverse colon mucosal biopsy clone M562 |
| human waste | 48102 | Bacteria; Bacteroidetes; Bacteroidales_SP; Bacteroidales_CL; Bacteroidales; Bacteroidaceae; sfA; 48102; AF153867.1 gg_id: 2189 faecal clone adhufec61.25 |
| human waste | 48118 | Bacteria; Bacteroidetes; Bacteroidales_SP; Bacteroidales_CL; Bacteroidales; Bacteroidaceae; sfA; 48118; AY985235.1 gg_id: 117409 human stool clone C110 |
| human waste | 48134 | Bacteria; Bacteroidetes; Bacteroidales_SP; Bacteroidales_CL; Bacteroidales; Bacteroidaceae; sfA; 48134; DQ801573.1 gg_id: 196055 human fecal clone RL117_aae91f07 |
| human waste | 48147 | Bacteria; Bacteroidetes; Bacteroidales_SP; Bacteroidales_CL; Bacteroidales; Bacteroidaceae; sfA; 48147; AY982290.1 gg_id: 127110 human sigmoid colon mucosal biopsy clone MI40 |
| human waste | 48156 | Bacteria; Bacteroidetes; Bacteroidales_SP; Bacteroidales_CL; Bacteroidales; Bacteroidaceae; sfA; 48156; AY982201.1 gg_id: 127390 human sigmoid colon mucosal biopsy clone MG93 |
| human waste | 48158 | Bacteria; Bacteroidetes; Bacteroidales_SP; Bacteroidales_CL; Bacteroidales; Bacteroidaceae; sfA; 48158; AY983791.1 gg_id: 115506 human descending colon mucosal biopsy clone M835 |
| human waste | 48180 | Bacteria; Bacteroidetes; Bacteroidales_SP; Bacteroidales_CL; Bacteroidales; Bacteroidaceae; sfA; 48180; EU469364.1 gg_id: 293011 Evolution mammals and their gut microbes black lemur feces clone BKLE_b11 |
| human waste | 48448 | Bacteria; Bacteroidetes; Bacteroidales_SP; Bacteroidales_CL; Bacteroidales; Bacteroidaceae; sfA; 48448; DQ795058.1 gg_id: 189521 human fecal clone RL310_aam39f09 |
| human waste | 45616 | Bacteria; Bacteroidetes; Bacteroidales_SP; Bacteroidales_CL; Bacteroidales; Parabacteroidaceae; sfA; 45616; EU763425.1 gg_id: 304177 Pervasive effects antibiotic on human gut microbiota deep sequencing fecal clone A4_636 |
| human waste | 47209 | Bacteria; Bacteroidetes; Bacteroidales_SP; Bacteroidales_CL; Bacteroidales; Parabacteroidaceae; sfA; 47209; AF357554.1 gg_id: 69900 mpn-isolate group 6 |

TABLE 3-continued

Sewage ID taxa
HUMAN WASTE IDENTIFIER TAXA

| Source | #OTU ID | Lineage for representative OTU |
|---|---|---|
| human waste | 47321 | Bacteria; Bacteroidetes; Bacteroidales_SP; Bacteroidales_CL; Bacteroidales; Parabacteroidaceae; sfA; 47321; EU472248.1 gg_id: 290566 Evolution mammals and their gut microbes francois langur feces clone FL_2aaa04b09 |
| human waste | 58596 | Bacteria; Bacteroidetes; Bacteroidales_SP; Bacteroidales_CL; Bacteroidales; Rikenellaceae; sfF; 58596; DQ805939.1 gg_id: 175142 human fecal clone RL306aal92h06 |
| human waste | 46820 | Bacteria; Bacteroidetes; Bacteroidales_SP; Bacteroidales_CL; Bacteroidales; Unclassified; sfB; 46820; EU037967.1 gg_id: 242141 Bioenergy production: microbial conversion residual oil natural enriched gas condensate-contaminated aquifer clone E452-2 |
| human waste | 11819 | Bacteria; Bacteroidetes; Flavobacteriales_SP; Flavobacteriales_CL; Flavobacteriales; *Sporocytophaga*_FM; sfA; 11819; U85888.1 gg_id: 2295 *Flavobacterium* sp. str. A265 |
| human waste | 13221 | Bacteria; Firmicutes; Acidaminococcaceae_SP; Acidaminococcaceae_CL; Acidaminococcaceae_OR; Acidaminococcaceae; sfB; 13221; DQ794346.1 gg_id: 187487 human fecal clone RL197_aah86a07 |
| human waste | 13581 | Bacteria; Firmicutes; Acidaminococcaceae_SP; Acidaminococcaceae_CL; Acidaminococcaceae_OR; Acidaminococcaceae; sfB; 13581; AJ812140.1 gg_id: 107617 mucosal biopsies human intestine clone 178k07 |
| human waste | 1018 | Bacteria; Firmicutes; Clostridia_SP; Clostridiales_CL; Clostridiales; *Clostridium*_FM; sfA; 1018; DQ905539.1 gg_id: 165398 human fecal clone 014B-A6 |
| human waste | 176 | Bacteria; Firmicutes; Clostridia_SP; Clostridiales_CL; Clostridiales; *Clostridium*_FM; sfA; 176; EF404693.1 gg_id: 206652 human fecal clone SJTU_C_14_62 |
| human waste | 1952 | Bacteria; Firmicutes; Clostridia_SP; Clostridiales_CL; Clostridiales; *Clostridium*_FM; sfA; 1952; AY592220.1 gg_id: 101163 marine ANAMMOX sediment clone AY592220 |
| human waste | 2716 | Bacteria; Firmicutes; Clostridia_SP; Clostridiales_CL; Clostridiales; *Clostridium*_FM; sfA; 2716; DQ801212.1 gg_id: 196846 human fecal clone RL116_aaf01c08 |
| human waste | 4629 | Bacteria; Firmicutes; Clostridia_SP; Clostridiales_CL; Clostridiales; *Clostridium*_FM; sfA; 4629; DQ807120.1 gg_id: 177058 human fecal clone RL244_aaj46e07 |
| human waste | 5005 | Bacteria; Firmicutes; Clostridia_SP; Clostridiales_CL; Clostridiales; *Clostridium*_FM; sfA; 5005; DQ803717.1 gg_id: 195413 human fecal clone RL200_aai57e06 |
| human waste | 5169 | Bacteria; Firmicutes; Clostridia_SP; Clostridiales_CL; Clostridiales; *Clostridium*_FM; sfA; 5169; DQ798027.1 gg_id: 178352 human fecal clone RL302_aal94f11 |
| human waste | 5691 | Bacteria; Firmicutes; Clostridia_SP; Clostridiales_CL; Clostridiales; *Clostridium*_FM; sfA; 5691; DQ804862.1 gg_id: 198522 human fecal clone RL385_aao81g01 |
| human waste | 5753 | Bacteria; Firmicutes; Clostridia_SP; Clostridiales_CL; Clostridiales; *Clostridium*_FM; sfA; 5753; DQ809514.1 gg_id: 184892 human fecal clone RL184_aah22b02 |
| human waste | 73 | Bacteria; Firmicutes; Clostridia_SP; Clostridiales_CL; Clostridiales; *Clostridium*_FM; sfA; 73; DQ809379.1 gg_id: 189530 human fecal clone RL184_aah20a09 |
| human waste | 1000 | Bacteria; Firmicutes; Clostridia_SP; Clostridiales_CL; Clostridiales; *Eubacterium*_FM; sfA; 1000; DQ802749.1 gg_id: 175199 human fecal clone RL188_aan96b02 |
| human waste | 101 | Bacteria; Firmicutes; Clostridia_SP; Clostridiales_CL; Clostridiales; *Eubacterium*_FM; sfA; 101; DQ794320.1 gg_id: 192508 human fecal clone RL197_aah85c09 |
| human waste | 1052 | Bacteria; Firmicutes; Clostridia_SP; Clostridiales_CL; Clostridiales; *Eubacterium*_FM; sfA; 1052; DQ797276.1 gg_id: 183705 human fecal clone RL248_aai97c02 |
| human waste | 1114 | Bacteria; Firmicutes; Clostridia_SP; Clostridiales_CL; Clostridiales; *Eubacterium*_FM; sfA; 1114; AY980662.1 gg_id: 126910 human rectum mucosal biopsy clone LL61 |
| human waste | 1154 | Bacteria; Firmicutes; Clostridia_SP; Clostridiales_CL; Clostridiales; *Eubacterium*_FM; sfA; 1154; DQ804746.1 gg_id: 174585 human fecal clone RL187_aao72b10 |
| human waste | 1257 | Bacteria; Firmicutes; Clostridia_SP; Clostridiales_CL; Clostridiales; *Eubacterium*_FM; sfA; 1257; DQ802595.1 gg_id: 183904 human fecal clone RL188_aan93h03 |
| human waste | 1272 | Bacteria; Firmicutes; Clostridia_SP; Clostridiales_CL; Clostridiales; *Eubacterium*_FM; sfA; 1272; DQ802735.1 gg_id: 189978 human fecal clone RL188_aan95h06 |
| human waste | 129 | Bacteria; Firmicutes; Clostridia_SP; Clostridiales_CL; Clostridiales; *Eubacterium*_FM; sfA; 129; DQ905684.1 gg_id: 166745 human fecal clone 014C-F11 |
| human waste | 1374 | Bacteria; Firmicutes; Clostridia_SP; Clostridiales_CL; Clostridiales; *Eubacterium*_FM; sfA; 1374; DQ804653.1 gg_id: 175366 human fecal clone RL187_aao70h10 |
| human waste | 1399 | Bacteria; Firmicutes; Clostridia_SP; Clostridiales_CL; Clostridiales; *Eubacterium*_FM; sfA; 1399; AY984583.1 gg_id: 115391 human stool clone B523 |
| human waste | 1457 | Bacteria; Firmicutes; Clostridia_SP; Clostridiales_CL; Clostridiales; *Eubacterium*_FM; sfA; 1457; DQ825185.1 gg_id: 177033 human fecal clone RL185_aan86d08 |
| human waste | 1476 | Bacteria; Firmicutes; Clostridia_SP; Clostridiales_CL; Clostridiales; *Eubacterium*_FM; sfA; 1476; DQ806013.1 gg_id: 177763 human fecal clone RL186_aah59h10 |
| human waste | 1495 | Bacteria; Firmicutes; Clostridia_SP; Clostridiales_CL; Clostridiales; *Eubacterium*_FM; sfA; 1495; AY980949.1 gg_id: 117339 human rectum mucosal biopsy clone V010 |
| human waste | 1554 | Bacteria; Firmicutes; Clostridia_SP; Clostridiales_CL; Clostridiales; *Eubacterium*_FM; sfA; 1554; DQ806099.1 gg_id: 199240 human fecal clone RL186_aah61b06 |
| human waste | 1603 | Bacteria; Firmicutes; Clostridia_SP; Clostridiales_CL; Clostridiales; *Eubacterium*_FM; sfA; 1603; DQ805711.1 gg_id: 183206 human fecal clone RL306aal90b06 |
| human waste | 165 | Bacteria; Firmicutes; Clostridia_SP; Clostridiales_CL; Clostridiales; *Eubacterium*_FM; sfA; 165; DQ794874.1 gg_id: 176738 human fecal clone RL310_aam37d05 |
| human waste | 1650 | Bacteria; Firmicutes; Clostridia_SP; Clostridiales_CL; Clostridiales; *Eubacterium*_FM; sfA; 1650; DQ802144.1 gg_id: 193870 human fecal clone RL241_aaj03f05 |
| human waste | 167 | Bacteria; Firmicutes; Clostridia_SP; Clostridiales_CL; Clostridiales; *Eubacterium*_FM; sfA; 167; EF403709.1 gg_id: 209846 human fecal clone SJTU_A2_05_66 |
| human waste | 1717 | Bacteria; Firmicutes; Clostridia_SP; Clostridiales_CL; Clostridiales; *Eubacterium*_FM; sfA; 1717; DQ807663.1 gg_id: 174489 human fecal clone RL180_aah35f06 |
| human waste | 1723 | Bacteria; Firmicutes; Clostridia_SP; Clostridiales_CL; Clostridiales; *Eubacterium*_FM; sfA; 1723; DQ798354.1 gg_id: 194115 human fecal clone RL181_aah41d07 |

TABLE 3-continued

Sewage ID taxa
HUMAN WASTE IDENTIFIER TAXA

| Source | #OTU ID | Lineage for representative OTU |
|---|---|---|
| human waste | 1737 | Bacteria; Firmicutes; Clostridia_SP; Clostridiales_CL; Clostridiales; *Eubacterium*_FM; sfA; 1737; DQ809960.1 gg_id: 199364 human fecal clone RL184__aao66d07 |
| human waste | 1744 | Bacteria; Firmicutes; Clostridia_SP; Clostridiales_CL; Clostridiales; *Eubacterium*_FM; sfA; 1744; DQ327083.1 gg_id: 147063 Metagenomic gut microbiome healthy human stool clone E593 |
| human waste | 1798 | Bacteria; Firmicutes; Clostridia_SP; Clostridiales_CL; Clostridiales; *Eubacterium*_FM; sfA; 1798; DQ825318.1 gg_id: 197347 human fecal clone RL185__aan88d08 |
| human waste | 1832 | Bacteria; Firmicutes; Clostridia_SP; Clostridiales_CL; Clostridiales; *Eubacterium*_FM; sfA; 1832; AY982954.1 gg_id: 119825 human descending colon mucosal biopsy clone L158 |
| human waste | 1849 | Bacteria; Firmicutes; Clostridia_SP; Clostridiales_CL; Clostridiales; *Eubacterium*_FM; sfA; 1849; DQ327472.1 gg_id: 149222 Metagenomic gut microbiome healthy human stool clone EA40 |
| human waste | 1878 | Bacteria; Firmicutes; Clostridia_SP; Clostridiales_CL; Clostridiales; *Eubacterium*_FM; sfA; 1878; DQ327557.1 gg_id: 146527 Metagenomic gut microbiome healthy human stool clone EB40 |
| human waste | 1897 | Bacteria; Firmicutes; Clostridia_SP; Clostridiales_CL; Clostridiales; *Eubacterium*_FM; sfA; 1897; AY976744.1 gg_id: 123541 human cecum mucosal biopsy clone K341 |
| human waste | 1903 | Bacteria; Firmicutes; Clostridia_SP; Clostridiales_CL; Clostridiales; *Eubacterium*_FM; sfA; 1903; DQ806212.1 gg_id: 199111 human fecal clone RL186__aah62g01 |
| human waste | 1917 | Bacteria; Firmicutes; Clostridia_SP; Clostridiales_CL; Clostridiales; *Eubacterium*_FM; sfA; 1917; EU467004.1 gg_id: 298685 Evolution mammals and their gut microbes African elephant feces clone AFEL2__aao32e11 |
| human waste | 1943 | Bacteria; Firmicutes; Clostridia_SP; Clostridiales_CL; Clostridiales; *Eubacterium*_FM; sfA; 1943; DQ326898.1 gg_id: 149314 Metagenomic gut microbiome healthy human stool clone E382 |
| human waste | 1977 | Bacteria; Firmicutes; Clostridia_SP; Clostridiales_CL; Clostridiales; *Eubacterium*_FM; sfA; 1977; DQ798092.1 gg_id: 195202 human fecal clone RL302__aal95d08 |
| human waste | 1992 | Bacteria; Firmicutes; Clostridia_SP; Clostridiales_CL; Clostridiales; *Eubacterium*_FM; sfA; 1992; DQ905520.1 gg_id: 173210 human fecal clone 014-f31 |
| human waste | 200 | Bacteria; Firmicutes; Clostridia_SP; Clostridiales_CL; Clostridiales; *Eubacterium*_FM; sfA; 200; DQ806114.1 gg_id: 193697 human fecal clone RL186__aah61d03 |
| human waste | 2022 | Bacteria; Firmicutes; Clostridia_SP; Clostridiales_CL; Clostridiales; *Eubacterium*_FM; sfA; 2022; DQ806726.1 gg_id: 195865 human fecal clone RL186__aao48a05 |
| human waste | 243 | Bacteria; Firmicutes; Clostridia_SP; Clostridiales_CL; Clostridiales; *Eubacterium*_FM; sfA; 243; AY983091.1 gg_id: 116526 human descending colon mucosal biopsy clone L338 |
| human waste | 329 | Bacteria; Firmicutes; Clostridia_SP; Clostridiales_CL; Clostridiales; *Eubacterium*_FM; sfA; 329; DQ825186.1 gg_id: 184383 human fecal clone RL185__aan86d09 |
| human waste | 335 | Bacteria; Firmicutes; Clostridia_SP; Clostridiales_CL; Clostridiales; *Eubacterium*_FM; sfA; 335; DQ805700.1 gg_id: 185184 human fecal clone RL306aal90a02 |
| human waste | 343 | Bacteria; Firmicutes; Clostridia_SP; Clostridiales_CL; Clostridiales; *Eubacterium*_FM; sfA; 343; DQ327130.1 gg_id: 145348 Metagenomic gut microbiome healthy human stool clone E648 |
| human waste | 365 | Bacteria; Firmicutes; Clostridia_SP; Clostridiales_CL; Clostridiales; *Eubacterium*_FM; sfA; 365; DQ802579.1 gg_id: 197394 human fecal clone RL188__aan93f05 |
| human waste | 40020 | Bacteria; Firmicutes; Clostridia_SP; Clostridiales_CL; Clostridiales; *Eubacterium*_FM; sfA; 40020; DQ809879.1 gg_id: 175650 human fecal clone RL184__aao65d11 |
| human waste | 413 | Bacteria; Firmicutes; Clostridia_SP; Clostridiales_CL; Clostridiales; *Eubacterium*_FM; sfA; 413; DQ824795.1 gg_id: 184074 human fecal clone RL185__aao69d04 |
| human waste | 449 | Bacteria; Firmicutes; Clostridia_SP; Clostridiales_CL; Clostridiales; *Eubacterium*_FM; sfA; 449; DQ802220.1 gg_id: 185239 human fecal clone RL241__aaj04f07 |
| human waste | 491 | Bacteria; Firmicutes; Clostridia_SP; Clostridiales_CL; Clostridiales; *Eubacterium*_FM; sfA; 491; EU466862.1 gg_id: 296859 Evolution mammals and their gut microbes African elephant feces clone AFEL2__aao30e03 |
| human waste | 498 | Bacteria; Firmicutes; Clostridia_SP; Clostridiales_CL; Clostridiales; *Eubacterium*_FM; sfA; 498; DQ802686.1 gg_id: 179680 human fecal clone RL188__aan95b10 |
| human waste | 505 | Bacteria; Firmicutes; Clostridia_SP; Clostridiales_CL; Clostridiales; *Eubacterium*_FM; sfA; 505; DQ327011.1 gg_id: 149415 Metagenomic gut microbiome healthy human stool clone E512 |
| human waste | 533 | Bacteria; Firmicutes; Clostridia_SP; Clostridiales_CL; Clostridiales; *Eubacterium*_FM; sfA; 533; DQ807644.1 gg_id: 182440 human fecal clone RL180__aah35d06 |
| human waste | 541 | Bacteria; Firmicutes; Clostridia_SP; Clostridiales_CL; Clostridiales; *Eubacterium*_FM; sfA; 541; DQ807714.1 gg_id: 177652 human fecal clone RL180__aah36c12 |
| human waste | 542 | Bacteria; Firmicutes; Clostridia_SP; Clostridiales_CL; Clostridiales; *Eubacterium*_FM; sfA; 542; DQ802314.1 gg_id: 185946 human fecal clone RL188__aah15h11 |
| human waste | 565 | Bacteria; Firmicutes; Clostridia_SP; Clostridiales_CL; Clostridiales; *Eubacterium*_FM; sfA; 565; DQ808215.1 gg_id: 174083 human fecal clone RL180__aao74a03 |
| human waste | 629 | Bacteria; Firmicutes; Clostridia_SP; Clostridiales_CL; Clostridiales; *Eubacterium*_FM; sfA; 629; DQ905692.1 gg_id: 162699 human fecal clone 014C-G9 |
| human waste | 661 | Bacteria; Firmicutes; Clostridia_SP; Clostridiales_CL; Clostridiales; *Eubacterium*_FM; sfA; 661; DQ802105.1 gg_id: 195859 human fecal clone RL241__aaj03b06 |
| human waste | 674 | Bacteria; Firmicutes; Clostridia_SP; Clostridiales_CL; Clostridiales; *Eubacterium*_FM; sfA; 674; DQ801230.1 gg_id: 175764 human fecal clone RL116__aaf02a04 |
| human waste | 678 | Bacteria; Firmicutes; Clostridia_SP; Clostridiales_CL; Clostridiales; *Eubacterium*_FM; sfA; 678; DQ325771.1 gg_id: 148525 Metagenomic gut microbiome healthy human stool clone B453 |
| human waste | 679 | Bacteria; Firmicutes; Clostridia_SP; Clostridiales_CL; Clostridiales; *Eubacterium*_FM; sfA; 679; DQ824826.1 gg_id: 182348 human fecal clone RL185__aao69g03 |
| human waste | 693 | Bacteria; Firmicutes; Clostridia_SP; Clostridiales_CL; Clostridiales; *Eubacterium*_FM; sfA; 693; DQ326749.1 gg_id: 149241 Metagenomic gut microbiome healthy human stool clone E209 |
| human waste | 757 | Bacteria; Firmicutes; Clostridia_SP; Clostridiales_CL; Clostridiales; *Eubacterium*_FM; sfA; 757; DQ794824.1 gg_id: 197102 human fecal clone RL240__aaj32g12 |
| human waste | 758 | Bacteria; Firmicutes; Clostridia_SP; Clostridiales_CL; Clostridiales; *Eubacterium*_FM; sfA; 758; AY980017.1 gg_id: 119222 human rectum mucosal biopsy clone KA01 |

TABLE 3-continued

Sewage ID taxa
HUMAN WASTE IDENTIFIER TAXA

| Source | #OTU ID | Lineage for representative OTU |
|---|---|---|
| human waste | 784 | Bacteria; Firmicutes; Clostridia_SP; Clostridiales_CL; Clostridiales; *Eubacterium*_FM; sfA; 784; DQ803257.1 gg_id: 181536 human fecal clone RL311__aam23a05 |
| human waste | 795 | Bacteria; Firmicutes; Clostridia_SP; Clostridiales_CL; Clostridiales; *Eubacterium*_FM; sfA; 795; DQ804566.1 gg_id: 189198 human fecal clone RL187__aao69g04 |
| human waste | 817 | Bacteria; Firmicutes; Clostridia_SP; Clostridiales_CL; Clostridiales; *Eubacterium*_FM; sfA; 817; DQ794774.1 gg_id: 198615 human fecal clone RL240__aaj32b10 |
| human waste | 864 | Bacteria; Firmicutes; Clostridia_SP; Clostridiales_CL; Clostridiales; *Eubacterium*_FM; sfA; 864; DQ795497.1 gg_id: 186784 human fecal clone RL178__aan65b04 |
| human waste | 886 | Bacteria; Firmicutes; Clostridia_SP; Clostridiales_CL; Clostridiales; *Eubacterium*_FM; sfA; 886; DQ795588.1 gg_id: 198110 human fecal clone RL178__aan66f08 |
| human waste | 963 | Bacteria; Firmicutes; Clostridia_SP; Clostridiales_CL; Clostridiales; *Eubacterium*_FM; sfA; 963; AY169428.1 gg_id: 81674 rectale |
| human waste | 978 | Bacteria; Firmicutes; Clostridia_SP; Clostridiales_CL; Clostridiales; *Eubacterium*_FM; sfA; 978; DQ802108.1 gg_id: 182412 human fecal clone RL241__aaj03b10 |
| human waste | 997 | Bacteria; Firmicutes; Clostridia_SP; Clostridiales_CL; Clostridiales; *Eubacterium*_FM; sfA; 997; DQ795247.1 gg_id: 193806 human fecal clone RL178__aah51h12 |
| human waste | 998 | Bacteria; Firmicutes; Clostridia_SP; Clostridiales_CL; Clostridiales; *Eubacterium*_FM; sfA; 998; DQ806643.1 gg_id: 174722 human fecal clone RL186__aao47b02 |
| human waste | 36329 | Bacteria; Firmicutes; Clostridia_SP; Clostridiales_CL; Clostridiales; *Faecalibacterium*_FM; sfA; 36329; AY977006.1 gg_id: 123849 human cecum mucosal biopsy clone K680 |
| human waste | 36330 | Bacteria; Firmicutes; Clostridia_SP; Clostridiales_CL; Clostridiales; *Faecalibacterium*_FM; sfA; 36330; AY976537.1 gg_id: 125456 human cecum mucosal biopsy clone K068 |
| human waste | 36331 | Bacteria; Firmicutes; Clostridia_SP; Clostridiales_CL; Clostridiales; *Faecalibacterium*_FM; sfA; 36331; AY980286.1 gg_id: 125611 human rectum mucosal biopsy clone MX86 |
| human waste | 36343 | Bacteria; Firmicutes; Clostridia_SP; Clostridiales_CL; Clostridiales; *Faecalibacterium*_FM; sfA; 36343; DQ326207.1 gg_id: 146365 Metagenomic gut microbiome healthy human stool clone C125 |
| human waste | 36367 | Bacteria; Firmicutes; Clostridia_SP; Clostridiales_CL; Clostridiales; *Faecalibacterium*_FM; sfA; 36367; AY975989.1 gg_id: 122299 human ascending colon mucosal biopsy clone LT21 |
| human waste | 36374 | Bacteria; Firmicutes; Clostridia_SP; Clostridiales_CL; Clostridiales; *Faecalibacterium*_FM; sfA; 36374; DQ805240.1 gg_id: 189932 human fecal clone RL249__aaj83f01 |
| human waste | 36376 | Bacteria; Firmicutes; Clostridia_SP; Clostridiales_CL; Clostridiales; *Faecalibacterium*_FM; sfA; 36376; AY986316.1 gg_id: 118427 human stool clone D709 |
| human waste | 36380 | Bacteria; Firmicutes; Clostridia_SP; Clostridiales_CL; Clostridiales; *Faecalibacterium*_FM; sfA; 36380; DQ802522.1 gg_id: 179153 human fecal clone RL188__aah18h08 |
| human waste | 36388 | Bacteria; Firmicutes; Clostridia_SP; Clostridiales_CL; Clostridiales; *Faecalibacterium*_FM; sfA; 36388; DQ801896.1 gg_id: 182847 human fecal clone RL201__aai48c01 |
| human waste | 36395 | Bacteria; Firmicutes; Clostridia_SP; Clostridiales_CL; Clostridiales; *Faecalibacterium*_FM; sfA; 36395; EF403369.1 gg_id: 208110 human fecal clone SJTU_A1_7_30 |
| human waste | 36415 | Bacteria; Firmicutes; Clostridia_SP; Clostridiales_CL; Clostridiales; *Faecalibacterium*_FM; sfA; 36415; DQ797274.1 gg_id: 194891 human fecal clone RL248__aai97b12 |
| human waste | 36431 | Bacteria; Firmicutes; Clostridia_SP; Clostridiales_CL; Clostridiales; *Faecalibacterium*_FM; sfA; 36431; DQ795954.1 gg_id: 191184 human fecal clone RL202__aai49d06 |
| human waste | 36432 | Bacteria; Firmicutes; Clostridia_SP; Clostridiales_CL; Clostridiales; *Faecalibacterium*_FM; sfA; 36432; AY983650.1 gg_id: 125316 human descending colon mucosal biopsy clone NP13 |
| human waste | 36433 | Bacteria; Firmicutes; Clostridia_SP; Clostridiales_CL; Clostridiales; *Faecalibacterium*_FM; sfA; 36433; DQ795930.1 gg_id: 178865 human fecal clone RL202__aai49b02 |
| human waste | 36444 | Bacteria; Firmicutes; Clostridia_SP; Clostridiales_CL; Clostridiales; *Faecalibacterium*_FM; sfA; 36444; DQ797125.1 gg_id: 194262 human fecal clone RL386__aao87c10 |
| human waste | 36461 | Bacteria; Firmicutes; Clostridia_SP; Clostridiales_CL; Clostridiales; *Faecalibacterium*_FM; sfA; 36461; DQ797310.1 gg_id: 197292 human fecal clone RL248__aai97f08 |
| human waste | 36468 | Bacteria; Firmicutes; Clostridia_SP; Clostridiales_CL; Clostridiales; *Faecalibacterium*_FM; sfA; 36468; DQ808851.1 gg_id: 192569 human fecal clone RL243__aai86b07 |
| human waste | 36471 | Bacteria; Firmicutes; Clostridia_SP; Clostridiales_CL; Clostridiales; *Faecalibacterium*_FM; sfA; 36471; AY980688.1 gg_id: 117731 human rectum mucosal biopsy clone LM11 |
| human waste | 36482 | Bacteria; Firmicutes; Clostridia_SP; Clostridiales_CL; Clostridiales; *Faecalibacterium*_FM; sfA; 36482; AY984427.1 gg_id: 119554 human stool clone B337 |
| human waste | 36484 | Bacteria; Firmicutes; Clostridia_SP; Clostridiales_CL; Clostridiales; *Faecalibacterium*_FM; sfA; 36484; AY975246.1 gg_id: 123379 human ascending colon mucosal biopsy clone N415 |
| human waste | 36485 | Bacteria; Firmicutes; Clostridia_SP; Clostridiales_CL; Clostridiales; *Faecalibacterium*_FM; sfA; 36485; DQ799520.1 gg_id: 198837 human fecal clone RL305aal87c05 |
| human waste | 36486 | Bacteria; Firmicutes; Clostridia_SP; Clostridiales_CL; Clostridiales; *Faecalibacterium*_FM; sfA; 36486; AY986249.1 gg_id: 127846 human stool clone D624 |
| human waste | 36490 | Bacteria; Firmicutes; Clostridia_SP; Clostridiales_CL; Clostridiales; *Faecalibacterium*_FM; sfA; 36490; AY980222.1 gg_id: 121082 human rectum mucosal biopsy clone KF57 |
| human waste | 36492 | Bacteria; Firmicutes; Clostridia_SP; Clostridiales_CL; Clostridiales; *Faecalibacterium*_FM; sfA; 36492; DQ808624.1 gg_id: 174050 human fecal clone RL239__aaj11b01 |
| human waste | 36493 | Bacteria; Firmicutes; Clostridia_SP; Clostridiales_CL; Clostridiales; *Faecalibacterium*_FM; sfA; 36493; DQ801133.1 gg_id: 183347 human fecal clone RL387__aao92g04 |
| human waste | 36501 | Bacteria; Firmicutes; Clostridia_SP; Clostridiales_CL; Clostridiales; *Faecalibacterium*_FM; sfA; 36501; AY981146.1 gg_id: 119144 human sigmoid colon mucosal biopsy clone G078 |
| human waste | 36502 | Bacteria; Firmicutes; Clostridia_SP; Clostridiales_CL; Clostridiales; *Faecalibacterium*_FM; sfA; 36502; EF404990.1 gg_id: 204308 human fecal clone SJTU_G_05_56 |
| human waste | 36538 | Bacteria; Firmicutes; Clostridia_SP; Clostridiales_CL; Clostridiales; *Faecalibacterium*_FM; sfA; 36538; DQ801422.1 gg_id: 178266 human fecal clone RL388__aao95c10 |

TABLE 3-continued

Sewage ID taxa
HUMAN WASTE IDENTIFIER TAXA

| Source | #OTU ID | Lineage for representative OTU |
|---|---|---|
| human waste | 36546 | Bacteria; Firmicutes; Clostridia_SP; Clostridiales_CL; Clostridiales; *Faecalibacterium*_FM; sfA; 36546; DQ441336.1 gg_id: 187032 human intestinal biopsy clone CD85 |
| human waste | 36551 | Bacteria; Firmicutes; Clostridia_SP; Clostridiales_CL; Clostridiales; *Faecalibacterium*_FM; sfA; 36551; DQ441338.1 gg_id: 192337 human intestinal biopsy clone CD87 |
| human waste | 36565 | Bacteria; Firmicutes; Clostridia_SP; Clostridiales_CL; Clostridiales; *Faecalibacterium*_FM; sfA; 36565; DQ904772.1 gg_id: 164793 human fecal clone 001B-d2 |
| human waste | 36573 | Bacteria; Firmicutes; Clostridia_SP; Clostridiales_CL; Clostridiales; *Faecalibacterium*_FM; sfA; 36573; EF402820.1 gg_id: 204227 human fecal clone SJTU_B_12_93 |
| human waste | 36591 | Bacteria; Firmicutes; Clostridia_SP; Clostridiales_CL; Clostridiales; *Faecalibacterium*_FM; sfA; 36591; DQ801779.1 gg_id: 191041 human fecal clone RL201_aai46f10 |
| human waste | 36595 | Bacteria; Firmicutes; Clostridia_SP; Clostridiales_CL; Clostridiales; *Faecalibacterium*_FM; sfA; 36595; DQ801519.1 gg_id: 199423 human fecal clone RL388_aao96e10 |
| human waste | 36596 | Bacteria; Firmicutes; Clostridia_SP; Clostridiales_CL; Clostridiales; *Faecalibacterium*_FM; sfA; 36596; EF402799.1 gg_id: 204787 human fecal clone SJTU_B_12_66 |
| human waste | 36598 | Bacteria; Firmicutes; Clostridia_SP; Clostridiales_CL; Clostridiales; *Faecalibacterium*_FM; sfA; 36598; DQ801297.1 gg_id: 194547 human fecal clone RL388_aao93e12 |
| human waste | 36613 | Bacteria; Firmicutes; Clostridia_SP; Clostridiales_CL; Clostridiales; *Faecalibacterium*_FM; sfA; 36613; DQ798149.1 gg_id: 181186 human fecal clone RL302_aal96b04 |
| human waste | 36619 | Bacteria; Firmicutes; Clostridia_SP; Clostridiales_CL; Clostridiales; *Faecalibacterium*_FM; sfA; 36619; EF403892.1 gg_id: 204401 human fecal clone SJTU_C_02_03 |
| human waste | 36622 | Bacteria; Firmicutes; Clostridia_SP; Clostridiales_CL; Clostridiales; *Faecalibacterium*_FM; sfA; 36622; EF400748.1 gg_id: 214296 human fecal clone SJTU_D_01_07 |
| human waste | 36650 | Bacteria; Firmicutes; Clostridia_SP; Clostridiales_CL; Clostridiales; *Faecalibacterium*_FM; sfA; 36650; DQ801530.1 gg_id: 183361 human fecal clone RL388_aao96f11 |
| human waste | 36659 | Bacteria; Firmicutes; Clostridia_SP; Clostridiales_CL; Clostridiales; *Faecalibacterium*_FM; sfA; 36659; DQ904831.1 gg_id: 171400 human fecal clone 001C-a5 |
| human waste | 36660 | Bacteria; Firmicutes; Clostridia_SP; Clostridiales_CL; Clostridiales; *Faecalibacterium*_FM; sfA; 36660; DQ800745.1 gg_id: 175486 human fecal clone RL183_aao02h05 |
| human waste | 36661 | Bacteria; Firmicutes; Clostridia_SP; Clostridiales_CL; Clostridiales; *Faecalibacterium*_FM; sfA; 36661; DQ808489.1 gg_id: 178182 human fecal clone RL239_aaj09c01 |
| human waste | 36665 | Bacteria; Firmicutes; Clostridia_SP; Clostridiales_CL; Clostridiales; *Faecalibacterium*_FM; sfA; 36665; AY985869.1 gg_id: 117448 human stool clone D146 |
| human waste | 36668 | Bacteria; Firmicutes; Clostridia_SP; Clostridiales_CL; Clostridiales; *Faecalibacterium*_FM; sfA; 36668; DQ806390.1 gg_id: 179394 human fecal clone RL186_aan91f06 |
| human waste | 36676 | Bacteria; Firmicutes; Clostridia_SP; Clostridiales_CL; Clostridiales; *Faecalibacterium*_FM; sfA; 36676; DQ799907.1 gg_id: 181690 human fecal clone RL247_aaj21f07 |
| human waste | 36691 | Bacteria; Firmicutes; Clostridia_SP; Clostridiales_CL; Clostridiales; *Faecalibacterium*_FM; sfA; 36691; AY982709.1 gg_id: 125629 human descending colon mucosal biopsy clone KY23 |
| human waste | 36693 | Bacteria; Firmicutes; Clostridia_SP; Clostridiales_CL; Clostridiales; *Faecalibacterium*_FM; sfA; 36693; DQ805915.1 gg_id: 198310 human fecal clone RL306aal92f03 |
| human waste | 36695 | Bacteria; Firmicutes; Clostridia_SP; Clostridiales_CL; Clostridiales; *Faecalibacterium*_FM; sfA; 36695; EF401430.1 gg_id: 204196 human fecal clone SJTU_D_10_29 |
| human waste | 36703 | Bacteria; Firmicutes; Clostridia_SP; Clostridiales_CL; Clostridiales; *Faecalibacterium*_FM; sfA; 36703; AY979514.1 gg_id: 119264 human transverse colon mucosal biopsy clone M160 |
| human waste | 36707 | Bacteria; Firmicutes; Clostridia_SP; Clostridiales_CL; Clostridiales; *Faecalibacterium*_FM; sfA; 36707; DQ823885.1 gg_id: 180532 human fecal clone RL250_aaj80d09 |
| human waste | 36708 | Bacteria; Firmicutes; Clostridia_SP; Clostridiales_CL; Clostridiales; *Faecalibacterium*_FM; sfA; 36708; AY978923.1 gg_id: 117550 human transverse colon mucosal biopsy clone NG48 |
| human waste | 36724 | Bacteria; Firmicutes; Clostridia_SP; Clostridiales_CL; Clostridiales; *Faecalibacterium*_FM; sfA; 36724; EF403431.1 gg_id: 204947 human fecal clone SJTU_A2_01_09 |
| human waste | 36727 | Bacteria; Firmicutes; Clostridia_SP; Clostridiales_CL; Clostridiales; *Faecalibacterium*_FM; sfA; 36727; DQ904721.1 gg_id: 161730 human fecal clone 001-h11 |
| human waste | 36746 | Bacteria; Firmicutes; Clostridia_SP; Clostridiales_CL; Clostridiales; *Faecalibacterium*_FM; sfA; 36746; DQ800622.1 gg_id: 195806 human fecal clone RL183_aao01c01 |
| human waste | 36751 | Bacteria; Firmicutes; Clostridia_SP; Clostridiales_CL; Clostridiales; *Faecalibacterium*_FM; sfA; 36751; DQ798882.1 gg_id: 181370 human fecal clone RL242_aaj98f02 |
| human waste | 36759 | Bacteria; Firmicutes; Clostridia_SP; Clostridiales_CL; Clostridiales; *Faecalibacterium*_FM; sfA; 36759; EF401541.1 gg_id: 206989 human fecal clone SJTU_D_12_08 |
| human waste | 36760 | Bacteria; Firmicutes; Clostridia_SP; Clostridiales_CL; Clostridiales; *Faecalibacterium*_FM; sfA; 36760; DQ806469.1 gg_id: 191959 human fecal clone RL186_aao45a09 |
| human waste | 36767 | Bacteria; Firmicutes; Clostridia_SP; Clostridiales_CL; Clostridiales; *Faecalibacterium*_FM; sfA; 36767; DQ805302.1 gg_id: 181045 human fecal clone RL249_aaj84g09 |
| human waste | 36789 | Bacteria; Firmicutes; Clostridia_SP; Clostridiales_CL; Clostridiales; *Faecalibacterium*_FM; sfA; 36789; DQ806501.1 gg_id: 174551 human fecal clone RL186_aao45d07 |
| human waste | 36793 | Bacteria; Firmicutes; Clostridia_SP; Clostridiales_CL; Clostridiales; *Faecalibacterium*_FM; sfA; 36793; EF403207.1 gg_id: 203984 human fecal clone SJTU_A1_6_52 |
| human waste | 36800 | Bacteria; Firmicutes; Clostridia_SP; Clostridiales_CL; Clostridiales; *Faecalibacterium*_FM; sfA; 36800; DQ797136.1 gg_id: 194708 human fecal clone RL386_aao87d10 |
| human waste | 36802 | Bacteria; Firmicutes; Clostridia_SP; Clostridiales_CL; Clostridiales; *Faecalibacterium*_FM; sfA; 36802; DQ802304.1 gg_id: 197773 human fecal clone RL188_aah15g12 |
| human waste | 36810 | Bacteria; Firmicutes; Clostridia_SP; Clostridiales_CL; Clostridiales; *Faecalibacterium*_FM; sfA; 36810; DQ801114.1 gg_id: 175937 human fecal clone RL387_aao92d09 |
| human waste | 36813 | Bacteria; Firmicutes; Clostridia_SP; Clostridiales_CL; Clostridiales; *Faecalibacterium*_FM; sfA; 36813; AJ413954.1 gg_id: 27866 *Faecalibacterium prausnitzii* str. ATCC 27768 |

TABLE 3-continued

Sewage ID taxa
HUMAN WASTE IDENTIFIER TAXA

| Source | #OTU ID | Lineage for representative OTU |
|---|---|---|
| human waste | 36821 | Bacteria; Firmicutes; Clostridia_SP; Clostridiales_CL; Clostridiales; *Faecalibacterium*_FM; sfA; 36821; DQ824456.1 gg_id: 193985 human fecal clone RL304__aal76c03 |
| human waste | 36822 | Bacteria; Firmicutes; Clostridia_SP; Clostridiales_CL; Clostridiales; *Faecalibacterium*_FM; sfA; 36822; DQ806450.1 gg_id: 193849 human fecal clone RL186__aan92f06 |
| human waste | 36825 | Bacteria; Firmicutes; Clostridia_SP; Clostridiales_CL; Clostridiales; *Faecalibacterium*_FM; sfA; 36825; EF401740.1 gg_id: 205149 human fecal clone SJTU__D__15__65 |
| human waste | 36835 | Bacteria; Firmicutes; Clostridia_SP; Clostridiales_CL; Clostridiales; *Faecalibacterium*_FM; sfA; 36835; AY980091.1 gg_id: 126990 human rectum mucosal biopsy clone KB76 |
| human waste | 36836 | Bacteria; Firmicutes; Clostridia_SP; Clostridiales_CL; Clostridiales; *Faecalibacterium*_FM; sfA; 36836; EF403782.1 gg_id: 206554 human fecal clone SJTU__A2__02__28 |
| human waste | 36840 | Bacteria; Firmicutes; Clostridia_SP; Clostridiales_CL; Clostridiales; *Faecalibacterium*_FM; sfA; 36840; DQ804770.1 gg_id: 186418 human fecal clone RL187__aao72e03 |
| human waste | 36857 | Bacteria; Firmicutes; Clostridia_SP; Clostridiales_CL; Clostridiales; *Faecalibacterium*_FM; sfA; 36857; DQ805171.1 gg_id: 189368 human fecal clone RL249__aaj82e01 |
| human waste | 36859 | Bacteria; Firmicutes; Clostridia_SP; Clostridiales_CL; Clostridiales; *Faecalibacterium*_FM; sfA; 36859; DQ801846.1 gg_id: 198049 human fecal clone RL201__aai47f01 |
| human waste | 36863 | Bacteria; Firmicutes; Clostridia_SP; Clostridiales_CL; Clostridiales; *Faecalibacterium*_FM; sfA; 36863; EF404156.1 gg_id: 206612 human fecal clone SJTU__C__05__49 |
| human waste | 36872 | Bacteria; Firmicutes; Clostridia_SP; Clostridiales_CL; Clostridiales; *Faecalibacterium*_FM; sfA; 36872; DQ796992.1 gg_id: 195038 human fecal clone RL386__aao85e04 |
| human waste | 36875 | Bacteria; Firmicutes; Clostridia_SP; Clostridiales_CL; Clostridiales; *Faecalibacterium*_FM; sfA; 36875; DQ806371.1 gg_id: 184697 human fecal clone RL186__aan91d03 |
| human waste | 36881 | Bacteria; Firmicutes; Clostridia_SP; Clostridiales_CL; Clostridiales; *Faecalibacterium*_FM; sfA; 36881; DQ805679.1 gg_id: 178456 human fecal clone RL306aal89g02 |
| human waste | 36889 | Bacteria; Firmicutes; Clostridia_SP; Clostridiales_CL; Clostridiales; *Faecalibacterium*_FM; sfA; 36889; AY985204.1 gg_id: 118549 human stool clone C067 |
| human waste | 36892 | Bacteria; Firmicutes; Clostridia_SP; Clostridiales_CL; Clostridiales; *Faecalibacterium*_FM; sfA; 36892; DQ806552.1 gg_id: 174017 human fecal clone RL186__aao46a04 |
| human waste | 36901 | Bacteria; Firmicutes; Clostridia_SP; Clostridiales_CL; Clostridiales; *Faecalibacterium*_FM; sfA; 36901; DQ798421.1 gg_id: 183168 human fecal clone RL181__aah42d04 |
| human waste | 36902 | Bacteria; Firmicutes; Clostridia_SP; Clostridiales_CL; Clostridiales; *Faecalibacterium*_FM; sfA; 36902; DQ798705.1 gg_id: 190561 human fecal clone RL181__aao00d02 |
| human waste | 36907 | Bacteria; Firmicutes; Clostridia_SP; Clostridiales_CL; Clostridiales; *Faecalibacterium*_FM; sfA; 36907; EF403514.1 gg_id: 205820 human fecal clone SJTU__A2__02__53 |
| human waste | 36916 | Bacteria; Firmicutes; Clostridia_SP; Clostridiales_CL; Clostridiales; *Faecalibacterium*_FM; sfA; 36916; AY978614.1 gg_id: 117465 human transverse colon mucosal biopsy clone KS17 |
| human waste | 36920 | Bacteria; Firmicutes; Clostridia_SP; Clostridiales_CL; Clostridiales; *Faecalibacterium*_FM; sfA; 36920; DQ799430.1 gg_id: 185458 human fecal clone RL305aal86b09 |
| human waste | 36922 | Bacteria; Firmicutes; Clostridia_SP; Clostridiales_CL; Clostridiales; *Faecalibacterium*_FM; sfA; 36922; DQ798647.1 gg_id: 191168 human fecal clone RL181__aan99e06 |
| human waste | 36929 | Bacteria; Firmicutes; Clostridia_SP; Clostridiales_CL; Clostridiales; *Faecalibacterium*_FM; sfA; 36929; DQ904644.1 gg_id: 171028 human fecal clone 001-a5 |
| human waste | 36938 | Bacteria; Firmicutes; Clostridia_SP; Clostridiales_CL; Clostridiales; *Faecalibacterium*_FM; sfA; 36938; DQ825301.1 gg_id: 189448 human fecal clone RL185__aan88b03 |
| human waste | 36945 | Bacteria; Firmicutes; Clostridia_SP; Clostridiales_CL; Clostridiales; *Faecalibacterium*_FM; sfA; 36945; DQ805620.1 gg_id: 186146 human fecal clone RL306aal89a09 |
| human waste | 36951 | Bacteria; Firmicutes; Clostridia_SP; Clostridiales_CL; Clostridiales; *Faecalibacterium*_FM; sfA; 36951; DQ798017.1 gg_id: 180335 human fecal clone RL302__aal94f01 |
| human waste | 36958 | Bacteria; Firmicutes; Clostridia_SP; Clostridiales_CL; Clostridiales; *Faecalibacterium*_FM; sfA; 36958; AY979205.1 gg_id: 119098 human transverse colon mucosal biopsy clone Z327 |
| human waste | 36967 | Bacteria; Firmicutes; Clostridia_SP; Clostridiales_CL; Clostridiales; *Faecalibacterium*_FM; sfA; 36967; AY976344.1 gg_id: 123881 human ascending colon mucosal biopsy clone LY20 |
| human waste | 36969 | Bacteria; Firmicutes; Clostridia_SP; Clostridiales_CL; Clostridiales; *Faecalibacterium*_FM; sfA; 36969; EU530480.1 gg_id: 261273 mucosa adherent and invasive microbes profile adenoma colorectal cancer clone M7-59 |
| human waste | 36983 | Bacteria; Firmicutes; Clostridia_SP; Clostridiales_CL; Clostridiales; *Faecalibacterium*_FM; sfA; 36983; DQ801139.1 gg_id: 177430 human fecal clone RL387__aao92g11 |
| human waste | 36995 | Bacteria; Firmicutes; Clostridia_SP; Clostridiales_CL; Clostridiales; *Faecalibacterium*_FM; sfA; 36995; DQ808865.1 gg_id: 195824 human fecal clone RL243__aai86c10 |
| human waste | 37000 | Bacteria; Firmicutes; Clostridia_SP; Clostridiales_CL; Clostridiales; *Faecalibacterium*_FM; sfA; 37000; DQ801271.1 gg_id: 198242 human fecal clone RL388__aao93c06 |
| human waste | 37033 | Bacteria; Firmicutes; Clostridia_SP; Clostridiales_CL; Clostridiales; *Faecalibacterium*_FM; sfA; 37033; AY978113.1 gg_id: 117670 human cecum mucosal biopsy clone LI82 |
| human waste | 37034 | Bacteria; Firmicutes; Clostridia_SP; Clostridiales_CL; Clostridiales; *Faecalibacterium*_FM; sfA; 37034; AY983309.1 gg_id: 115692 human descending colon mucosal biopsy clone A354 |
| human waste | 37037 | Bacteria; Firmicutes; Clostridia_SP; Clostridiales_CL; Clostridiales; *Faecalibacterium*_FM; sfA; 37037; AY979770.1 gg_id: 116321 human transverse colon mucosal biopsy clone M531 |
| human waste | 37039 | Bacteria; Firmicutes; Clostridia_SP; Clostridiales_CL; Clostridiales; *Faecalibacterium*_FM; sfA; 37039; DQ806550.1 gg_id: 177636 human fecal clone RL186__aao46a01 |
| human waste | 37044 | Bacteria; Firmicutes; Clostridia_SP; Clostridiales_CL; Clostridiales; *Faecalibacterium*_FM; sfA; 37044; DQ810166.1 gg_id: 187387 human fecal clone RL184__aao68g09 |
| human waste | 37054 | Bacteria; Firmicutes; Clostridia_SP; Clostridiales_CL; Clostridiales; *Faecalibacterium*_FM; sfA; 37054; EU530466.1 gg_id: 264386 mucosa adherent and invasive microbes profile adenoma colorectal cancer clone M7-38 |
| human waste | 37064 | Bacteria; Firmicutes; Clostridia_SP; Clostridiales_CL; Clostridiales; *Faecalibacterium*_FM; sfA; 37064; AY977759.1 gg_id: 126848 human cecum mucosal biopsy clone LE35 |

TABLE 3-continued

Sewage ID taxa
HUMAN WASTE IDENTIFIER TAXA

| Source | #OTU ID | Lineage for representative OTU |
|---|---|---|
| human waste | 37066 | Bacteria; Firmicutes; Clostridia_SP; Clostridiales_CL; Clostridiales; *Faecalibacterium*_FM; sfA; 37066; DQ797657.1 gg_id: 199518 human fecal clone RL206__aaj14c10 |
| human waste | 37070 | Bacteria; Firmicutes; Clostridia_SP; Clostridiales_CL; Clostridiales; *Faecalibacterium*_FM; sfA; 37070; AY978106.1 gg_id: 116676 human cecum mucosal biopsy clone LI74 |
| human waste | 37080 | Bacteria; Firmicutes; Clostridia_SP; Clostridiales_CL; Clostridiales; *Faecalibacterium*_FM; sfA; 37080; DQ325773.1 gg_id: 145129 Metagenomic gut microbiome healthy human stool clone B456 |
| human waste | 37094 | Bacteria; Firmicutes; Clostridia_SP; Clostridiales_CL; Clostridiales; *Faecalibacterium*_FM; sfA; 37094; AY976930.1 gg_id: 126260 human cecum mucosal biopsy clone K583 |
| human waste | 37116 | Bacteria; Firmicutes; Clostridia_SP; Clostridiales_CL; Clostridiales; *Faecalibacterium*_FM; sfA; 37116; EF404629.1 gg_id: 206291 human fecal clone SJTU_C_13_72 |
| human waste | 37125 | Bacteria; Firmicutes; Clostridia_SP; Clostridiales_CL; Clostridiales; *Faecalibacterium*_FM; sfA; 37125; DQ795919.1 gg_id: 182156 human fecal clone RL245__aai84h09 |
| human waste | 37132 | Bacteria; Firmicutes; Clostridia_SP; Clostridiales_CL; Clostridiales; *Faecalibacterium*_FM; sfA; 37132; AY977388.1 gg_id: 120286 human cecum mucosal biopsy clone W035 |
| human waste | 37135 | Bacteria; Firmicutes; Clostridia_SP; Clostridiales_CL; Clostridiales; *Faecalibacterium*_FM; sfA; 37135; DQ802295.1 gg_id: 190903 human fecal clone RL188__aah15g02 |
| human waste | 37138 | Bacteria; Firmicutes; Clostridia_SP; Clostridiales_CL; Clostridiales; *Faecalibacterium*_FM; sfA; 37138; AY981882.1 gg_id: 124273 human sigmoid colon mucosal biopsy clone NX70 |
| human waste | 37139 | Bacteria; Firmicutes; Clostridia_SP; Clostridiales_CL; Clostridiales; *Faecalibacterium*_FM; sfA; 37139; DQ823721.1 gg_id: 175507 human fecal clone RL250__aaj78b08 |
| human waste | 37151 | Bacteria; Firmicutes; Clostridia_SP; Clostridiales_CL; Clostridiales; *Faecalibacterium*_FM; sfA; 37151; DQ825147.1 gg_id: 193482 human fecal clone RL185__aan85h07 |
| human waste | 37154 | Bacteria; Firmicutes; Clostridia_SP; Clostridiales_CL; Clostridiales; *Faecalibacterium*_FM; sfA; 37154; DQ905762.2 gg_id: 163379 human fecal clone 29A-f5 |
| human waste | 37155 | Bacteria; Firmicutes; Clostridia_SP; Clostridiales_CL; Clostridiales; *Faecalibacterium*_FM; sfA; 37155; AY981706.1 gg_id: 116922 human sigmoid colon mucosal biopsy clone LA73 |
| human waste | 37156 | Bacteria; Firmicutes; Clostridia_SP; Clostridiales_CL; Clostridiales; *Faecalibacterium*_FM; sfA; 37156; DQ797013.1 gg_id: 193800 human fecal clone RL386__aao85g06 |
| human waste | 37177 | Bacteria; Firmicutes; Clostridia_SP; Clostridiales_CL; Clostridiales; *Faecalibacterium*_FM; sfA; 37177; DQ802273.1 gg_id: 181729 human fecal clone RL188__aah15d11 |
| human waste | 37181 | Bacteria; Firmicutes; Clostridia_SP; Clostridiales_CL; Clostridiales; *Faecalibacterium*_FM; sfA; 37181; DQ326121.1 gg_id: 146257 Metagenomic gut microbiome healthy human stool clone BB84 |
| human waste | 37182 | Bacteria; Firmicutes; Clostridia_SP; Clostridiales_CL; Clostridiales; *Faecalibacterium*_FM; sfA; 37182; DQ823774.1 gg_id: 184088 human fecal clone RL250__aaj78h08 |
| human waste | 37190 | Bacteria; Firmicutes; Clostridia_SP; Clostridiales_CL; Clostridiales; *Faecalibacterium*_FM; sfA; 37190; AY976039.1 gg_id: 127495 human ascending colon mucosal biopsy clone LT85 |
| human waste | 37193 | Bacteria; Firmicutes; Clostridia_SP; Clostridiales_CL; Clostridiales; *Faecalibacterium*_FM; sfA; 37193; DQ801576.1 gg_id: 180747 human fecal clone RL117__aae91g07 |
| human waste | 37209 | Bacteria; Firmicutes; Clostridia_SP; Clostridiales_CL; Clostridiales; *Faecalibacterium*_FM; sfA; 37209; AY979261.1 gg_id: 127242 human transverse colon mucosal biopsy clone Z454 |
| human waste | 37231 | Bacteria; Firmicutes; Clostridia_SP; Clostridiales_CL; Clostridiales; *Faecalibacterium*_FM; sfA; 37231; AY916168.1 gg_id: 112968 human transverse colon biopsy clone M507 |
| human waste | 37243 | Bacteria; Firmicutes; Clostridia_SP; Clostridiales_CL; Clostridiales; *Faecalibacterium*_FM; sfA; 37243; DQ825316.1 gg_id: 185349 human fecal clone RL185__aan88d06 |
| human waste | 37249 | Bacteria; Firmicutes; Clostridia_SP; Clostridiales_CL; Clostridiales; *Faecalibacterium*_FM; sfA; 37249; DQ800409.1 gg_id: 177875 human fecal clone RL303__aal72g12 |
| human waste | 37259 | Bacteria; Firmicutes; Clostridia_SP; Clostridiales_CL; Clostridiales; *Faecalibacterium*_FM; sfA; 37259; DQ796459.1 gg_id: 188277 human fecal clone RL179__aah28f11 |
| human waste | 37273 | Bacteria; Firmicutes; Clostridia_SP; Clostridiales_CL; Clostridiales; *Faecalibacterium*_FM; sfA; 37273; DQ806536.1 gg_id: 175819 human fecal clone RL186__aao45g10 |
| human waste | 37279 | Bacteria; Firmicutes; Clostridia_SP; Clostridiales_CL; Clostridiales; *Faecalibacterium*_FM; sfA; 37279; DQ800925.1 gg_id: 182746 human fecal clone RL387__aao89d05 |
| human waste | 37281 | Bacteria; Firmicutes; Clostridia_SP; Clostridiales_CL; Clostridiales; *Faecalibacterium*_FM; sfA; 37281; DQ798003.1 gg_id: 189642 human fecal clone RL302__aal94d07 |
| human waste | 37294 | Bacteria; Firmicutes; Clostridia_SP; Clostridiales_CL; Clostridiales; *Faecalibacterium*_FM; sfA; 37294; DQ805106.1 gg_id: 187530 human fecal clone RL249__aaj81c10 |
| human waste | 37295 | Bacteria; Firmicutes; Clostridia_SP; Clostridiales_CL; Clostridiales; *Faecalibacterium*_FM; sfA; 37295; DQ800981.1 gg_id: 191715 human fecal clone RL387__aao90c08 |
| human waste | 37297 | Bacteria; Firmicutes; Clostridia_SP; Clostridiales_CL; Clostridiales; *Faecalibacterium*_FM; sfA; 37297; DQ796847.1 gg_id: 184231 human fecal clone RL179__aao55d05 |
| human waste | 37298 | Bacteria; Firmicutes; Clostridia_SP; Clostridiales_CL; Clostridiales; *Faecalibacterium*_FM; sfA; 37298; EF401474.1 gg_id: 204781 human fecal clone SJTU_D_11_25 |
| human waste | 37303 | Bacteria; Firmicutes; Clostridia_SP; Clostridiales_CL; Clostridiales; *Faecalibacterium*_FM; sfA; 37303; DQ802003.1 gg_id: 196229 human fecal clone RL241__aaj01f12 |
| human waste | 37309 | Bacteria; Firmicutes; Clostridia_SP; Clostridiales_CL; Clostridiales; *Faecalibacterium*_FM; sfA; 37309; AY916270.1 gg_id: 113461 human rectum biopsy clone MZ04 |
| human waste | 37322 | Bacteria; Firmicutes; Clostridia_SP; Clostridiales_CL; Clostridiales; *Faecalibacterium*_FM; sfA; 37322; DQ801207.1 gg_id: 176772 human fecal clone RL116__aaf01b03 |
| human waste | 37328 | Bacteria; Firmicutes; Clostridia_SP; Clostridiales_CL; Clostridiales; *Faecalibacterium*_FM; sfA; 37328; DQ796787.1 gg_id: 193058 human fecal clone RL179__aao54e02 |
| human waste | 37333 | Bacteria; Firmicutes; Clostridia_SP; Clostridiales_CL; Clostridiales; *Faecalibacterium*_FM; sfA; 37333; DQ796987.1 gg_id: 196569 human fecal clone RL386__aao85d07 |
| human waste | 37334 | Bacteria; Firmicutes; Clostridia_SP; Clostridiales_CL; Clostridiales; *Faecalibacterium*_FM; sfA; 37334; AY982868.1 gg_id: 122631 human descending colon mucosal biopsy clone L036 |

TABLE 3-continued

Sewage ID taxa
HUMAN WASTE IDENTIFIER TAXA

| Source | #OTU ID | Lineage for representative OTU |
|---|---|---|
| human waste | 37337 | Bacteria; Firmicutes; Clostridia_SP; Clostridiales_CL; Clostridiales; *Faecalibacterium*_FM; sfA; 37337; AY975600.1 gg_id: 119243 human ascending colon mucosal biopsy clone NB32 |
| human waste | 37342 | Bacteria; Firmicutes; Clostridia_SP; Clostridiales_CL; Clostridiales; *Faecalibacterium*_FM; sfA; 37342; EF401643.1 gg_id: 215940 human fecal clone SJTU_D_13_21 |
| human waste | 37346 | Bacteria; Firmicutes; Clostridia_SP; Clostridiales_CL; Clostridiales; *Faecalibacterium*_FM; sfA; 37346; EF401328.1 gg_id: 216370 human fecal clone SJTU_D_08_86 |
| human waste | 37349 | Bacteria; Firmicutes; Clostridia_SP; Clostridiales_CL; Clostridiales; *Faecalibacterium*_FM; sfA; 37349; EF402108.1 gg_id: 203617 human fecal clone SJTU_B_03_75 |
| human waste | 37366 | Bacteria; Firmicutes; Clostridia_SP; Clostridiales_CL; Clostridiales; *Faecalibacterium*_FM; sfA; 37366; DQ904852.1 gg_id: 168234 human fecal clone 001C-c3 |
| human waste | 37369 | Bacteria; Firmicutes; Clostridia_SP; Clostridiales_CL; Clostridiales; *Faecalibacterium*_FM; sfA; 37369; DQ796042.1 gg_id: 198500 human fecal clone RL202_aai50f07 |
| human waste | 37373 | Bacteria; Firmicutes; Clostridia_SP; Clostridiales_CL; Clostridiales; *Faecalibacterium*_FM; sfA; 37373; DQ796463.1 gg_id: 198114 human fecal clone RL179_aah28g05 |
| human waste | 37385 | Bacteria; Firmicutes; Clostridia_SP; Clostridiales_CL; Clostridiales; *Faecalibacterium*_FM; sfA; 37385; DQ798824.1 gg_id: 191107 human fecal clone RL242_aaj97g11 |
| human waste | 37408 | Bacteria; Firmicutes; Clostridia_SP; Clostridiales_CL; Clostridiales; *Faecalibacterium*_FM; sfA; 37408; AY984467.1 gg_id: 122421 human stool clone B380 |
| human waste | 37409 | Bacteria; Firmicutes; Clostridia_SP; Clostridiales_CL; Clostridiales; *Faecalibacterium*_FM; sfA; 37409; DQ825317.1 gg_id: 188494 human fecal clone RL185_aan88d07 |
| human waste | 37415 | Bacteria; Firmicutes; Clostridia_SP; Clostridiales_CL; Clostridiales; *Faecalibacterium*_FM; sfA; 37415; DQ325893.1 gg_id: 147702 Metagenomic gut microbiome healthy human stool clone B707 |
| human waste | 37417 | Bacteria; Firmicutes; Clostridia_SP; Clostridiales_CL; Clostridiales; *Faecalibacterium*_FM; sfA; 37417; DQ801234.1 gg_id: 184375 human fecal clone RL116_aaf02b06 |
| human waste | 37425 | Bacteria; Firmicutes; Clostridia_SP; Clostridiales_CL; Clostridiales; *Faecalibacterium*_FM; sfA; 37425; AY982232.1 gg_id: 123423 human sigmoid colon mucosal biopsy clone MH43 |
| human waste | 37426 | Bacteria; Firmicutes; Clostridia_SP; Clostridiales_CL; Clostridiales; *Faecalibacterium*_FM; sfA; 37426; DQ798517.1 gg_id: 197692 human fecal clone RL181_aan97f12 |
| human waste | 37445 | Bacteria; Firmicutes; Clostridia_SP; Clostridiales_CL; Clostridiales; *Faecalibacterium*_FM; sfA; 37445; DQ805166.1 gg_id: 184769 human fecal clone RL249_aaj82d03 |
| human waste | 37469 | Bacteria; Firmicutes; Clostridia_SP; Clostridiales_CL; Clostridiales; *Faecalibacterium*_FM; sfA; 37469; DQ796592.1 gg_id: 185714 human fecal clone RL179aan75e06 |
| human waste | 37470 | Bacteria; Firmicutes; Clostridia_SP; Clostridiales_CL; Clostridiales; *Faecalibacterium*_FM; sfA; 37470; AY978978.1 gg_id: 124686 human transverse colon mucosal biopsy clone NH78 |
| human waste | 37472 | Bacteria; Firmicutes; Clostridia_SP; Clostridiales_CL; Clostridiales; *Faecalibacterium*_FM; sfA; 37472; DQ802307.1 gg_id: 176501 human fecal clone RL188_aah15h04 |
| human waste | 37477 | Bacteria; Firmicutes; Clostridia_SP; Clostridiales_CL; Clostridiales; *Faecalibacterium*_FM; sfA; 37477; AY984829.1 gg_id: 120580 human stool clone B792 |
| human waste | 37479 | Bacteria; Firmicutes; Clostridia_SP; Clostridiales_CL; Clostridiales; *Faecalibacterium*_FM; sfA; 37479; DQ805186.1 gg_id: 177457 human fecal clone RL249_aaj82f09 |
| human waste | 37537 | Bacteria; Firmicutes; Clostridia_SP; Clostridiales_CL; Clostridiales; *Faecalibacterium*_FM; sfA; 37537; EF405306.1 gg_id: 207969 human fecal clone SJTU_G_03_91 |
| human waste | 37558 | Bacteria; Firmicutes; Clostridia_SP; Clostridiales_CL; Clostridiales; *Faecalibacterium*_FM; sfA; 37558; AY981462.1 gg_id: 115422 human sigmoid colon mucosal biopsy clone L559 |
| human waste | 37561 | Bacteria; Firmicutes; Clostridia_SP; Clostridiales_CL; Clostridiales; *Faecalibacterium*_FM; sfA; 37561; AY984095.1 gg_id: 125128 human descending colon mucosal biopsy clone MF44 |
| human waste | 37567 | Bacteria; Firmicutes; Clostridia_SP; Clostridiales_CL; Clostridiales; *Faecalibacterium*_FM; sfA; 37567; AY981009.1 gg_id: 119750 human rectum mucosal biopsy clone V165 |
| human waste | 37578 | Bacteria; Firmicutes; Clostridia_SP; Clostridiales_CL; Clostridiales; *Faecalibacterium*_FM; sfA; 37578; AY980282.1 gg_id: 127197 human rectum mucosal biopsy clone MX75 |
| human waste | 37584 | Bacteria; Firmicutes; Clostridia_SP; Clostridiales_CL; Clostridiales; *Faecalibacterium*_FM; sfA; 37584; AY986127.1 gg_id: 116066 human stool clone D470 |
| human waste | 37591 | Bacteria; Firmicutes; Clostridia_SP; Clostridiales_CL; Clostridiales; *Faecalibacterium*_FM; sfA; 37591; DQ802430.1 gg_id: 174750 human fecal clone RL188_aah17f04 |
| human waste | 37596 | Bacteria; Firmicutes; Clostridia_SP; Clostridiales_CL; Clostridiales; *Faecalibacterium*_FM; sfA; 37596; EF401310.1 gg_id: 207901 human fecal clone SJTU_D_08_63 |
| human waste | 37601 | Bacteria; Firmicutes; Clostridia_SP; Clostridiales_CL; Clostridiales; *Faecalibacterium*_FM; sfA; 37601; AM697227.1 gg_id: 223980 sequencing libraries indoor dust clone BF0001C068 |
| human waste | 37608 | Bacteria; Firmicutes; Clostridia_SP; Clostridiales_CL; Clostridiales; *Faecalibacterium*_FM; sfA; 37608; DQ801706.1 gg_id: 177293 human fecal clone RL201_aai45g09 |
| human waste | 37619 | Bacteria; Firmicutes; Clostridia_SP; Clostridiales_CL; Clostridiales; *Faecalibacterium*_FM; sfA; 37619; EF405024.1 gg_id: 206629 human fecal clone SJTU_G_07_03 |
| human waste | 37639 | Bacteria; Firmicutes; Clostridia_SP; Clostridiales_CL; Clostridiales; *Faecalibacterium*_FM; sfA; 37639; DQ801869.1 gg_id: 191704 human fecal clone RL201_aai47h03 |
| human waste | 37650 | Bacteria; Firmicutes; Clostridia_SP; Clostridiales_CL; Clostridiales; *Faecalibacterium*_FM; sfA; 37650; DQ808616.1 gg_id: 174395 human fecal clone RL239_aaj11a04 |
| human waste | 37654 | Bacteria; Firmicutes; Clostridia_SP; Clostridiales_CL; Clostridiales; *Faecalibacterium*_FM; sfA; 37654; AY979276.1 gg_id: 123222 human transverse colon mucosal biopsy clone Z478 |
| human waste | 37655 | Bacteria; Firmicutes; Clostridia_SP; Clostridiales_CL; Clostridiales; *Faecalibacterium*_FM; sfA; 37655; DQ801708.1 gg_id: 190945 human fecal clone RL201_aai45g11 |
| human waste | 37668 | Bacteria; Firmicutes; Clostridia_SP; Clostridiales_CL; Clostridiales; *Faecalibacterium*_FM; sfA; 37668; AY978645.1 gg_id: 122335 human transverse colon mucosal biopsy clone KS69 |
| human waste | 37670 | Bacteria; Firmicutes; Clostridia_SP; Clostridiales_CL; Clostridiales; *Faecalibacterium*_FM; sfA; 37670; AY981791.1 gg_id: 127448 human sigmoid colon mucosal biopsy clone NT62 |

TABLE 3-continued

Sewage ID taxa
HUMAN WASTE IDENTIFIER TAXA

| Source | #OTU ID | Lineage for representative OTU |
|---|---|---|
| human waste | 37681 | Bacteria; Firmicutes; Clostridia_SP; Clostridiales_CL; Clostridiales; *Faecalibacterium*_FM; sfA; 37681; AY984534.1 gg_id: 121004 human stool clone B467 |
| human waste | 37685 | Bacteria; Firmicutes; Clostridia_SP; Clostridiales_CL; Clostridiales; *Faecalibacterium*_FM; sfA; 37685; DQ325575.1 gg_id: 148122 Metagenomic gut microbiome healthy human stool clone B071 |
| human waste | 37688 | Bacteria; Firmicutes; Clostridia_SP; Clostridiales_CL; Clostridiales; *Faecalibacterium*_FM; sfA; 37688; DQ798226.1 gg_id: 199642 human fecal clone RL181__aah39b04 |
| human waste | 37704 | Bacteria; Firmicutes; Clostridia_SP; Clostridiales_CL; Clostridiales; *Faecalibacterium*_FM; sfA; 37704; DQ806635.1 gg_id: 187676 human fecal clone RL186__aao47a06 |
| human waste | 37724 | Bacteria; Firmicutes; Clostridia_SP; Clostridiales_CL; Clostridiales; *Faecalibacterium*_FM; sfA; 37724; EF403312.1 gg_id: 209893 human fecal clone SJTU_A1_2_38 |
| human waste | 37742 | Bacteria; Firmicutes; Clostridia_SP; Clostridiales_CL; Clostridiales; *Faecalibacterium*_FM; sfA; 37742; DQ904859.1 gg_id: 165658 human fecal clone 001C-d10 |
| human waste | 37743 | Bacteria; Firmicutes; Clostridia_SP; Clostridiales_CL; Clostridiales; *Faecalibacterium*_FM; sfA; 37743; DQ797247.1 gg_id: 192544 human fecal clone RL386__aao88h06 |
| human waste | 37752 | Bacteria; Firmicutes; Clostridia_SP; Clostridiales_CL; Clostridiales; *Faecalibacterium*_FM; sfA; 37752; AY982943.1 gg_id: 120284 human descending colon mucosal biopsy clone L145 |
| human waste | 37753 | Bacteria; Firmicutes; Clostridia_SP; Clostridiales_CL; Clostridiales; *Faecalibacterium*_FM; sfA; 37753; DQ795972.1 gg_id: 184212 human fecal clone RL202__aai49f09 |
| human waste | 37756 | Bacteria; Firmicutes; Clostridia_SP; Clostridiales_CL; Clostridiales; *Faecalibacterium*_FM; sfA; 37756; AY982114.1 gg_id: 123756 human sigmoid colon mucosal biopsy clone P656 |
| human waste | 37760 | Bacteria; Firmicutes; Clostridia_SP; Clostridiales_CL; Clostridiales; *Faecalibacterium*_FM; sfA; 37760; DQ801384.1 gg_id: 178047 human fecal clone RL388__aao94g07 |
| human waste | 37762 | Bacteria; Firmicutes; Clostridia_SP; Clostridiales_CL; Clostridiales; *Faecalibacterium*_FM; sfA; 37762; DQ808878.1 gg_id: 177209 human fecal clone RL243__aai86e05 |
| human waste | 37764 | Bacteria; Firmicutes; Clostridia_SP; Clostridiales_CL; Clostridiales; *Faecalibacterium*_FM; sfA; 37764; AY978991.1 gg_id: 119889 human transverse colon mucosal biopsy clone NI22 |
| human waste | 37804 | Bacteria; Firmicutes; Clostridia_SP; Clostridiales_CL; Clostridiales; *Faecalibacterium*_FM; sfA; 37804; EF402060.1 gg_id: 216252 human fecal clone SJTU_B_03_07 |
| human waste | 37816 | Bacteria; Firmicutes; Clostridia_SP; Clostridiales_CL; Clostridiales; *Faecalibacterium*_FM; sfA; 37816; DQ802670.1 gg_id: 184779 human fecal clone RL188__aan95a02 |
| human waste | 37823 | Bacteria; Firmicutes; Clostridia_SP; Clostridiales_CL; Clostridiales; *Faecalibacterium*_FM; sfA; 37823; DQ795974.1 gg_id: 198529 human fecal clone RL202__aai49f11 |
| human waste | 37824 | Bacteria; Firmicutes; Clostridia_SP; Clostridiales_CL; Clostridiales; *Faecalibacterium*_FM; sfA; 37824; EF401777.1 gg_id: 214458 human fecal clone SJTU_D_15_22 |
| human waste | 37826 | Bacteria; Firmicutes; Clostridia_SP; Clostridiales_CL; Clostridiales; *Faecalibacterium*_FM; sfA; 37826; AY978231.1 gg_id: 119111 human transverse colon mucosal biopsy clone F042 |
| human waste | 37835 | Bacteria; Firmicutes; Clostridia_SP; Clostridiales_CL; Clostridiales; *Faecalibacterium*_FM; sfA; 37835; DQ806034.1 gg_id: 180870 human fecal clone RL186__aah60c02 |
| human waste | 37838 | Bacteria; Firmicutes; Clostridia_SP; Clostridiales_CL; Clostridiales; *Faecalibacterium*_FM; sfA; 37838; EF403746.1 gg_id: 208266 human fecal clone SJTU_A2_06_74 |
| human waste | 37840 | Bacteria; Firmicutes; Clostridia_SP; Clostridiales_CL; Clostridiales; *Faecalibacterium*_FM; sfA; 37840; DQ797519.1 gg_id: 191286 human fecal clone RL248__aaj00d12 |
| human waste | 37875 | Bacteria; Firmicutes; Clostridia_SP; Clostridiales_CL; Clostridiales; *Faecalibacterium*_FM; sfA; 37875; DQ800105.1 gg_id: 199166 human fecal clone RL247__aaj24c02 |
| human waste | 37882 | Bacteria; Firmicutes; Clostridia_SP; Clostridiales_CL; Clostridiales; *Faecalibacterium*_FM; sfA; 37882; EF401102.1 gg_id: 206251 human fecal clone SJTU_D_05_76 |
| human waste | 37907 | Bacteria; Firmicutes; Clostridia_SP; Clostridiales_CL; Clostridiales; *Faecalibacterium*_FM; sfA; 37907; DQ799947.1 gg_id: 190321 human fecal clone RL247__aaj22b10 |
| human waste | 37913 | Bacteria; Firmicutes; Clostridia_SP; Clostridiales_CL; Clostridiales; *Faecalibacterium*_FM; sfA; 37913; DQ825062.1 gg_id: 190667 human fecal clone RL185__aao72h05 |
| human waste | 37915 | Bacteria; Firmicutes; Clostridia_SP; Clostridiales_CL; Clostridiales; *Faecalibacterium*_FM; sfA; 37915; AY982115.1 gg_id: 122737 human sigmoid colon mucosal biopsy clone P657 |
| human waste | 37917 | Bacteria; Firmicutes; Clostridia_SP; Clostridiales_CL; Clostridiales; *Faecalibacterium*_FM; sfA; 37917; AY979738.1 gg_id: 116513 human transverse colon mucosal biopsy clone M483 |
| human waste | 37919 | Bacteria; Firmicutes; Clostridia_SP; Clostridiales_CL; Clostridiales; *Faecalibacterium*_FM; sfA; 37919; AY979173.1 gg_id: 116135 human transverse colon mucosal biopsy clone Z246 |
| human waste | 37926 | Bacteria; Firmicutes; Clostridia_SP; Clostridiales_CL; Clostridiales; *Faecalibacterium*_FM; sfA; 37926; EF402454.1 gg_id: 203687 human fecal clone SJTU_B_08_14 |
| human waste | 37932 | Bacteria; Firmicutes; Clostridia_SP; Clostridiales_CL; Clostridiales; *Faecalibacterium*_FM; sfA; 37932; AY916280.1 gg_id: 113700 human sigmoid colon biopsy clone L420 |
| human waste | 37936 | Bacteria; Firmicutes; Clostridia_SP; Clostridiales_CL; Clostridiales; *Faecalibacterium*_FM; sfA; 37936; DQ802745.1 gg_id: 187818 human fecal clone RL188__aan96a10 |
| human waste | 37943 | Bacteria; Firmicutes; Clostridia_SP; Clostridiales_CL; Clostridiales; *Faecalibacterium*_FM; sfA; 37943; DQ799945.1 gg_id: 177133 human fecal clone RL247__aaj22b08 |
| human waste | 37949 | Bacteria; Firmicutes; Clostridia_SP; Clostridiales_CL; Clostridiales; *Faecalibacterium*_FM; sfA; 37949; AY978657.1 gg_id: 116927 human transverse colon mucosal biopsy clone KS92 |
| human waste | 37961 | Bacteria; Firmicutes; Clostridia_SP; Clostridiales_CL; Clostridiales; *Faecalibacterium*_FM; sfA; 37961; EF404298.1 gg_id: 206212 human fecal clone SJTU_C_08_07 |
| human waste | 37967 | Bacteria; Firmicutes; Clostridia_SP; Clostridiales_CL; Clostridiales; *Faecalibacterium*_FM; sfA; 37967; DQ802424.1 gg_id: 179590 human fecal clone RL188__aah17e08 |
| human waste | 37980 | Bacteria; Firmicutes; Clostridia_SP; Clostridiales_CL; Clostridiales; *Faecalibacterium*_FM; sfA; 37980; AY978591.1 gg_id: 125363 human transverse colon mucosal biopsy clone KR74 |
| human waste | 37983 | Bacteria; Firmicutes; Clostridia_SP; Clostridiales_CL; Clostridiales; *Faecalibacterium*_FM; sfA; 37983; DQ805895.1 gg_id: 197061 human fecal clone RL306aal92d05 |

TABLE 3-continued

Sewage ID taxa
HUMAN WASTE IDENTIFIER TAXA

| Source | #OTU ID | Lineage for representative OTU |
|---|---|---|
| human waste | 37984 | Bacteria; Firmicutes; Clostridia_SP; Clostridiales_CL; Clostridiales; *Faecalibacterium*_FM; sfA; 37984; DQ807398.1 gg_id: 198896 human fecal clone RL307__aam06a09 |
| human waste | 37991 | Bacteria; Firmicutes; Clostridia_SP; Clostridiales_CL; Clostridiales; *Faecalibacterium*_FM; sfA; 37991; DQ806247.1 gg_id: 187365 human fecal clone RL186__aan89c07 |
| human waste | 43113 | Bacteria; Firmicutes; Clostridia_SP; Clostridiales_CL; Clostridiales; *Faecalibacterium*_FM; sfA; 43113; DQ795067.1 gg_id: 194436 human fecal clone RL310__aam39g07 |
| human waste | 43195 | Bacteria; Firmicutes; Clostridia_SP; Clostridiales_CL; Clostridiales; *Faecalibacterium*_FM; sfA; 43195; DQ795243.1 gg_id: 192438 human fecal clone RL178__aah51h08 |
| human waste | 43210 | Bacteria; Firmicutes; Clostridia_SP; Clostridiales_CL; Clostridiales; *Faecalibacterium*_FM; sfA; 43210; DQ808308.1 gg_id: 199463 human fecal clone RL180__aao75b02 |
| human waste | 43431 | Bacteria; Firmicutes; Clostridia_SP; Clostridiales_CL; Clostridiales; *Faecalibacterium*_FM; sfA; 43431; DQ809307.1 gg_id: 179920 human fecal clone RL184__aah19a07 |
| human waste | 43514 | Bacteria; Firmicutes; Clostridia_SP; Clostridiales_CL; Clostridiales; *Faecalibacterium*_FM; sfA; 43514; DQ797951.1 gg_id: 188897 human fecal clone RL302__aal93g08 |
| human waste | 43909 | Bacteria; Firmicutes; Clostridia_SP; Clostridiales_CL; Clostridiales; *Faecalibacterium*_FM; sfA; 43909; DQ796681.1 gg_id: 180456 human fecal clone RL179__aao53b03 |
| human waste | 43917 | Bacteria; Firmicutes; Clostridia_SP; Clostridiales_CL; Clostridiales; *Faecalibacterium*_FM; sfA; 43917; DQ793911.1 gg_id: 181445 human fecal clone RL176__aah45b11 |
| human waste | 43926 | Bacteria; Firmicutes; Clostridia_SP; Clostridiales_CL; Clostridiales; *Faecalibacterium*_FM; sfA; 43926; DQ798699.1 gg_id: 178357 human fecal clone RL181__aao00c06 |
| human waste | 43930 | Bacteria; Firmicutes; Clostridia_SP; Clostridiales_CL; Clostridiales; *Faecalibacterium*_FM; sfA; 43930; DQ825099.1 gg_id: 174304 human fecal clone RL185__aan85d04 |
| human waste | 1324 | Bacteria; Firmicutes; Clostridia_SP; Clostridiales_CL; Clostridiales; *Ruminococcus*_FM; sfA; 1324; DQ798187.1 gg_id: 183397 human fecal clone RL302__aal96f02 |
| human waste | 1858 | Bacteria; Firmicutes; Clostridia_SP; Clostridiales_CL; Clostridiales; *Ruminococcus*_FM; sfA; 1858; DQ808570.1 gg_id: 175884 human fecal clone RL239__aaj10c07 |
| human waste | 4734 | Bacteria; Firmicutes; Clostridia_SP; Clostridiales_CL; Clostridiales; *Ruminococcus*_FM; sfA; 4734; DQ905428.1 gg_id: 170323 human fecal clone 013C-F1 |
| human waste | 4744 | Bacteria; Firmicutes; Clostridia_SP; Clostridiales_CL; Clostridiales; *Ruminococcus*_FM; sfA; 4744; DQ326405.1 gg_id: 146044 Metagenomic gut microbiome healthy human stool clone C447 |
| human waste | 4783 | Bacteria; Firmicutes; Clostridia_SP; Clostridiales_CL; Clostridiales; *Ruminococcus*_FM; sfA; 4783; DQ803575.1 gg_id: 199520 human fecal clone RL251__aaj87f06 |
| human waste | 4806 | Bacteria; Firmicutes; Clostridia_SP; Clostridiales_CL; Clostridiales; *Ruminococcus*_FM; sfA; 4806; AY452001.1 gg_id: 105123 human intestine clone Muc3-5 |
| human waste | 4815 | Bacteria; Firmicutes; Clostridia_SP; Clostridiales_CL; Clostridiales; *Ruminococcus*_FM; sfA; 4815; DQ799750.1 gg_id: 193888 human fecal clone RL182__aah32f11 |
| human waste | 4870 | Bacteria; Firmicutes; Clostridia_SP; Clostridiales_CL; Clostridiales; *Ruminococcus*_FM; sfA; 4870; DQ808004.1 gg_id: 190938 human fecal clone RL180__aan70e07 |
| human waste | 4903 | Bacteria; Firmicutes; Clostridia_SP; Clostridiales_CL; Clostridiales; *Ruminococcus*_FM; sfA; 4903; DQ905036.1 gg_id: 164309 human fecal clone 2-002-c6 |
| human waste | 4939 | Bacteria; Firmicutes; Clostridia_SP; Clostridiales_CL; Clostridiales; *Ruminococcus*_FM; sfA; 4939; DQ804290.1 gg_id: 174577 human fecal clone RL187__aan77e07 |
| human waste | 4949 | Bacteria; Firmicutes; Clostridia_SP; Clostridiales_CL; Clostridiales; *Ruminococcus*_FM; sfA; 4949; DQ807789.1 gg_id: 183570 human fecal clone RL180__aah37c01 |
| human waste | 5007 | Bacteria; Firmicutes; Clostridia_SP; Clostridiales_CL; Clostridiales; *Ruminococcus*_FM; sfA; 5007; DQ803611.1 gg_id: 196630 human fecal clone RL251__aaj88b09 |
| human waste | 5051 | Bacteria; Firmicutes; Clostridia_SP; Clostridiales_CL; Clostridiales; *Ruminococcus*_FM; sfA; 5051; DQ808470.1 gg_id: 180780 human fecal clone RL180__aao76h09 |
| human waste | 5057 | Bacteria; Firmicutes; Clostridia_SP; Clostridiales_CL; Clostridiales; *Ruminococcus*_FM; sfA; 5057; DQ802786.1 gg_id: 198067 human fecal clone RL188__aan96e08 |
| human waste | 5125 | Bacteria; Firmicutes; Clostridia_SP; Clostridiales_CL; Clostridiales; *Ruminococcus*_FM; sfA; 5125; AJ608235.1 gg_id: 145710 human biopsies ulcerative colitis biopsy clone UC7-23 |
| human waste | 5137 | Bacteria; Firmicutes; Clostridia_SP; Clostridiales_CL; Clostridiales; *Ruminococcus*_FM; sfA; 5137; DQ799752.1 gg_id: 185278 human fecal clone RL182__aah32g05 |
| human waste | 5160 | Bacteria; Firmicutes; Clostridia_SP; Clostridiales_CL; Clostridiales; *Ruminococcus*_FM; sfA; 5160; DQ824917.1 gg_id: 175356 human fecal clone RL185__aao71a01 |
| human waste | 5235 | Bacteria; Firmicutes; Clostridia_SP; Clostridiales_CL; Clostridiales; *Ruminococcus*_FM; sfA; 5235; DQ802364.1 gg_id: 195286 human fecal clone RL188__aah16f09 |
| human waste | 5270 | Bacteria; Firmicutes; Clostridia_SP; Clostridiales_CL; Clostridiales; *Ruminococcus*_FM; sfA; 5270; DQ805200.1 gg_id: 196479 human fecal clone RL249__aaj82h08 |
| human waste | 5312 | Bacteria; Firmicutes; Clostridia_SP; Clostridiales_CL; Clostridiales; *Ruminococcus*_FM; sfA; 5312; AY169419.1 gg_id: 81272 *Ruminococcus obeum* |
| human waste | 5318 | Bacteria; Firmicutes; Clostridia_SP; Clostridiales_CL; Clostridiales; *Ruminococcus*_FM; sfA; 5318; DQ803454.1 gg_id: 181264 human fecal clone RL251__aaj86a05 |
| human waste | 5369 | Bacteria; Firmicutes; Clostridia_SP; Clostridiales_CL; Clostridiales; *Ruminococcus*_FM; sfA; 5369; DQ806583.1 gg_id: 194217 human fecal clone RL186__aao46d03 |
| human waste | 5417 | Bacteria; Firmicutes; Clostridia_SP; Clostridiales_CL; Clostridiales; *Ruminococcus*_FM; sfA; 5417; AF357566.1 gg_id: 35844 mpn-isolate group 18 |
| human waste | 5463 | Bacteria; Firmicutes; Clostridia_SP; Clostridiales_CL; Clostridiales; *Ruminococcus*_FM; sfA; 5463; DQ326616.1 gg_id: 146405 Metagenomic gut microbiome healthy human stool clone E050 |
| human waste | 5479 | Bacteria; Firmicutes; Clostridia_SP; Clostridiales_CL; Clostridiales; *Ruminococcus*_FM; sfA; 5479; EF402618.1 gg_id: 216770 human fecal clone SJTU_B_10_28 |
| human waste | 5535 | Bacteria; Firmicutes; Clostridia_SP; Clostridiales_CL; Clostridiales; *Ruminococcus*_FM; sfA; 5535; DQ804574.1 gg_id: 179011 human fecal clone RL187__aao69h01 |

TABLE 3-continued

Sewage ID taxa
HUMAN WASTE IDENTIFIER TAXA

| Source | #OTU ID | Lineage for representative OTU |
|---|---|---|
| human waste | 5566 | Bacteria; Firmicutes; Clostridia_SP; Clostridiales_CL; Clostridiales; *Ruminococcus*_FM; sfA; 5566; EF401853.1 gg_id: 214669 human fecal clone SJTU_D_11_96 |
| human waste | 5585 | Bacteria; Firmicutes; Clostridia_SP; Clostridiales_CL; Clostridiales; *Ruminococcus*_FM; sfA; 5585; DQ809653.1 gg_id: 197346 human fecal clone RL184_aan82b09 |
| human waste | 5667 | Bacteria; Firmicutes; Clostridia_SP; Clostridiales_CL; Clostridiales; *Ruminococcus*_FM; sfA; 5667; DQ803204.1 gg_id: 191545 human fecal clone RL311_aam22b01 |
| human waste | 5680 | Bacteria; Firmicutes; Clostridia_SP; Clostridiales_CL; Clostridiales; *Ruminococcus*_FM; sfA; 5680; DQ794432.1 gg_id: 182448 human fecal clone RL197_aah87f08 |
| human waste | 5689 | Bacteria; Firmicutes; Clostridia_SP; Clostridiales_CL; Clostridiales; *Ruminococcus*_FM; sfA; 5689; DQ805925.1 gg_id: 185257 human fecal clone RL306aal92g02 |
| human waste | 5714 | Bacteria; Firmicutes; Clostridia_SP; Clostridiales_CL; Clostridiales; *Ruminococcus*_FM; sfA; 5714; DQ799789.1 gg_id: 180169 human fecal clone RL182_aah33f04 |
| human waste | 5732 | Bacteria; Firmicutes; Clostridia_SP; Clostridiales_CL; Clostridiales; *Ruminococcus*_FM; sfA; 5732; DQ803268.1 gg_id: 194134 human fecal clone RL311_aam23b10 |
| human waste | 5749 | Bacteria; Firmicutes; Clostridia_SP; Clostridiales_CL; Clostridiales; *Ruminococcus*_FM; sfA; 5749; DQ801386.1 gg_id: 179329 human fecal clone RL388_aao94g09 |
| human waste | 5776 | Bacteria; Firmicutes; Clostridia_SP; Clostridiales_CL; Clostridiales; *Ruminococcus*_FM; sfA; 5776; DQ905045.1 gg_id: 165102 human fecal clone 2-002-d3 |
| human waste | 5805 | Bacteria; Firmicutes; Clostridia_SP; Clostridiales_CL; Clostridiales; *Ruminococcus*_FM; sfA; 5805; DQ794571.1 gg_id: 192840 human fecal clone RL240_aaj29g04 |
| human waste | 5811 | Bacteria; Firmicutes; Clostridia_SP; Clostridiales_CL; Clostridiales; *Ruminococcus*_FM; sfA; 5811; DQ802111.1 gg_id: 187122 human fecal clone RL241_aaj03c01 |
| human waste | 5869 | Bacteria; Firmicutes; Clostridia_SP; Clostridiales_CL; Clostridiales; *Ruminococcus*_FM; sfA; 5869; DQ327066.1 gg_id: 147105 Metagenomic gut microbiome healthy human stool clone E574 |
| human waste | 6182 | Bacteria; Firmicutes; Clostridia_SP; Clostridiales_CL; Clostridiales; Unclassified; sfA; 6182; DQ804553.1 gg_id: 188288 human fecal clone RL187_aao69f02 |
| human waste | 6795 | Bacteria; Firmicutes; Clostridia_SP; Clostridiales_CL; Clostridiales; Unclassified; sfA; 6795; DQ808276.1 gg_id: 174107 human fecal clone RL180_aao74f10 |
| human waste | 35253 | Bacteria; Firmicutes; Clostridia_SP; Clostridiales_CL; Clostridiales; Unclassified; sfB; 35253; EU475232.1 gg_id: 300467 Evolution mammals and their gut microbes bonobo feces clone BNO_aaa01e07 |
| human waste | 41888 | Bacteria; Firmicutes; Clostridia_SP; Peptostreptococcaceae_CL; Peptostreptococcaceae_OR; Peptostreptococcaceae; sfA; 41888; AF371681.1 gg_id: 36226 swine intestine clone p-3263-42A2 |
| human waste | 1743 | Bacteria; Firmicutes; Clostridia_SP; RL197_aah88c10_CL; Clostridiales; Unclassified; sfA; 1743; DQ799671.1 gg_id: 186824 human fecal clone RL305aal88h09 |
| human waste | 42161 | Bacteria; Firmicutes; Clostridia_SP; SHA-32_CL; Unclassified; Unclassified; sfB; 42161; EU234161.1 gg_id: 246299 receiving river and un techniques effluent WWTP treating penicillin G production wastewater clone B11 |
| human waste | 42628 | Bacteria; Firmicutes; Clostridia_SP; SHA-32_CL; Unclassified; Unclassified; sfB; 42628; AY953192.1 gg_id: 114782 anaerobic swine lagoon clone A-2AD |
| human waste | 42417 | Bacteria; Firmicutes; Mollicutes_SP; *Catenibacterium*_CL; *Catenibacterium*_OR; *Catenibacterium*_FM; sfA; 42417; DQ801161.1 gg_id: 176710 human fecal clone RL116_aae99d07 |
| human waste | 51239 | Bacteria; Proteobacteria; Deltaproteobacteria_SP; Desulfobacteraceae_CL; Desulfobacteraceae_OR; Desulfobacteraceae; sfA; 51239; EF077225.1 gg_id: 250773 Anaerobic oxidation short-chain hydrocarbons marine sulphate-reducing Guaymas Basin hydrothermal sediment isolate BuS5BuS5 str. BuS5 |
| human waste | 51195 | Bacteria; Proteobacteria; Deltaproteobacteria_SP; *Desulfobacterium*_CL; *Desulfobacterium*_OR; *Desulfobacterium*_FM; sfB; 51195; AJ535237.1 gg_id: 77760 marine sediment above hydrate ridge clone Hyd01-n proteobacterium |
| human waste | 51859 | Bacteria; Proteobacteria; Deltaproteobacteria_SP; *Desulfobacterium*_CL; *Desulfobacterium*_OR; *Desulfobacterium*_FM; sfB; 51859; AJ012591.1 gg_id: 10788 related to *Desulfobulbus* |
| human waste | 51977 | Bacteria; Proteobacteria; Deltaproteobacteria_SP; *Desulfobacterium*_CL; *Desulfobacterium*_OR; *Desulfobacterium*_FM; sfB; 51977; AY548789.1 gg_id: 105497 *Desulfobulbus propionicus* str. DSM 2032 |
| human waste | 51929 | Bacteria; Proteobacteria; Deltaproteobacteria_SP; *Geobacter*_CL; *Geobacter*_OR; *Geobacter*_FM; sfA; 51929; DQ383306.1 gg_id: 201387 biofilm phototrophic biological sulfide-removal reactor photobioreactor clone 16/3-164 |
| human waste | 51264 | Bacteria; Proteobacteria; Desulfovibrionales_SP; Desulfovibrionales_CL; Desulfovibrionales; Desulfovibrionaceae; sfB; 51264; EU234117.1 gg_id: 236749 receiving river and un techniques anaerobic process WWTP treating penicillin G production wastewater clone A34 |
| human waste | 51390 | Bacteria; Proteobacteria; Desulfovibrionales_SP; Desulfovibrionales_CL; Desulfovibrionales; Desulfovibrionaceae; sfB; 51390; Y12254.1 gg_id: 10519 *Desulfovibrio intestinalis* str. KMS2 |
| human waste | 51965 | Bacteria; Proteobacteria; Desulfovibrionales_SP; Desulfovibrionales_CL; Desulfovibrionales; Desulfovibrionaceae; sfB; 51965; M34113.1 gg_id: 10515 *Desulfovibrio desulfuricans* |
| human waste | 58942 | Bacteria; Proteobacteria; Epsilonproteobacteria_SP; Arcobacteraceae_CL; Arcobacteraceae_OR; Arcobacteraceae; sfA; 58942; AF235116.1 gg_id: 49628 North Sea clone KTc1160 |
| human waste | 58964 | Bacteria; Proteobacteria; Epsilonproteobacteria_SP; Arcobacteraceae_CL; Arcobacteraceae_OR; Arcobacteraceae; sfA; 58964; EF515620.1 gg_id: 219360 Electricigen Enrichment MFC full-scale anaerobic bioreactor sludge treating brewery waste clone 31b04 |
| human waste | 59327 | Bacteria; Proteobacteria; Epsilonproteobacteria_SP; Arcobacteraceae_CL; Arcobacteraceae_OR; Arcobacteraceae; sfA; 59327; AY704399.1 gg_id: 111400 oceanic crust clone FS118-51B-02 |
| human waste | 58850 | Bacteria; Proteobacteria; Epsilonproteobacteria_SP; Sulfurospirillaceae_CL; Sulfurospirillaceae_OR; Sulfurospirillaceae; sfA; 58850; AB186804.1 gg_id: 100941 polychlorinated dioxin dechlorinating microcosm clone TSAC01 |
| human waste | 19451 | Bacteria; Proteobacteria; Gammaproteobacteria_SP; Aeromonadaceae_CL; Aeromonadaceae_OR; Aeromonadaceae; sfA; 19451; AB105442.1 gg_id: 82407 Batch reactor filled with cyanobacterial bloom and lake water clone-8 |
| human waste | 29710 | Bacteria; Proteobacteria; Gammaproteobacteria_SP; Betaproteobacteria_CL; Comamonadaceae_OR; Comamonadaceae; sfA; 29710; AY947938.1 gg_id: 141400 Synchrony and seasonality two temperate rivers USA: Massachusetts Ipswich River clone IRD18D12 |

TABLE 3-continued

Sewage ID taxa
HUMAN WASTE IDENTIFIER TAXA

| Source | #OTU ID | Lineage for representative OTU |
|---|---|---|
| human waste | 29735 | Bacteria; Proteobacteria; Gammaproteobacteria_SP; Betaproteobacteria_CL; Comamonadaceae_OR; Comamonadaceae; sfA; 29735; AF078757.1 gg_id: 7096 *Aquaspirillum metamorphum* str. LMG 4339 |
| human waste | 29748 | Bacteria; Proteobacteria; Gammaproteobacteria_SP; Betaproteobacteria_CL; Comamonadaceae_OR; Comamonadaceae; sfA; 29748; AY853671.1 gg_id: 109658 napthalene-contaminated soil clone 27 |
| human waste | 29770 | Bacteria; Proteobacteria; Gammaproteobacteria_SP; Betaproteobacteria_CL; Comamonadaceae_OR; Comamonadaceae; sfA; 29770; AB166889.1 gg_id: 105361 *Hydrogenophaga* sp. str. TRS-05 |
| human waste | 29774 | Bacteria; Proteobacteria; Gammaproteobacteria_SP; Betaproteobacteria_CL; Comamonadaceae_OR; Comamonadaceae; sfA; 29774; AY684785.1 gg_id: 103473 *Delftia tsuruhatensis* str. ARI_5 |
| human waste | 29878 | Bacteria; Proteobacteria; Gammaproteobacteria_SP; Betaproteobacteria_CL; Comamonadaceae_OR; Comamonadaceae; sfA; 29878; AF078755.1 gg_id: 7088 *Aquaspirillum psychrophilum* str. LMG 5408 |
| human waste | 29908 | Bacteria; Proteobacteria; Gammaproteobacteria_SP; Betaproteobacteria_CL; Comamonadaceae_OR; Comamonadaceae; sfA; 29908; AB240488.1 gg_id: 142529 microbial structure rhizosphere biofilm Sapporo root-tip (0 40 mm) Phragmites Sosei River Sappro Japan clone SRRT59 |
| human waste | 29969 | Bacteria; Proteobacteria; Gammaproteobacteria_SP; Betaproteobacteria_CL; Comamonadaceae_OR; Comamonadaceae; sfA; 29969; EF516688.1 gg_id: 217926 grassland soil clone FCPS548 |
| human waste | 30081 | Bacteria; Proteobacteria; Gammaproteobacteria_SP; Betaproteobacteria_CL; Comamonadaceae_OR; Comamonadaceae; sfA; 30081; AY212666.1 gg_id: 100099 water 20 m downstream manure clone 219ds20 |
| human waste | 30124 | Bacteria; Proteobacteria; Gammaproteobacteria_SP; Betaproteobacteria_CL; Comamonadaceae_OR; Comamonadaceae; sfA; 30124; EF015884.1 gg_id: 181878 *Comamonas compostus* str. CC-YY287 |
| human waste | 30138 | Bacteria; Proteobacteria; Gammaproteobacteria_SP; Betaproteobacteria_CL; Comamonadaceae_OR; Comamonadaceae; sfA; 30138; AJ422174.2 gg_id: 23589 Germany: Spittelwasser River clone Spb283 |
| human waste | 30155 | Bacteria; Proteobacteria; Gammaproteobacteria_SP; Betaproteobacteria_CL; Comamonadaceae_OR; Comamonadaceae; sfA; 30155; AY212680.1 gg_id: 100363 water 5 m downstream manure clone 233ds5 |
| human waste | 30246 | Bacteria; Proteobacteria; Gammaproteobacteria_SP; Betaproteobacteria_CL; Comamonadaceae_OR; Comamonadaceae; sfA; 30246; AB195170.1 gg_id: 108781 *Diaphorobacter* sp. str. PD-12 |
| human waste | 30339 | Bacteria; Proteobacteria; Gammaproteobacteria_SP; Betaproteobacteria_CL; Comamonadaceae_OR; Comamonadaceae; sfA; 30339; EU535832.1 gg_id: 280023 profile human microbiota antecubital fossa (inner elbow) skin clone nbt05a08 |
| human waste | 30399 | Bacteria; Proteobacteria; Gammaproteobacteria_SP; Betaproteobacteria_CL; Comamonadaceae_OR; Comamonadaceae; sfA; 30399; AF422643.1 gg_id: 35695 TCE-sediment clone d034 |
| human waste | 30476 | Bacteria; Proteobacteria; Gammaproteobacteria_SP; Betaproteobacteria_CL; Comamonadaceae_OR; Comamonadaceae; sfA; 30476; AY212684.1 gg_id: 100988 water 5 m downstream manure clone 237ds5 |
| human waste | 30568 | Bacteria; Proteobacteria; Gammaproteobacteria_SP; Betaproteobacteria_CL; Comamonadaceae_OR; Comamonadaceae; sfA; 30568; DQ640723.1 gg_id: 227889 full-scale EBPR sludge clone Skagen135 |
| human waste | 21369 | Bacteria; Proteobacteria; Gammaproteobacteria_SP; Betaproteobacteria_CL; MND1_OR; Unclassified; sfA; 21369; DQ230970.1 gg_id: 143170 subsurface water clone DR938CH110701SACH93 |
| human waste | 22096 | Bacteria; Proteobacteria; Gammaproteobacteria_SP; Betaproteobacteria_CL; Neisseriales; *Laribacter*_FM; sfA; 22096; AF389085.1 gg_id: 16445 *Laribacter hongkongensis* str. HKU1 |
| human waste | 33736 | Bacteria; Proteobacteria; Gammaproteobacteria_SP; Moraxellaceae_CL; Moraxellaceae_OR; Moraxellaceae; sfA; 33736; EU010147.1 gg_id: 247825 Biogeography Singapore seawaters seawater clone B68 |
| human waste | 23727 | Bacteria; Proteobacteria; Gammaproteobacteria_SP; Pseudomonadaceae_CL; Pseudomonadaceae_OR; Pseudomonadaceae; sfA; 23727; AY054374.1 gg_id: 105822 *Pseudomonas pavonaceae* |
| human waste | 23960 | Bacteria; Proteobacteria; Gammaproteobacteria_SP; Pseudomonadaceae_CL; Pseudomonadaceae_OR; Pseudomonadaceae; sfA; 23960; AY959184.1 gg_id: 130757 Microbes on human vaginal epithelium clone rRNA411 |
| human waste | 24730 | Bacteria; Proteobacteria; Gammaproteobacteria_SP; Pseudomonadaceae_CL; Pseudomonadaceae_OR; Pseudomonadaceae; sfA; 24730; EF623836.1 gg_id: 245159 *Pseudomonas putida* str. GIST-MRP44-1 |
| human waste | 24762 | Bacteria; Proteobacteria; Gammaproteobacteria_SP; Pseudomonadaceae_CL; Pseudomonadaceae_OR; Pseudomonadaceae; sfA; 24762; AY959151.1 gg_id: 137031 Microbes on human vaginal epithelium clone rRNA378 |
| human waste | 24842 | Bacteria; Proteobacteria; Gammaproteobacteria_SP; Pseudomonadaceae_CL; Pseudomonadaceae_OR; Pseudomonadaceae; sfA; 24842; DQ117539.1 gg_id: 138558 structure (*Citrullus vulgaris* SCHARD.) -based approaches and terminal fragment length polymorphism (t-RFLP) rhizosphere soil watermelon |
| human waste | 25111 | Bacteria; Proteobacteria; Gammaproteobacteria_SP; Pseudomonadaceae_CL; Pseudomonadaceae_OR; Pseudomonadaceae; sfA; 25111; DQ813329.1 gg_id: 171423 *Pseudomonas* sp. str. IBUN P8B |
| human waste | 25314 | Bacteria; Proteobacteria; Gammaproteobacteria_SP; Pseudomonadaceae_CL; Pseudomonadaceae_OR; Pseudomonadaceae; sfA; 25314; AF290486.1 gg_id: 37108 cf. *Pseudomonas* sp. clone Llangefni 52 |
| human waste | 25374 | Bacteria; Proteobacteria; Gammaproteobacteria_SP; Pseudomonadaceae_CL; Pseudomonadaceae_OR; Pseudomonadaceae; sfA; 25374; DQ076645.1 gg_id: 131495 *Pseudomonas* sp. str. LDC-25 |
| human waste | 25501 | Bacteria; Proteobacteria; Gammaproteobacteria_SP; Pseudomonadaceae_CL; Pseudomonadaceae_OR; Pseudomonadaceae; sfA; 25501; EU169157.1 gg_id: 243135 *Pseudomonas fluorescens* str. B50 |
| human waste | 25741 | Bacteria; Proteobacteria; Gammaproteobacteria_SP; Pseudomonadaceae_CL; Pseudomonadaceae_OR; Pseudomonadaceae; sfA; 25741; EU535331.1 gg_id: 286266 profile human microbiota antecubital fossa (inner elbow) skin clone nbt01f11 |
| human waste | 26120 | Bacteria; Proteobacteria; Gammaproteobacteria_SP; Pseudomonadaceae_CL; Pseudomonadaceae_OR; Pseudomonadaceae; sfA; 26120; AY958788.1 gg_id: 136688 Microbes on human vaginal epithelium clone rRNA015 |
| human waste | 26144 | Bacteria; Proteobacteria; Gammaproteobacteria_SP; Pseudomonadaceae_CL; Pseudomonadaceae_OR; Pseudomonadaceae; sfA; 26144; AB369365.1 gg_id: 288200 *Pseudomonas* sp. str. GmFRB106 |
| human waste | 26354 | Bacteria; Proteobacteria; Gammaproteobacteria_SP; Pseudomonadaceae_CL; Pseudomonadaceae_OR; Pseudomonadaceae; sfA; 26354; AF130950.1 gg_id: 8581 *Pseudomonas syringae* str. A90 |
| human waste | 26386 | Bacteria; Proteobacteria; Gammaproteobacteria_SP; Pseudomonadaceae_CL; Pseudomonadaceae_OR; Pseudomonadaceae; sfA; 26386; AF511509.1 gg_id: 65395 *Pseudomonas* sp. SaU6sm |
| human waste | 26536 | Bacteria; Proteobacteria; Gammaproteobacteria_SP; Pseudomonadaceae_CL; Pseudomonadaceae_OR; Pseudomonadaceae; sfA; 26536; AY741354.1 gg_id: 102091 *Burkholderia cepacia* str. ATCC 53795 |

TABLE 3-continued

Sewage ID taxa
HUMAN WASTE IDENTIFIER TAXA

| Source | #OTU ID | Lineage for representative OTU |
|---|---|---|
| human waste | 26565 | Bacteria; Proteobacteria; Gammaproteobacteria_SP; Pseudomonadaceae_CL; Pseudomonadaceae_OR; Pseudomonadaceae; sfA; 26565; EU540079.1 gg_id: 281471 profile human microbiota antecubital fossa (inner elbow) skin clone nbt245b07 |
| human waste | 26787 | Bacteria; Proteobacteria; Gammaproteobacteria_SP; Pseudomonadaceae_CL; Pseudomonadaceae_OR; Pseudomonadaceae; sfA; 26787; DQ088800.1 gg_id: 132141 energy crustal biotome clone MP104-1109-b31 |
| human waste | 26925 | Bacteria; Proteobacteria; Gammaproteobacteria_SP; Pseudomonadaceae_CL; Pseudomonadaceae_OR; Pseudomonadaceae; sfA; 26925; EU249969.1 gg_id: 247979 Polyphasic description *Pocillopora* mucus secreted *Pacillopora meandrina* coral colony Palmyra Atoll clone PmeaMucD12 |
| human waste | 27306 | Bacteria; Proteobacteria; Gammaproteobacteria_SP; Pseudomonadaceae_CL; Pseudomonadaceae_OR; Pseudomonadaceae; sfA; 27306; DQ140183.1 gg_id: 139457 *Pseudomonas* sp. HF12-8 |
| human waste | 27470 | Bacteria; Proteobacteria; Gammaproteobacteria_SP; Pseudomonadaceae_CL; Pseudomonadaceae_OR; Pseudomonadaceae; sfA; 27470; EU037914.1 gg_id: 243229 Metabolic Profiles Microbial Chlorinated Pesticides Contaminated Sites Three Geographical Habitats India soil around pesticides and chemicals manufacturing site clone IPL 28 |
| human waste | 27550 | Bacteria; Proteobacteria; Gammaproteobacteria_SP; Pseudomonadaceae_CL; Pseudomonadaceae_OR; Pseudomonadaceae; sfA; 27550; AY651925.1 gg_id: 106092 *Pseudomonas alcaligenes* str. X1 |
| human waste | 23438 | Bacteria; Proteobacteria; Gammaproteobacteria_SP; Xanthomonadales_CL; Xanthomonadales; Frateuria_FM; sfA; 23438; L76222.1 gg_id: 100598 *Rhodanobacter lindaniclasticus* |
| human waste | 33272 | Bacteria; Proteobacteria; Gammaproteobacteria_SP; Xanthomonadales_CL; Xanthomonadales; Unclassified; sfA; 33272; AY566580.1 gg_id: 108726 *Xanthomonas* sp. str. PG-07 |
| human waste | 34331 | Bacteria; Proteobacteria; Gammaproteobacteria_SP; Xanthomonadales_CL; Xanthomonadales; Unclassified; sfA; 34331; EF111207.1 gg_id: 181365 Bogota River site E2-Se-PRp clone RBE2CI-175 |
| human waste | 32409 | Bacteria; Synergistetes_Aminanaerobia; *Synergistes*_SP; *Synergistes*_CL; *Synergistes*_OR; *Synergistes*_FM; sfA; 32409; AY217431.1 gg_id: 81485 TCE-dechlorinating microbial community clone 11H |
| human waste | 32560 | Bacteria; Synergistetes_Aminanaerobia; *Synergistes*_SP; *Synergistes*_CL; *Synergistes*_OR; *Synergistes*_FM; sfA; 32560; CR933275.1 gg_id: 109579 Evry municipal wastewater treatment plant clone 053B03_B_DI_P58 |
| human waste | 55487 | Bacteria; Verrucomicrobia; Verrucomicrobiae_SP; *Akkermansia*_CL; *Akkermansia*_OR; *Akkermansia*_FM; sfA; 55487; EF099597.1 gg_id: 184418 mouse cecum clone SWPT4_aaa01f05 |
| human waste | 55509 | Bacteria; Verrucomicrobia; Verrucomicrobiae_SP; *Akkermansia*_CL; *Akkermansia*_OR; *Akkermansia*_FM; sfA; 55509; DQ805510.1 gg_id: 198415 human fecal clone RL203_aai63e12 |
| human waste | 55626 | Bacteria; Verrucomicrobia; Verrucomicrobiae_SP; *Akkermansia*_CL; *Akkermansia*_OR; *Akkermansia*_FM; sfA; 55626; DQ793491.1 gg_id: 191258 human fecal clone RL199_aaj44e01 |
| human waste | 55685 | Bacteria; Verrucomicrobia; Verrucomicrobiae_SP; *Akkermansia*_CL; *Akkermansia*_OR; *Akkermansia*_FM; sfA; 55685; DQ805244.1 gg_id: 196331 human fecal clone RL249_aaj83f07 |
| human waste | 55797 | Bacteria; Verrucomicrobia; Verrucomicrobiae_SP; *Akkermansia*_CL; *Akkermansia*_OR; *Akkermansia*_FM; sfA; 55797; EF099043.1 gg_id: 185896 mouse cecum clone SWPT2_aaa01e03 |
| human waste | 55910 | Bacteria; Verrucomicrobia; Verrucomicrobiae_SP; *Akkermansia*_CL; *Akkermansia*_OR; *Akkermansia*_FM; sfA; 55910; EU508233.1 gg_id: 271982 cecal contents *Mus musculus* strain C57BL/6J; MD26 clone MD26_aaa03h10 |
| human waste | 55980 | Bacteria; Verrucomicrobia; Verrucomicrobiae_SP; *Akkermansia*_CL; *Akkermansia*_OR; *Akkermansia*_FM; sfA; 55980; EU509432.1 gg_id: 272683 cecal contents *Mus musculus* strain C57BL/6J; MD9 clone MD9_aap58b11 |
| human waste | 56046 | Bacteria; Verrucomicrobia; Verrucomicrobiae_SP; *Akkermansia*_CL; *Akkermansia*_OR; *Akkermansia*_FM; sfA; 56046; DQ793699.1 gg_id: 176844 human fecal clone RL246_aai75h04 |
| human waste | 56083 | Bacteria; Verrucomicrobia; Verrucomicrobiae_SP; *Akkermansia*_CL; *Akkermansia*_OR; *Akkermansia*_FM; sfA; 56083; DQ803994.1 gg_id: 196460 human fecal clone RL200_aai60g11 |
| human waste | 56089 | Bacteria; Verrucomicrobia; Verrucomicrobiae_SP; *Akkermansia*_CL; *Akkermansia*_OR; *Akkermansia*_FM; sfA; 56089; DQ805361.1 gg_id: 180315 human fecal clone RL203_aai61f09 |
| human waste | 56194 | Bacteria; Verrucomicrobia; Verrucomicrobiae_SP; *Akkermansia*_CL; *Akkermansia*_OR; *Akkermansia*_FM; sfA; 56194; DQ806025.1 gg_id: 178761 human fecal clone RL186_aah60b02 |
| human waste | 56238 | Bacteria; Verrucomicrobia; Verrucomicrobiae_SP; *Akkermansia*_CL; *Akkermansia*_OR; *Akkermansia*_FM; sfA; 56238; EU507707.1 gg_id: 273646 cecal contents *Mus musculus* strain C57BL/6J; MD23 clone MD23_aaa03e02 |
| human waste | 56281 | Bacteria; Verrucomicrobia; Verrucomicrobiae_SP; *Akkermansia*_CL; *Akkermansia*_OR; *Akkermansia*_FM; sfA; 56281; EF099244.1 gg_id: 175782 mouse cecum clone SWPT2_aaa04e04 |
| human waste | 56324 | Bacteria; Verrucomicrobia; Verrucomicrobiae_SP; *Akkermansia*_CL; *Akkermansia*_OR; *Akkermansia*_FM; sfA; 56324; EU507207.1 gg_id: 263196 cecal contents *Mus musculus* strain C57BL/6J; MD22 clone MD22_aaa03e05 |
| human waste | 56691 | Bacteria; Verrucomicrobia; Verrucomicrobiae_SP; *Akkermansia*_CL; *Akkermansia*_OR; *Akkermansia*_FM; sfA; 56691; DQ805310.1 gg_id: 177858 human fecal clone RL203_aai61a03 |
| human waste | 56702 | Bacteria; Verrucomicrobia; Verrucomicrobiae_SP; *Akkermansia*_CL; *Akkermansia*_OR; *Akkermansia*_FM; sfA; 56702; DQ805557.1 gg_id: 178510 human fecal clone RL203_aai64b11 |
| human waste | 56706 | Bacteria; Verrucomicrobia; Verrucomicrobiae_SP; *Akkermansia*_CL; *Akkermansia*_OR; *Akkermansia*_FM; sfA; 56706; DQ824314.1 gg_id: 194496 human fecal clone RL304_aal74d01 |
| human waste | 56707 | Bacteria; Verrucomicrobia; Verrucomicrobiae_SP; *Akkermansia*_CL; *Akkermansia*_OR; *Akkermansia*_FM; sfA; 56707; DQ805412.1 gg_id: 183962 human fecal clone RL203_aai62c08 |
| human waste | 56729 | Bacteria; Verrucomicrobia; Verrucomicrobiae_SP; *Akkermansia*_CL; *Akkermansia*_OR; *Akkermansia*_FM; sfA; 56729; DQ805539.1 gg_id: 185779 human fecal clone RL203_aai64a01 |

What is claimed is:

1. An analysis system for detecting the source of fecal bacteria contamination in an environmental sample, comprising probes capable of detecting at least 10% of the source-specific taxa set forth in Table 1 (bird), Table 2 (grazer), Table 3 (sewage), or a combination thereof, wherein each of said probes is about 16 to about 35 nucleotides in length, and wherein the analysis system consists of about $10^5$ to about $10^8$ of said probes.

2. The analysis system of claim 1, comprising probes capable of detecting at least 20% of the source-specific taxa set forth in Table 1 (bird), Table 2 (grazer), Table 3 (sewage), or a combination thereof.

3. The analysis system of claim 1, wherein the probes are capable of detecting at least 10% of the source-specific taxa set forth in Table 1 (bird).

4. The analysis system of claim 1, wherein the probes are capable of detecting at least 10% of the source-specific taxa set forth in Table 2 (grazer).

5. The analysis system of claim 1, wherein the probes are capable of detecting at least 10% of the source-specific taxa set forth in Table 3 (sewage).

6. The analysis system of claim 1, wherein the probes are capable of detecting at least 10% of each of the source-specific taxa set forth in Table 1 (bird), Table 2 (grazer), and Table 3 (sewage).

7. The analysis systems of claim 1, wherein the probes are probes for microarray probe hybridization.

8. The analysis system of claim 1, wherein the analysis system comprises a microarray, a bead array, a through-hole array, or a well array.

9. The analysis system of claim 1, wherein the environmental sample has fecal contamination from bird feces.

10. The analysis system of claim 1, wherein the environmental sample has fecal contamination from grazer feces.

11. The analysis system of claim 1, wherein the environmental sample has fecal contamination from human feces and/or sewage.

12. The analysis system of claim 1, wherein the environmental sample is an air sample, a water sample, a soil sample, or a mixture thereof.

13. The analysis system of claim 1, wherein the environmental sample is a solid sample.

14. The analysis system of claim 1, wherein the probes are capable of hybridizing to a target sequence of at least 15% of the source-specific taxa set forth in Table 1 (bird), Table 2 (grazer), Table 3 (sewage), or a combination thereof.

15. The analysis system of claim 14, wherein the target sequence is a 16S rRNA gene sequence.

16. The analysis system of claim 1, wherein the analysis system comprises about $10^5$ to about $10^7$ of said probes.

17. The analysis system of claim 1, further comprising 1 to about 500000 control probes.

18. The analysis system of claim 1, wherein each of said probes is about 17 to about 35 nucleotides in length.

19. The analysis system of claim 1, wherein each of said probes is about 18 to about 35 nucleotides in length.

\* \* \* \* \*